US012162956B2

(12) United States Patent
Love

(10) Patent No.: US 12,162,956 B2
(45) Date of Patent: Dec. 10, 2024

(54) PEPTIDES AND METHODS FOR REDUCING SKIN PIGMENTATION

(71) Applicant: GLO Pharma, Inc., Carlsbad, CA (US)

(72) Inventor: Robert A. Love, Encinitas, CA (US)

(73) Assignee: GLO Pharma, Inc., Carlsbad, CA (US)

( * ) Notice: Subject to any disclaimer, the term of this patent is extended or adjusted under 35 U.S.C. 154(b) by 0 days.

(21) Appl. No.: 18/473,073

(22) Filed: Sep. 22, 2023

(65) Prior Publication Data

US 2024/0190917 A1 Jun. 13, 2024

Related U.S. Application Data

(63) Continuation of application No. PCT/US2022/021579, filed on Mar. 23, 2022.

(60) Provisional application No. 63/271,646, filed on Oct. 25, 2021, provisional application No. 63/165,611, filed on Mar. 24, 2021.

(51) Int. Cl.
*C07K 7/06* (2006.01)
*C07K 1/10* (2006.01)
*C07K 1/107* (2006.01)

(52) U.S. Cl.
CPC .............. *C07K 7/06* (2013.01); *C07K 1/1077* (2013.01)

(58) Field of Classification Search
CPC ................................ C07K 7/06; C07K 1/1077
See application file for complete search history.

(56) References Cited

U.S. PATENT DOCUMENTS

| | | | |
|---|---|---|---|
| 4,372,977 A | 2/1983 | Lover et al. | |
| 4,855,090 A | 8/1989 | Wallach | |
| 4,968,450 A | 11/1990 | Kamegai et al. | |
| 5,804,216 A | 9/1998 | Terren et al. | |
| 5,846,514 A | 12/1998 | Foster et al. | |
| 5,853,755 A | 12/1998 | Foldvari | |
| 5,993,851 A | 11/1999 | Foldvari | |
| 5,993,852 A | 11/1999 | Foldvari et al. | |
| 6,334,997 B1 | 1/2002 | Foster et al. | |
| 6,656,499 B1 | 12/2003 | Foldvari et al. | |
| 6,696,424 B1 | 2/2004 | Wheeler | |
| 11,130,782 B2 | 9/2021 | Love | |
| 2003/0119774 A1 | 6/2003 | Foldvari et al. | |
| 2004/0219232 A1 | 11/2004 | Lipton | |
| 2006/0040354 A1 | 2/2006 | O'Keefe | |
| 2006/0233901 A1 | 10/2006 | Jamieson et al. | |
| 2008/0008747 A1 | 1/2008 | Royds | |
| 2009/0081142 A1 | 3/2009 | Omura et al. | |
| 2009/0098171 A1 | 4/2009 | Alard et al. | |
| 2010/0112016 A1 | 5/2010 | Carli et al. | |
| 2010/0166689 A1 | 7/2010 | Waugh | |
| 2010/0278845 A1 | 11/2010 | Heavner | |
| 2012/0093718 A1 | 4/2012 | Parchment et al. | |
| 2012/0196796 A1 | 8/2012 | Soares et al. | |
| 2016/0151283 A1 | 6/2016 | Manca et al. | |
| 2017/0105936 A1 | 4/2017 | Cerundolo et al. | |
| 2017/0304232 A1 | 10/2017 | Khan et al. | |
| 2017/0313756 A1 | 11/2017 | Perricone et al. | |
| 2018/0177739 A1 | 6/2018 | Johnson et al. | |
| 2018/0250075 A1 | 9/2018 | Cho | |
| 2018/0360757 A1 | 12/2018 | Doroudian et al. | |
| 2019/0183787 A1 | 6/2019 | Dizerega | |
| 2019/0209498 A1 | 7/2019 | Khan et al. | |
| 2020/0062804 A1 | 2/2020 | Tanaka et al. | |
| 2020/0407768 A1 | 12/2020 | Hirota et al. | |
| 2022/0048950 A1 | 2/2022 | Love | |
| 2022/0218611 A1 | 7/2022 | Foldvari | |
| 2022/0313606 A1 | 10/2022 | Foldvari | |
| 2023/0143474 A1 | 5/2023 | Foldvari | |
| 2023/0157954 A1 | 5/2023 | Foldvari | |
| 2023/0270635 A1 | 8/2023 | Love et al. | |
| 2024/0122823 A1 | 4/2024 | Foldvari | |
| 2024/0139089 A1 | 5/2024 | Love et al. | |
| 2024/0189231 A1 | 6/2024 | Foldvari | |
| 2024/0238200 A1 | 7/2024 | Foldvari | |

FOREIGN PATENT DOCUMENTS

| | | | | |
|---|---|---|---|---|
| CA | 2324403 A1 | 7/2000 | | |
| CA | 2458443 A1 | 3/2003 | | |
| CN | 108778244 A | 11/2018 | | |
| CN | 108948151 A | * 12/2018 | ............... | A61K 8/64 |
| EP | 0711148 A1 | 5/1996 | | |
| EP | 2498792 A1 | 9/2012 | | |
| FR | 2816577 A1 | 5/2002 | | |

(Continued)

OTHER PUBLICATIONS

Albuquerque, Edson et al. Mammalian nicotinic acetylcholine receptors: from structure to function. Physiol Rev vol. 89,1: 73-120 (2009).
Aulton's Pharmaceutical, The Design and Manufacture of Medicines. Fourth Edition. p. 442-449 (2021).
Becker, Lillian C., Safety Assessment of PEG-Distearates as Used in Cosmetics. Cosmetic Ingredient Review :1-36 (2015).
Chinese Patent Application No. 2020800813833 First Office Action dated Apr. 27, 2023.
Co-pending U.S. Appl. No. 18/470,334, inventor Foldvari; Marianna, filed Sep. 19, 2023.
Dragicevic, Nina., Percutaneous Penetration Enhancers Chemical Methods in Penetration Enhancement. Springer :1-415 (2015).
European Patent Application No. 4034087A1 Search Report dated Sep. 27, 2023.
Falla et al.: Cosmeceuticals and peptides. Clinics in Dermatology 27:485-494 (2009).

(Continued)

*Primary Examiner* — Amber D Steele
(74) *Attorney, Agent, or Firm* — Wilson Sonsini Goodrich & Rosati

(57) ABSTRACT

The present disclosure relates to novel peptide antagonists that inhibit binding of melanocyte stimulating hormone to the melanocortin 1 receptor. The peptide antagonists of the disclosure are useful in cosmetic compositions that prevent or reduce the appearance of skin discoloration caused by pigmentation. The disclosure further relates to cosmetic compositions comprising a peptide antagonist of the disclosure, and methods for their use for preventing or reducing the appearance of skin discoloration in a subject in need thereof.

12 Claims, 3 Drawing Sheets

Specification includes a Sequence Listing.

(56) References Cited

FOREIGN PATENT DOCUMENTS

| | | | |
|---|---|---|---|
| FR | 2846238 A1 | 4/2004 |
| FR | 2876577 A1 | 4/2006 |
| JP | 2001514212 A | 9/2001 |
| JP | 2009515579 A | 4/2009 |
| JP | 2010522698 A | 7/2010 |
| JP | 2019510215 A | 4/2019 |
| KR | 100748035 B1 | 8/2007 |
| WO | WO-9503787 A1 | 2/1995 |
| WO | WO-9911247 A1 | 3/1999 |
| WO | WO-0130808 A1 | 5/2001 |
| WO | WO-0135998 A1 | 5/2001 |
| WO | WO-2006012414 A2 | 2/2006 |
| WO | WO-2008119160 A1 | 10/2008 |
| WO | WO-2011060083 A1 | 5/2011 |
| WO | WO-2015023601 A1 | 2/2015 |
| WO | WO-2018144093 A2 | 8/2018 |
| WO | WO-2018213932 A1 | 11/2018 |
| WO | WO-2020081583 A1 | 4/2020 |
| WO | WO-2021056106 A1 | 4/2021 |
| WO | WO-2021216572 A1 | 10/2021 |
| WO | WO-2022204287 A1 | 9/2022 |
| WO | WO-2022204305 A2 | 9/2022 |
| WO | WO-2022204308 A1 | 9/2022 |
| WO | WO-2022204309 A1 | 9/2022 |
| WO | WO-2023081259 A2 | 5/2023 |

OTHER PUBLICATIONS

Foldvari et al.: Topical Delivery of Interferon Alpha by Biphasic Vesicles: Evidence for a Novel Nanopathway across the Stratum Corneum. Molecular Pharmaceutics. 7(3):751-762 (2010).
Folvari: Observations of membrane fusion in a liposome dispersion: the missing fusion intermediate? F1000 Research. 4(4):1-11 (2015).
Handbook of Pharm Excipients—Glyceryl Monostearate (sixth edition) p. 290-293 (2009).
Kalamida, Dimitra et al. Muscle and neuronal nicotinic acetylcholine receptors. Structure, function and pathogenicity. The FEBS Journal vol. 274,15: 3799-3845 (2007).
Koivukangas et al.: Increased collagen synthesis in psoriasis in vivo. Arch Dermatol Res. 287:171-175 (1995).
Moghadam et al.: Effect of Chemical Permeation Enhancers on Stratum Corneum Barrier Lipid Organizational Structure and Interferon Alpha Permeability. Molecular Pharmaceutics. 10:2248-2260 (2013).
PCT/US2022/021554 International Preliminary Report on Patentability dated Oct. 5, 2023.
PCT/US2022/021585 International Preliminary Report on Patentability dated Oct. 5, 2023.
PCT/US2022/048780 International Search Report and Written Opinion dated Apr. 27, 2023.
Rahiman et al.: Novasome: A Pioneering Advancement in Vesicular Drug Delivery. International Journal of Applied Pharmaceutics. 13(1):59-64 (2021).
Sakdiset, Pajaree, et al., Potential of Stratum Corneum Lipid Liposomes for Screening of Chemical Skin Penetration Enhancers. Chemical and Pharmaceutical Bulletin 65:776-783 (2017).
Sekhon, Bhupinder Singh., Surfactants: Pharmaceutical and Medicinal Aspects. Journal of Pharmaceutical Technology 1:43-68 (2013).
Shen et al.: Effect of Nonionic Surfactants on Percutaneous Absorption of Salicylic Acid and Sodium Salicylate in the Presence of Dimethyl Sulfoxide. Journal of Pharmaceutical Sciences. 65(12):1780-1783 (1976).
Shin et al.: Effects of non-ionic surfactants as permeation enhancers towards piroxicam from the poloxamer gel through rat skins. International Journal of Pharmaceutics. 222(2):199-203 (2001).
Shin et al.: Enhanced transdermal delivery of triprolidine from the ethylene-vinyl acetate matrix. European Journal of Pharmaceutics and Biopharmaceutics. 54(3):325-328 (2002).
Som, Iti, et al., Status of Surfactants as Penetration Enhancers in Transdermal Drug Delivery. Journal of Pharmacy & Bioallied Sciences 4(1) :1-8 (2012).
U.S. Appl. No. 17/841,924 Office Action dated Jun. 2, 2023.
U.S. Appl. No. 18/150,144 Office Action dated Apr. 18, 2023.
U.S. Appl. No. 18/150,145 Final Office Action dated Sep. 8, 2023.
U.S. Appl. No. 18/150,145 Office Action dated May 19, 2023.
U.S. Appl. No. 18/150,145 Office Action dated May 8, 2023.
U.S. Appl. No. 17/702,608 Office Action dated Apr. 25, 2024.
Website: Emulsifying Agents in Pharmaceuticals. https://pharmaeducation.net/emulsifying-agents/ 11 pages (2023).
Anthony et al.: Synthesis of Radiolabeled Compounds. Journal of Radioanalytical and Nuclear Chemistry 64(1-2):9-32 (1981).
Berge et al.: Pharmaceutical Salts. Journal of Pharmaceutical Sciences 66:1-19 (1977).
Bundgard, H. Design of Prodrugs. 1985; pp. 7-9, 21-24 (Elsevier, Amsterdam).
Dean et al.: Recent Advances in the Synthesis and Applications of Radiolabeled Compounds for Drug Discovery and Development. Current Pharmaceutical Design 6:110 (2000) (Preface only).
Dekan et al.: α-Conotoxin Iml Incorporating Stable Cystathionine Bridges Maintains Full Potency and Identical Three-Dimensional Structure. Journal of the American Chemical Society 133:15866-15869 (2011).
Dhamecha: Drug Vehicle Based Approaches of Penetration Enhancement. 1(1):24-46 (2009).
DiMarco et al.: Discovery of novel, highly potent and selective b-hairpin mimetic CXCR4 inhibitors with excellent anti-HIV activity and pharmacokinetic profiles. Bioorganic & Medicinal Chemistry 14: 8396-8404 (2006).
Griffin et al.: "HLB" or "Hydrophilic-Lipophilic Balance" value refers to standard HLB. Official Journal of the Society of Cosmetic Chemists 5:249 (1954).
Gupta et al.: Biocompatible Micro emulsions and Their Prospective Uses in Drug Deliver. Journal of Pharmaceutical Sciences. 97(1):22-45. (2008).
Higuchi et al.: Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Horrell et al.: Melanocortin 1 Receptor: Structure, Function, and Regulation. Frontiers in Genetics 7(95):1-16 (2016).
Jayawickreme et al.: Discovery and Structure—Function Analysis of α-Melanocyte-stimulating Hormone Antagonists. The Journal of Biological Chemistry. 269(47):29846-29854 (1994).
Kabalka et al. The Synthesis of Radiolabeled Compounds via Organometallic Intermediates. Tetrahedron 45(21):6601-6621 (1989).
Kirby et al.: Gemini surfactants: new synthetic vectors for gene transfection. Angew Chem Int Ed Engl. 42(13):1448-1457 (2003).
Knerr et al.: Synthesis and activity of thioether-containing analogues of the complement inhibitor compstatin. ACS Chemical Biology 6(7):753-760 (2011).
Kyte et al.: A simple method for displaying the hydropathic character of a protein. Journal of Molecular Biology 157:105-131 (1982).
Lane. Skin penetration enhancers. Int. J. Pharm. 447(1-2):12-21 (2013).
Lichtenberg et al.: The Mechanism of Detergent Solubilization of Lipid Bilayers. Biophysical Journal. 105:289-299 (2013).
Lotioncrafter. Lotioncrafter.com. Sorbitan Stearate Product Info. Sep. 20, 2020 [retrieved May 18, 2022] https://webarchive.org/web/20200920113912/https://lotionlcrafter.com/products/sorbitan-stearate [entire document].
Makino et al.: Evaluation of a Hydroquinone-free Skin Brightening Product Using in Vitro Inhibition of Melanogenesis and Clinical Reduction of Ultraviolet-induced Hyperpigmentation. Journal of Drugs in Dermatology 12:s16-s20 (2013).
McClements: Nanoemulsions versus microemulsions: terminology, differences, and similarities. Soft Matter. 8:1719-1729 (2012).
McNulty et al.: Structures of the Agouti Signaling Protein. Journal of Molecular Biology 346:1059-1070 (2005).
Menger et al.: Gemini Surfactants. Angew Chem Int Ed Engl. 39(11):1906-1920 (2000).

(56) References Cited

OTHER PUBLICATIONS

Nguyen et al.: Making circles: recent advance in chemical and enzymatic approaches in peptide macrocyclization. Journal of Biochemistry and Chemical Sciences 1(1):1-13 (2017).
Nix et al.: Molecular and Functional Analysis of Human β-Defensin 3 Action at Melanocortin Receptors. Chem Biol. 20(6):784-795 (2013).
Otto et al.: Formulation effects of topical emulsions on transdermal and dermal delivery. International Journal of Cosmetic Science. 31:1-19 (2009).
Paliwal et al.: Pharmaceutical Considerations of Microemulsion as a Drug Delivery System. Journal of Drug Delivery & Therapeutics. 9(4-s):661-665 (2019).
PCT/CA2020/051275 International Search Report and Written Opinion dated Dec. 21, 2020.
PCT/US2022/021554 International Search Report and Written Opinion dated Jun. 10, 2022.
PCT/US2022/021579 International Search Report and Written Opinion dated Oct. 5, 2022.
PCT/US2022/021579 Invitation to Pay Additional Fees dated Jul. 22, 2022.
PCT/US2022/021585 International Search Report and Written Opinion dated Jul. 7, 2022.
Spicer et al.: Selective chemical protein modification. Nature Communications 5:4740 (2014).
Talegoankar et al.: Microemulsions: A Novel Approach to Enhanced Drug Delivery. Recent Patents on Drug Delivery & Formulation. 2:238-257 (2008).
Tam et al.: Chemical Synthesis of Circular Proteins. The Journal of Biological Chemistry 287(32):27020-27025 (2012).
U.S. Appl. No. 17/841,924 Final Office Action dated Nov. 17, 2022.
U.S. Appl. No. 17/841,924 Office Action dated Aug. 1, 2022.
Van Staden: Development of topical-transdermal self-emulsifying drug delivery systems. Sci. Pharm. 88:17 (2020).
Williams et al.: Penetration Enhancers. Advanced Drug Delivery Reviews. 64:128-137 (2012).
Zasada et al.: The assessment of the effect of a cosmetic product brightening the skin of people with discolorations of different etiology. Journal of Cosmetic Dermatology. 15:493-502 (2016).
Zhou et al.: Nano-formulations for transdermal drug delivery: A review. Chinese Chemical Letters. 29:1713-1724 (2018).
Abdulbaqi et al.: Ethosomal nanocarriers: the impact of constituents and formulation techniques on ethosomal properties, in vivo studies, and clinical trials. Int J Nanomedicine. 11:2279-2304 (2016).
Badenhorst et al.: Pharmaceutical Strategies for the Topical Dermal Delivery of Peptides/Proteins for Cosmetic and Therapeutic Applications. Austin J Pharmacol. 2(6):1036-1046 (2014).
Benson et al.: Proteins and peptides: strategies for delivery to and across the skin. J Pharm Sci. 97(9):3591-3610 (2008).
Bos et al.: The 500 Dalton rule for the skin penetration of chemical compounds and drugs. Exp Dermatol. 9(3):165-169 (2000).
Bravo et al.: Benefits of topical hyaluronic acid for skin quality and signs of skin aging: From literature review to clinical evidence. Dermatol Ther. 35(12):e15903 (2022).
Bukhari et al.: Hyaluronic acid, a promising skin rejuvenating biomedicine: A review of recent updates and pre-clinical and clinical investigations on cosmetic and nutricosmetic effects. Int J Biol Macromol. 120(Pt B):1682-1695 (2018).
Czekalla et al.: Noninvasive Determination of Epidermal and Stratum Corneum Thickness in vivo Using Two-Photon Microscopy and Optical Coherence Tomography: Impact of Body Area, Age, and Gender. Skin Pharmacol Physiol. 32(3):142-150 (2019).
Fallacara et al.: Hyaluronic Acid in the Third Millennium. Polymers (Basel). 10(7):701 (2018).
Foldvari et al.: Biphasic vesicles for topical delivery of interferon alpha in human volunteers and treatment of patients with human papillomavirus infections. Curr Drug Deliv. 8(3):307-319 (2011).
Foldvari et al.: Gene delivery into human skin in vitro using biphasic lipid vesicles. Curr Drug Deliv.3(1):89-93 (2006).
Foldvari et al.: Permeation enhancement by molecular organization switching (MOS): Biphasic vesicles for the cutaneous delivery of proteins. In: Percutaneous Penetration Enhancers Chemical Methods in Penetration Enhancement: Nanocarriers. 309-318 (2016).
Foldvari et al.: Perspectives on Using Nanoscale Delivery Systems in Dermatological Treatment. Current Dermatology Reports. 4(1):1-7 (2015).
Foldvari M. Biphasic vesicles: a novel topical drug delivery system. J Biomed Nanotechnol. 6(5):543-557 (2010).
Huzil et al.: Drug delivery through the skin: molecular simulations of barrier lipids to design more effective noninvasive dermal and transdermal delivery systems for small molecules, biologics, and cosmetics. Wiley Interdiscip Rev Nanomed Nanobiotechnol. 3(5):449-462 (2011).
Iaconisi et al.: Hyaluronic Acid: A Powerful Biomolecule with Wide-Ranging Applications—A Comprehensive Review. Int J Mol Sci. 24(12)(2023).
Kim et al.: A novel dermal delivery system using natural spicules for cosmetics and therapeutics. J Cosmet Dermatol. 21(10):4754-4764 (2022).
Kim et al. Arc-poration improves transdermal delivery of biomolecules. J Cosmet Dermatol. 23(6):2240-2248 (2024).
King et al.: Transdermal delivery of insulin from a novel biphasic lipid system in diabetic rats. Diabetes Technol Ther. 4(4):479-488 (2002).
Lademann et al.: Determination of the thickness and structure of the skin barrier by in vivo laser scanning microscopy. Laser Phys Lett. 5(4):311-315 (2008).
Lee et al.: Laser-assisted nanoparticle delivery to promote skin absorption and penetration depth of retinoic acid with the aim for treating photoaging. Int J Pharm. 627:122162 (2022).
Liatsopoulou et al.: Iontophoresis in dermal delivery: A review of applications in dermato-cosmetic and aesthetic sciences. Int J Cosmet Sci. 2023;45(2):117-132 (2023).
LV et al.: Collagen-Based Dissolving Microneedles with Flexible Pedestals: A Transdermal Delivery System for Both Anti-Aging and Skin Diseases. Adv Healthc Mater. 12(21):e2203295 (2023).
Mortazavi et al.: Skin permeability, a dismissed necessity for anti-wrinkle peptide performance. Int J Cosmet Sci. 44(2):232-248 (2022).
Papakonstantinou E, Roth M, Karakiulakis G. Hyaluronic acid: A key molecule in skin aging. Dermatoendocrinol. 4(3):253-258 (2012).
Salwowska et al.: Physiochemical properties and application of hyaluronic acid: a systematic review. J Cosmet Dermatol. 15(4):520-526 (2016).

\* cited by examiner

Manufacturing flow chart:

SEQUENCE LISTING

```
Sequence total quantity: 94
SEQ ID NO: 1          moltype = AA  length = 9
FEATURE               Location/Qualifiers
REGION                1..9
                      note = Description of Artificial Sequence: Synthetic peptide
MOD_RES               3
                      note = D-amino acid
MOD_RES               5
                      note = D-amino acid
source                1..9
                      mol_type = protein
                      organism = synthetic construct
SEQUENCE: 1
MPFRWFKPV                                                                 9
```

```
SEQ ID NO: 2            moltype = AA  length = 26
FEATURE                 Location/Qualifiers
source                  1..26
                        mol_type = protein
                        organism = Homo sapiens
SEQUENCE: 2
CCDPCASCQC RFFRSACSCR VLSLNC                                              26

SEQ ID NO: 3            moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 3
CCDPCASCYC RFFRSACYCR VLSLNC                                              26

SEQ ID NO: 4            moltype = AA  length = 9
FEATURE                 Location/Qualifiers
REGION                  1..9
                        note = Description of Artificial Sequence: Synthetic peptide
MOD_RES                 3..5
                        note = D-amino acid
source                  1..9
                        mol_type = protein
                        organism = synthetic construct
SEQUENCE: 4
MVFRWFKPV                                                                  9

SEQ ID NO: 5            moltype = AA  length = 9
FEATURE                 Location/Qualifiers
REGION                  1..9
                        note = Description of Artificial Sequence: Synthetic peptide
MOD_RES                 3..4
                        note = D-amino acid
source                  1..9
                        mol_type = protein
                        organism = synthetic construct
SEQUENCE: 5
MVFRWFKPV                                                                  9

SEQ ID NO: 6            moltype = AA  length = 9
FEATURE                 Location/Qualifiers
REGION                  1..9
                        note = Description of Artificial Sequence: Synthetic peptide
MOD_RES                 3..5
                        note = D-amino acid
source                  1..9
                        mol_type = protein
                        organism = synthetic construct
SEQUENCE: 6
MVFRWFRPV                                                                  9

SEQ ID NO: 7            moltype = AA  length = 9
FEATURE                 Location/Qualifiers
REGION                  1..9
                        note = Description of Artificial Sequence: Synthetic peptide
MOD_RES                 3..4
                        note = D-amino acid
source                  1..9
                        mol_type = protein
                        organism = synthetic construct
SEQUENCE: 7
MVFRWFRPV                                                                  9

SEQ ID NO: 8            moltype = AA  length = 9
FEATURE                 Location/Qualifiers
REGION                  1..9
                        note = Description of Artificial Sequence: Synthetic peptide
MOD_RES                 3
                        note = D-amino acid
MOD_RES                 5
                        note = D-amino acid
source                  1..9
                        mol_type = protein
                        organism = synthetic construct
```

```
SEQUENCE: 8
MVFRWFKPV                                                                       9

SEQ ID NO: 9           moltype = AA  length = 9
FEATURE                Location/Qualifiers
REGION                 1..9
                       note = Description of Artificial Sequence: Synthetic peptide
MOD_RES                3
                       note = D-amino acid
MOD_RES                5
                       note = D-amino acid
source                 1..9
                       mol_type = protein
                       organism = synthetic construct
SEQUENCE: 9
MVFRWFRPV                                                                       9

SEQ ID NO: 10          moltype = AA  length = 9
FEATURE                Location/Qualifiers
REGION                 1..9
                       note = Description of Artificial Sequence: Synthetic peptide
MOD_RES                3..4
                       note = D-amino acid
source                 1..9
                       mol_type = protein
                       organism = synthetic construct
SEQUENCE: 10
AVFRWFRPV                                                                       9

SEQ ID NO: 11          moltype = AA  length = 9
FEATURE                Location/Qualifiers
REGION                 1..9
                       note = Description of Artificial Sequence: Synthetic peptide
MOD_RES                3
                       note = D-amino acid
MOD_RES                5
                       note = D-amino acid
source                 1..9
                       mol_type = protein
                       organism = synthetic construct
SEQUENCE: 11
AVFRWFKPV                                                                       9

SEQ ID NO: 12          moltype = AA  length = 9
FEATURE                Location/Qualifiers
REGION                 1..9
                       note = Description of Artificial Sequence: Synthetic peptide
MOD_RES                3..5
                       note = D-amino acid
source                 1..9
                       mol_type = protein
                       organism = synthetic construct
SEQUENCE: 12
AVFRWFKPV                                                                       9

SEQ ID NO: 13          moltype = AA  length = 9
FEATURE                Location/Qualifiers
REGION                 1..9
                       note = Description of Artificial Sequence: Synthetic peptide
MOD_RES                3..4
                       note = D-amino acid
source                 1..9
                       mol_type = protein
                       organism = synthetic construct
SEQUENCE: 13
AVFRWFKPV                                                                       9

SEQ ID NO: 14          moltype = AA  length = 9
FEATURE                Location/Qualifiers
REGION                 1..9
                       note = Description of Artificial Sequence: Synthetic peptide
MOD_RES                3..5
                       note = D-amino acid
source                 1..9
                       mol_type = protein
                       organism = synthetic construct
SEQUENCE: 14
AVFRWFRPV                                                                       9
```

```
SEQ ID NO: 15          moltype = AA   length = 9
FEATURE                Location/Qualifiers
REGION                 1..9
                       note = Description of Artificial Sequence: Synthetic peptide
MOD_RES                3..5
                       note = D-amino acid
source                 1..9
                       mol_type = protein
                       organism = synthetic construct
SEQUENCE: 15
FVFRWFRPV                                                                         9

SEQ ID NO: 16          moltype = AA   length = 9
FEATURE                Location/Qualifiers
REGION                 1..9
                       note = Description of Artificial Sequence: Synthetic peptide
MOD_RES                3
                       note = D-amino acid
MOD_RES                5
                       note = D-amino acid
source                 1..9
                       mol_type = protein
                       organism = synthetic construct
SEQUENCE: 16
FVFRWFKPV                                                                         9

SEQ ID NO: 17          moltype = AA   length = 9
FEATURE                Location/Qualifiers
REGION                 1..9
                       note = Description of Artificial Sequence: Synthetic peptide
MOD_RES                3..5
                       note = D-amino acid
source                 1..9
                       mol_type = protein
                       organism = synthetic construct
SEQUENCE: 17
FVFRWFKPV                                                                         9

SEQ ID NO: 18          moltype = AA   length = 9
FEATURE                Location/Qualifiers
REGION                 1..9
                       note = Description of Artificial Sequence: Synthetic peptide
MOD_RES                3..4
                       note = D-amino acid
source                 1..9
                       mol_type = protein
                       organism = synthetic construct
SEQUENCE: 18
FVFRWFKPV                                                                         9

SEQ ID NO: 19          moltype = AA   length = 9
FEATURE                Location/Qualifiers
REGION                 1..9
                       note = Description of Artificial Sequence: Synthetic peptide
MOD_RES                3
                       note = D-amino acid
MOD_RES                5
                       note = D-amino acid
source                 1..9
                       mol_type = protein
                       organism = synthetic construct
SEQUENCE: 19
FVFRWFKPA                                                                         9

SEQ ID NO: 20          moltype = AA   length = 9
FEATURE                Location/Qualifiers
REGION                 1..9
                       note = Description of Artificial Sequence: Synthetic peptide
MOD_RES                3
                       note = D-amino acid
MOD_RES                5
                       note = D-amino acid
source                 1..9
                       mol_type = protein
                       organism = synthetic construct
SEQUENCE: 20
VPFRWFKPV                                                                         9

SEQ ID NO: 21          moltype = AA   length = 9
```

```
FEATURE              Location/Qualifiers
REGION               1..9
                     note = Description of Artificial Sequence: Synthetic peptide
MOD_RES              3
                     note = D-amino acid
MOD_RES              5
                     note = D-amino acid
source               1..9
                     mol_type = protein
                     organism = synthetic construct
SEQUENCE: 21
VVFRWFKPV                                                                        9

SEQ ID NO: 22        moltype = AA  length = 9
FEATURE              Location/Qualifiers
REGION               1..9
                     note = Description of Artificial Sequence: Synthetic peptide
MOD_RES              2..3
                     note = D-amino acid
MOD_RES              5
                     note = D-amino acid
source               1..9
                     mol_type = protein
                     organism = synthetic construct
SEQUENCE: 22
VPFRWFKPV                                                                        9

SEQ ID NO: 23        moltype = AA  length = 9
FEATURE              Location/Qualifiers
REGION               1..9
                     note = Description of Artificial Sequence: Synthetic peptide
MOD_RES              3
                     note = D-amino acid
MOD_RES              5
                     note = D-amino acid
source               1..9
                     mol_type = protein
                     organism = synthetic construct
SEQUENCE: 23
VPFRWFRPV                                                                        9

SEQ ID NO: 24        moltype = AA  length = 9
FEATURE              Location/Qualifiers
REGION               1..9
                     note = Description of Artificial Sequence: Synthetic peptide
MOD_RES              3
                     note = D-amino acid
MOD_RES              5
                     note = D-amino acid
source               1..9
                     mol_type = protein
                     organism = synthetic construct
SEQUENCE: 24
EPFRWFKPV                                                                        9

SEQ ID NO: 25        moltype = AA  length = 9
FEATURE              Location/Qualifiers
REGION               1..9
                     note = Description of Artificial Sequence: Synthetic peptide
MOD_RES              3
                     note = D-amino acid
MOD_RES              5
                     note = D-amino acid
source               1..9
                     mol_type = protein
                     organism = synthetic construct
SEQUENCE: 25
EVFRWFKPV                                                                        9

SEQ ID NO: 26        moltype = AA  length = 9
FEATURE              Location/Qualifiers
REGION               1..9
                     note = Description of Artificial Sequence: Synthetic peptide
MOD_RES              3
                     note = D-amino acid
MOD_RES              5
                     note = D-amino acid
```

```
source                  1..9
                        mol_type = protein
                        organism = synthetic construct
SEQUENCE: 26
EVFRWFRPV                                                                    9

SEQ ID NO: 27           moltype = AA   length = 9
FEATURE                 Location/Qualifiers
REGION                  1..9
                        note = Description of Artificial Sequence: Synthetic peptide
MOD_RES                 5
                        note = D-amino acid
source                  1..9
                        mol_type = protein
                        organism = synthetic construct
SEQUENCE: 27
MVFRWFKPV                                                                    9

SEQ ID NO: 28           moltype = AA   length = 9
FEATURE                 Location/Qualifiers
REGION                  1..9
                        note = Description of Artificial Sequence: Synthetic peptide
MOD_RES                 4..5
                        note = D-amino acid
source                  1..9
                        mol_type = protein
                        organism = synthetic construct
SEQUENCE: 28
MVFRWFKPV                                                                    9

SEQ ID NO: 29           moltype = AA   length = 9
FEATURE                 Location/Qualifiers
REGION                  1..9
                        note = Description of Artificial Sequence: Synthetic peptide
MOD_RES                 5
                        note = D-amino acid
source                  1..9
                        mol_type = protein
                        organism = synthetic construct
SEQUENCE: 29
MVFRWFRPV                                                                    9

SEQ ID NO: 30           moltype = AA   length = 9
FEATURE                 Location/Qualifiers
REGION                  1..9
                        note = Description of Artificial Sequence: Synthetic peptide
MOD_RES                 5
                        note = D-amino acid
source                  1..9
                        mol_type = protein
                        organism = synthetic construct
SEQUENCE: 30
MVFRWFKPA                                                                    9

SEQ ID NO: 31           moltype = AA   length = 8
FEATURE                 Location/Qualifiers
REGION                  1..8
                        note = Description of Artificial Sequence: Synthetic peptide
MOD_RES                 3..4
                        note = D-amino acid
source                  1..8
                        mol_type = protein
                        organism = synthetic construct
SEQUENCE: 31
IFRWFKPV                                                                     8

SEQ ID NO: 32           moltype = AA   length = 8
FEATURE                 Location/Qualifiers
REGION                  1..8
                        note = Description of Artificial Sequence: Synthetic peptide
MOD_RES                 4
                        note = D-amino acid
source                  1..8
                        mol_type = protein
                        organism = synthetic construct
SEQUENCE: 32
IFRWFKPV                                                                     8
```

```
SEQ ID NO: 33           moltype = AA  length = 8
FEATURE                 Location/Qualifiers
REGION                  1..8
                        note = Description of Artificial Sequence: Synthetic peptide
MOD_RES                 2
                        note = D-amino acid
MOD_RES                 4
                        note = D-amino acid
source                  1..8
                        mol_type = protein
                        organism = synthetic construct
SEQUENCE: 33
IFRWFKPV                                                                         8

SEQ ID NO: 34           moltype = AA  length = 8
FEATURE                 Location/Qualifiers
REGION                  1..8
                        note = Description of Artificial Sequence: Synthetic peptide
MOD_RES                 2..4
                        note = D-amino acid
source                  1..8
                        mol_type = protein
                        organism = synthetic construct
SEQUENCE: 34
IFRWFKPV                                                                         8

SEQ ID NO: 35           moltype = AA  length = 9
FEATURE                 Location/Qualifiers
REGION                  1..9
                        note = Description of Artificial Sequence: Synthetic peptide
MOD_RES                 3..5
                        note = D-amino acid
source                  1..9
                        mol_type = protein
                        organism = synthetic construct
SEQUENCE: 35
MVFRWFKPV                                                                        9

SEQ ID NO: 36           moltype = AA  length = 9
FEATURE                 Location/Qualifiers
REGION                  1..9
                        note = Description of Artificial Sequence: Synthetic peptide
MOD_RES                 2..3
                        note = D-amino acid
MOD_RES                 5
                        note = D-amino acid
source                  1..9
                        mol_type = protein
                        organism = synthetic construct
SEQUENCE: 36
MPFRWFKPV                                                                        9

SEQ ID NO: 37           moltype = AA  length = 9
FEATURE                 Location/Qualifiers
REGION                  1..9
                        note = Description of Artificial Sequence: Synthetic peptide
MOD_RES                 2
                        note = D-amino acid
MOD_RES                 5
                        note = D-amino acid
source                  1..9
                        mol_type = protein
                        organism = synthetic construct
SEQUENCE: 37
MPFRWFKPV                                                                        9

SEQ ID NO: 38           moltype = AA  length = 9
FEATURE                 Location/Qualifiers
REGION                  1..9
                        note = Description of Artificial Sequence: Synthetic peptide
MOD_RES                 2..5
                        note = D-amino acid
source                  1..9
                        mol_type = protein
                        organism = synthetic construct
SEQUENCE: 38
MPFRWFKPV                                                                        9
```

```
SEQ ID NO: 39          moltype = AA   length = 9
FEATURE                Location/Qualifiers
REGION                 1..9
                       note = Description of Artificial Sequence: Synthetic peptide
MOD_RES                2
                       note = D-amino acid
MOD_RES                4..5
                       note = D-amino acid
source                 1..9
                       mol_type = protein
                       organism = synthetic construct
SEQUENCE: 39
MPFRWFKPV                                                                         9

SEQ ID NO: 40          moltype = AA   length = 9
FEATURE                Location/Qualifiers
REGION                 1..9
                       note = Description of Artificial Sequence: Synthetic peptide
MOD_RES                2..3
                       note = D-amino acid
MOD_RES                5
                       note = D-amino acid
source                 1..9
                       mol_type = protein
                       organism = synthetic construct
SEQUENCE: 40
ALFRWFKPV                                                                         9

SEQ ID NO: 41          moltype = AA   length = 9
FEATURE                Location/Qualifiers
REGION                 1..9
                       note = Description of Artificial Sequence: Synthetic peptide
MOD_RES                2
                       note = D-amino acid
MOD_RES                5
                       note = D-amino acid
source                 1..9
                       mol_type = protein
                       organism = synthetic construct
SEQUENCE: 41
ALFRWFKPV                                                                         9

SEQ ID NO: 42          moltype = AA   length = 9
FEATURE                Location/Qualifiers
REGION                 1..9
                       note = Description of Artificial Sequence: Synthetic peptide
MOD_RES                2..5
                       note = D-amino acid
source                 1..9
                       mol_type = protein
                       organism = synthetic construct
SEQUENCE: 42
ALFRWFKPV                                                                         9

SEQ ID NO: 43          moltype = AA   length = 9
FEATURE                Location/Qualifiers
REGION                 1..9
                       note = Description of Artificial Sequence: Synthetic peptide
MOD_RES                2
                       note = D-amino acid
MOD_RES                4..5
                       note = D-amino acid
source                 1..9
                       mol_type = protein
                       organism = synthetic construct
SEQUENCE: 43
ALFRWFKPV                                                                         9

SEQ ID NO: 44          moltype = AA   length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 44
DPCASAFCRF FRSACYARVL SLNC                                                       24
```

```
SEQ ID NO: 45          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 45
DPCASAYCRF FRSACYARVL SLNC                                                24

SEQ ID NO: 46          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 46
DPCVSAYCRF FRSACYARVL SLNC                                                24

SEQ ID NO: 47          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 47
DPCATAYCRF FRSACYARVL SLNC                                                24

SEQ ID NO: 48          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 48
DPCASAYCRF FRSACYAKVL SLNC                                                24

SEQ ID NO: 49          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 49
DPCATKYCRF FRSACYERVL SLNC                                                24

SEQ ID NO: 50          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 50
DPCASKYCRF FRSACYERVL SLNC                                                24

SEQ ID NO: 51          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 51
DPCASEYCRF FRSACYKRVL SLNC                                                24

SEQ ID NO: 52          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
```

```
SEQUENCE: 52
DPCVSEYCRF FRSACYKRVL SLNC                                                   24

SEQ ID NO: 53           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 53
DPCVSKYCRF FRSACYERVL SLNC                                                   24

SEQ ID NO: 54           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 54
DPCATEYCRF FRSACYKRVL SLNC                                                   24

SEQ ID NO: 55           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 55
DPCASKYCRF FRSACYERVL SLNC                                                   24

SEQ ID NO: 56           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 56
DPCASEYCRF FRSACYKRVL SLNC                                                   24

SEQ ID NO: 57           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 57
DPCATEYCRF FRSACYKRVL SLNC                                                   24

SEQ ID NO: 58           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 58
DPCATKYCRF FRSACYERVL SLNC                                                   24

SEQ ID NO: 59           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 59
DPCVTKYCRF FRSACYERVL SLNC                                                   24

SEQ ID NO: 60           moltype = AA  length = 24
FEATURE                 Location/Qualifiers
REGION                  1..24
                        note = Description of Artificial Sequence: Synthetic peptide
```

```
source                  1..24
                        mol_type = protein
                        organism = synthetic construct
SEQUENCE: 60
DPCVSEYCRF FRSACYKRVL SLNC                                            24

SEQ ID NO: 61           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 61
CADPCATAYC RFFRSACYCR VLSLNC                                          26

SEQ ID NO: 62           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 62
CADPCVSAYC RFFRSACYCR VLSLNC                                          26

SEQ ID NO: 63           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 63
CADPCVTAYC RFFRSACYCR VLSLNC                                          26

SEQ ID NO: 64           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 64
CADPCASAYC RFFRSACYCR VLSLNC                                          26

SEQ ID NO: 65           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 65
CADPCASAYC RFFRSACYCK VLSLNC                                          26

SEQ ID NO: 66           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 66
CRFFRSAC                                                              8

SEQ ID NO: 67           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 67
CKFFRSAC                                                              8
```

-continued

```
SEQ ID NO: 68          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 68
CRFFRSGC                                                                     8

SEQ ID NO: 69          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 69
CRFFRSVC                                                                     8

SEQ ID NO: 70          moltype = AA  length = 8
FEATURE                Location/Qualifiers
REGION                 1..8
                       note = Description of Artificial Sequence: Synthetic peptide
MOD_RES                8
                       note = D-amino acid
source                 1..8
                       mol_type = protein
                       organism = synthetic construct
SEQUENCE: 70
PRFFRSVP                                                                     8

SEQ ID NO: 71          moltype = AA  length = 8
FEATURE                Location/Qualifiers
REGION                 1..8
                       note = Description of Artificial Sequence: Synthetic peptide
MOD_RES                8
                       note = D-amino acid
source                 1..8
                       mol_type = protein
                       organism = synthetic construct
SEQUENCE: 71
PRFFRSGP                                                                     8

SEQ ID NO: 72          moltype = AA  length = 8
FEATURE                Location/Qualifiers
REGION                 1..8
                       note = Description of Artificial Sequence: Synthetic peptide
MOD_RES                8
                       note = D-amino acid
source                 1..8
                       mol_type = protein
                       organism = synthetic construct
SEQUENCE: 72
PRFFRSAP                                                                     8

SEQ ID NO: 73          moltype = AA  length = 8
FEATURE                Location/Qualifiers
REGION                 1..8
                       note = Description of Artificial Sequence: Synthetic peptide
MOD_RES                8
                       note = D-amino acid
source                 1..8
                       mol_type = protein
                       organism = synthetic construct
SEQUENCE: 73
PKFFRSAP                                                                     8

SEQ ID NO: 74          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 74
YCRFFRSACY                                                                  10
```

| | |
|---|---|
| SEQ ID NO: 75<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 75<br>FCRFFRSACF | 10 |
| SEQ ID NO: 76<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 76<br>WCRFFRSACW | 10 |
| SEQ ID NO: 77<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 77<br>YCRFFRSVCY | 10 |
| SEQ ID NO: 78<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 78<br>YCKFFRSACY | 10 |
| SEQ ID NO: 79<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 79<br>QCRFFRSACS | 10 |
| SEQ ID NO: 80<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 80<br>NCRFFRSACS | 10 |
| SEQ ID NO: 81<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 81<br>QCRFFRSACT | 10 |
| SEQ ID NO: 82<br>FEATURE<br>REGION<br>source | moltype = AA length = 10<br>Location/Qualifiers<br>1..10<br>note = Description of Artificial Sequence: Synthetic peptide<br>1..10<br>mol_type = protein<br>organism = synthetic construct |
| SEQUENCE: 82<br>NCRFFRSACT | 10 |

```
SEQ ID NO: 83           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 83
QCKFFRSACS                                                                        10

SEQ ID NO: 84           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 84
GFCKFFRSAC FG                                                                     12

SEQ ID NO: 85           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 85
GYCRFFRSAC YG                                                                     12

SEQ ID NO: 86           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 86
GFCRFFRSAC FG                                                                     12

SEQ ID NO: 87           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 87
GFCRFFRSAC YG                                                                     12

SEQ ID NO: 88           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 88
GYCRFFRSAC FG                                                                     12

SEQ ID NO: 89           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 89
GYCKFFRSAC YG                                                                     12

SEQ ID NO: 90           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
```

```
SEQUENCE: 90
GYCRFFRSVC YG                                                          12

SEQ ID NO: 91          moltype = AA   length = 132
FEATURE                Location/Qualifiers
source                 1..132
                       mol_type = protein
                       organism = Homo sapiens
SEQUENCE: 91
MDVTRLLLAT LLVFLCFFTA NSHLPPEEKL RDDRSLRSNS SVNLLDVPSV SIVALNKKSK       60
QIGRKAAEKK RSSKKEASMK KVVRPRTPLS APCVATRNSC KPPAPACCDP CASCQCRFFR      120
SACSCRVLSL NC                                                         132

SEQ ID NO: 92          moltype = AA   length = 110
FEATURE                Location/Qualifiers
source                 1..110
                       mol_type = protein
                       organism = Homo sapiens
SEQUENCE: 92
HLPPEEKLRD DRSLRSNSSV NLLDVPSVSI VALNKKSKQI GRKAAEKKRS SKKEASMKKV       60
VRPRTPLSAP CVATRNSCKP PAPACCDPCA SCQCRFFRSA CSCRVLSLNC                 110

SEQ ID NO: 93          moltype = AA   length = 53
FEATURE                Location/Qualifiers
REGION                 1..53
                       note = Description of Artificial Sequence: Synthetic
                        polypeptide
source                 1..53
                       mol_type = protein
                       organism = synthetic construct
SEQUENCE: 93
KKVVRPRTPL SAPCVATRNS CKPPAPACCD PCASCYCRFF RSACYCRVLS LNC              53

SEQ ID NO: 94          moltype = AA   length = 40
FEATURE                Location/Qualifiers
REGION                 1..40
                       note = Description of Artificial Sequence: Synthetic
                        polypeptide
source                 1..40
                       mol_type = protein
                       organism = synthetic construct
SEQUENCE: 94
CVATRNSCKP PAPACCDPCA SCYCRFFRSA CYCRVKSLNC                             40
```

PEPTIDES AND METHODS FOR REDUCING SKIN PIGMENTATION

CROSS-REFERENCE

This application is a continuation of International Patent Application No. PCT/US2022/021579, filed Mar. 23, 2022, which claims the benefit of U.S. Provisional Application No. 63/271,646, filed Oct. 25, 2021, and U.S. Provisional Application No. 63/165,611, filed Mar. 24, 2021, each of which is incorporated herein by reference in its entirety.

BACKGROUND OF THE INVENTION

Skin pigmentation occurs by a pathway involving interactions between keratinocytes in the epidermis, and melanocytes in the basal layer of the epidermis. Exposure to UV light causes keratinocytes to release melanocyte-stimulating hormone (MSH). In humans MSH binds to and activates the melanocortin 1 receptor (MC1R) on the plasma membrane of melanocytes. This initiates the MC1R-mediated signaling cascade, which raises melanocyte production of the darkly pigmented melanin known as eumelanin, and increases transfer of melanosomes (small secretable vesicles containing melanin) to keratinocytes. This can result in undesirable skin discoloration, for example, dark spots. There is a need for safe and effective compositions and methods of inhibiting the skin pigmentation pathway to prevent and/or reduce skin discoloration.

SEQUENCE LISTING

The instant application contains a Sequence Listing which has been submitted electronically in XML format and is hereby incorporated by reference in its entirety. Said XML copy, created on Sep. 20, 2023, is named 54780-710.301_SL.xml and is 147,456 bytes in size.

SUMMARY OF THE INVENTION

The present invention includes compositions and methods relating to novel peptide antagonists that inhibit binding of melanocyte-stimulating hormone (MSH) to the melanocortin 1 receptor (MC1R). In some embodiments, the invention includes cosmetic compositions comprising a peptide antagonist of the invention. In some embodiments, the peptide antagonists of the invention are useful in topical cosmetic compositions for preventing, reducing, or both, the appearance of skin discoloration due to pigmentation. In some embodiments, the invention relates to methods of using a cosmetic composition comprising a peptide antagonist of the invention, e.g., to prevent or reduce skin discoloration due to pigmentation in an individual in need thereof. In some embodiments, the invention relates to methods for blocking or inhibiting MSH-MC1R interactions using a composition or method of the invention.

In some aspects, provided herein, is a Group A melanocortin 1 receptor (MC1R) peptide antagonist comprising an amino acid sequence: Xaa1-Xaa2-Xaa3-Xaa4-Xaa5-Xaa6-Xaa7-Xaa8-Xaa9, wherein: Xaa1 is absent or selected from: Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, D-Glu, and a derivative of Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, or D-Glu; Xaa2 is selected from: Pro, D-Pro, Ala, Gly, Val, Leu, Ile, D-Ala, D-Gly, D-Val, D-Leu, D-Ile, and a derivative of Pro, D-Pro, Ala, Gly, Val, Leu, Ile, D-Ala, D-Gly, D-Val, D-Leu, or D-Ile; Xaa3 is selected from: Phe, Trp, Tyr, D-Phe, D-Trp, D-Tyr, and a derivative of Phe, Trp, Tyr, D-Phe, D-Trp or D-Tyr; Xaa4 is selected from: Arg, His, Lys, D-Arg, D-His, D-Lys, and a derivative of Arg, His, Lys, D-Arg, D-His, or D-Lys; Xaa5 is selected from: Phe, Trp, Tyr, D-Phe, D-Trp, D-Tyr, and a derivative of Phe, Trp, Tyr, D-Phe, D-Trp, or D-Tyr; Xaa6 is selected from: Phe, Trp, Tyr, D-Phe, D-Trp, D-Tyr, and a derivative of Phe, Trp, Tyr, D-Phe, D-Trp, or D-Tyr; Xaa7 is selected from: Arg, His, Lys, D-Arg, D-His, D-Lys, and a derivative of Arg, His, Lys, D-Arg, D-His, or D-Lys, Xaa8 is selected from: Pro, D-Pro, and a derivative of Pro or D-Pro; Xaa9 is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile; wherein when Xaa1 is Met, Xaa2 is not Pro; the N-terminus is optionally modified; and the C-terminus is optionally modified. In some embodiments, Xaa2 of the Group A peptide antagonist is selected from: D-Pro, Ala, Gly, Val, Leu, Ile, D-Ala, D-Gly, D-Val, D-Leu, D-Ile, and a derivative of D-Pro, Ala, Gly, Val, Leu, Ile, D-Ala, D-Gly, D-Val, D-Leu, or D-Ile. In some embodiments, Xaa2 of the Group A peptide antagonist is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile. In some embodiments of the, Xaa1 of the Group A peptide antagonist is absent or selected from: Cys, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, D-Glu, and a derivative of Cys, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, or D-Glu. In some embodiments, Xaa1 of the Group A peptide antagonist is absent or selected from: D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, D-Glu, and a derivative of D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, or D-Glu. In some embodiments, Xaa1 of the Group A peptide antagonist is absent or selected from: Cys, Sec, D-Cys, D-Met, D-Sec, D-Ser, D-Thr, Gly, Val, Ile, D-Ala, D-Gly, D-Val, D-Leu, D-Ile, D-Phe, D-Trp, D-Tyr, Asn, Asp, D-Asn, D-Asp, D-Gln, D-Glu, and a derivative of Cys, Sec, D-Cys, D-Met, D-Sec, D-Ser, D-Thr, Gly, Val, Ile, D-Ala, D-Gly, D-Val, D-Leu, D-Ile, D-Phe, D-Trp, D-Tyr, Asn, Asp, D-Asn, D-Asp, D-Gln, or D-Glu. In some embodiments, Xaa2 of the Group A peptide antagonist is selected from: D-Pro, Gly, Val, Ile, D-Ala, D-Gly, D-Val, D-Leu, D-Ile, and a derivative of D-Pro, Gly, Val, Ile, D-Ala, D-Gly, D-Val, D-Leu, D-Ile. In some embodiments, Xaa1 of the Group A peptide antagonist is absent or selected from: Phe, Trp, Tyr, D-Phe, D-Trp, D-Tyr, and a derivative of Phe, Trp, Tyr, D-Phe, D-Trp, or D-Tyr; Xaa2 is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile; Xaa3 is selected from: Phe, Trp, Tyr, D-Phe, D-Trp, D-Tyr, and a derivative of Phe, Trp, Tyr, D-Phe, D-Trp, or D-Tyr; Xaa4 is selected from: Arg, His, Lys, D-Arg, D-His, D-Lys, and a derivative of Arg, His, Lys, D-Arg, D-His, or D-Lys; Xaa5 is selected from: Phe, Trp, Tyr, D-Phe, D-Trp, D-Tyr, and a derivative of Phe, Trp, Tyr, D-Phe, D-Trp, or D-Tyr; Xaa6 is selected from: Phe, Trp, Tyr, D-Phe, D-Trp, D-Tyr, and a derivative of Phe, Trp, Tyr, D-Phe, D-Trp, or D-Tyr; Xaa7 is selected from: Arg, His, Lys, D-Arg, D-His, D-Lys, and a derivative of Arg, His, Lys, D-Arg, D-His, or D-Lys; Xaa8 is selected from: Pro, D-Pro, and a derivative of Pro or D-Pro; and Xaa9 is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile.

In some aspects, provided herein, is a Group B melanocortin 1 receptor (MC1R) peptide antagonist comprising an amino acid sequence Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-Xaa17-Xaa18-Xaa19-Xaa20-Xaa21-Xaa22-Xaa23-Xaa24-Xaa25-Xaa26, wherein: Xaa1 is absent or Xaa1 and Xaa19 form a linkage Xaa1-Xaa19; Xaa2 is absent or selected from: Ala, Gly, Val, Leu, Ile, and a derivative of Ala, Gly, Val, Leu, or Ile; Xaa3 is absent or selected from: Asn, Asp, Gln, Glu, and a derivative of Asn, Asp, Gln, or Glu; Xaa4 is absent or selected from: Pro and a derivative of Pro; Xaa5 is absent or Xaa5 and Xaa26 form a linkage Xaa5-Xaa26; Xaa6 is absent or selected from: Ala, Gly, Val, Leu, Ile, and a derivative of Ala, Gly, Val, Leu, or Ile; Xaa7 is absent or selected from: Cys, Met, Sec, Ser, Thr, and a derivative of Cys, Met, Sec, Ser, or Thr; Xaa8 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19; Xaa9 is absent or selected from: Phe, Trp, Tyr, Asn, Asp, Gln, Glu, and a derivative of Phe, Trp, Tyr, Asn, Asp, Gln, or Glu; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is absent or selected from: Phe, Trp, Tyr, Cys, Met, Sec, Ser, Thr, and a derivative of Phe, Trp, Tyr, Cys, Met, Sec, Ser, or Thr; Xaa19 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19, or Xaa1 and Xaa19 form a linkage Xaa1-Xaa19; Xaa20 is absent or selected from: Arg, His, Lys, and a derivative of Arg, His, or Lys; Xaa21 is absent or selected from: Ala, Gly, Val, Leu, Ile, and a derivative of Ala, Gly, Val, Leu, or Ile; Xaa22 is absent or selected from: Ala, Gly, Val, Leu, Ile, and a derivative of Ala, Gly, Val, Leu, or Ile; Xaa23 is absent or selected from: Cys, Met, Sec, Ser, Thr, and a derivative of Cys, Met, Sec, Ser, Thr; Xaa24 is absent or selected from: Ala, Gly, Val, Leu, Ile, and a derivative of Ala, Gly, Val, Leu, or Ile; Xaa25 is absent or selected from: Asn, Asp, Gln, Glu, and a derivative of Asn, Asp, Gln, or Glu; Xaa26 is absent or Xaa5 and Xaa26 form a linkage Xaa5-Xaa26; the N-terminus is optionally modified; and the C-terminus is optionally modified. In some embodiments, Xaa1 of the Group B antagonist is absent; Xaa2 is absent; Xaa3 is selected from: Asn, Asp, Gln, Glu, and a derivative of Asn, Asp, Gln, or Glu; Xaa4 is selected from: Pro and a derivative of Pro; Xaa5 and Xaa26 form a linkage Xaa5-Xaa26; Xaa6 is selected from: Ala, Gly, Val, Leu, Ile, and a derivative of Ala, Gly, Val, Leu, or Ile; Xaa7 is selected from: Cys, Met, Sec, Ser, Thr, and a derivative of Cys, Met, Sec, Ser, or Thr; Xaa8 is selected from: Ala, Gly, Val, Leu, Ile, and a derivative of Ala, Gly, Val, Leu, or Ile; Xaa9 is selected from: Phe, Trp, Tyr, and a derivative of Phe, Trp, or Tyr; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is selected from: Phe, Trp, Tyr, and a derivative of Phe, Trp, or Tyr; Xaa19 is selected from: Ala, Gly, Val, Leu, Ile, and a derivative of Ala, Gly, Val, Leu, or Ile; Xaa20 is selected from: Arg, His, Lys, and a derivative of Arg, His, or Lys; Xaa21 is selected from: Ala, Gly, Val, Leu, Ile, and a derivative of Ala, Gly, Val, Leu, or Ile; Xaa22 is selected from: Ala, Gly, Val, Leu, Ile, and a derivative of Ala, Gly, Val, Leu, or Ile; Xaa23 is selected from: Cys, Met, Sec, Ser, Thr, and a derivative of Cys, Met, Sec, Ser, Thr; Xaa24 is selected from: Ala, Gly, Val, Leu, Ile, and a derivative of Ala, Gly, Val, Leu, or Ile; and Xaa25 is selected from: Asn, Asp, Gln, Glu, and a derivative of Asn, Asp, Gln, or Glu. In some embodiments, Xaa1 of the Group B antagonist is absent; Xaa2 is absent; Xaa3 is selected from: Asn, Asp, Gln, Glu, and a derivative of Asn, Asp, Gln, or Glu; Xaa4 is selected from: Pro and a derivative of Pro; Xaa5 and Xaa26 form a linkage Xaa5-Xaa26; Xaa6 is selected from: Ala, Gly, Val, Leu, Ile, and a derivative of Ala, Gly, Val, Leu, or Ile; Xaa7 is selected from: Cys, Met, Sec, Ser, Thr, and a derivative of Cys, Met, Sec, Ser, or Thr; Xaa8 and Xaa19 form a linkage Xaa8-Xaa19; Xaa9 is selected from: Phe, Trp, Tyr, and a derivative of Phe, Trp, or Tyr; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is selected from: Phe, Trp, Tyr, and a derivative of Phe, Trp, or Tyr; Xaa20 is selected from: Arg, His, Lys, and a derivative of Arg, His, or Lys; Xaa21 is selected from: Ala, Gly, Val, Leu, Ile, and a derivative of Ala, Gly, Val, Leu, or Ile; Xaa22 is selected from: Ala, Gly, Val, Leu, Ile, and a derivative of Ala, Gly, Val, Leu, or Ile; Xaa23 is selected from: Cys, Met, Sec, Ser, Thr, and a derivative of Cys, Met, Sec, Ser, Thr; Xaa24 is selected from: Ala, Gly, Val, Leu, Ile, and a derivative of Ala, Gly, Val, Leu, or Ile; and Xaa25 is selected from: Asn, Asp, Gln, Glu, and a derivative of Asn, Asp, Gln, or Glu. In some embodiments, Xaa1 and Xaa19 of the Group B antagonist form a linkage Xaa1-Xaa19; Xaa2 is selected from: Ala, Gly, Val, Leu, Ile, and a derivative of Ala, Gly, Val, Leu, or Ile; Xaa3 is selected from: Asn, Asp, Gln, Glu, and a derivative of Asn, Asp, Gln, or Glu; Xaa4 is selected from: Pro and a derivative of Pro; Xaa5 and Xaa26 form a linkage Xaa5-Xaa26; Xaa6 is selected from: Ala, Gly, Val, Leu, Ile, and a derivative of Ala, Gly, Val, Leu, or Ile; Xaa7 selected from: Cys, Met, Sec, Ser, Thr, and a derivative of Cys, Met, Sec, Ser, or Thr; Xaa8 selected from: Ala, Gly, Val, Leu, Ile, and a derivative of Ala, Gly, Val, Leu, or Ile; Xaa9 is selected from: Phe, Trp, Tyr, and a derivative of Phe, Trp, or Tyr; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is selected from: Phe, Trp, Tyr, and a derivative of Phe, Trp, or Tyr; Xaa20 is selected from: Arg, His, Lys, and a derivative of Arg, His, or Lys; Xaa21 is selected from: Ala, Gly, Val, Leu, Ile, and a derivative of Ala, Gly, Val, Leu, or Ile; Xaa22 is selected from: Ala, Gly, Val, Leu, Ile, and a derivative of Ala, Gly, Val, Leu, or Ile; Xaa23 is selected from: Cys, Met, Sec, Ser, Thr, and a derivative of Cys, Met, Sec, Ser, Thr; Xaa24 is selected from: Ala, Gly, Val, Leu, Ile, and a derivative of Ala, Gly, Val, Leu, or Ile; and Xaa25 is selected from: Asn, Asp, Gln, Glu, and a derivative of Asn, Asp, Gln, or Glu. In some embodiments, Xaa1 of the Group B antagonist is absent; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; and Xaa18-Xaa26 are absent. In some embodiments, Xaa1-Xaa8 of the Group B antagonist are absent; Xaa1-Xaa8 are absent; Xaa9 is selected from: Phe, Trp, Tyr, Asn, Asp, Gln, Glu, and a derivative of Phe, Trp, Tyr, Asn, Asp, Gln, or Glu; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is selected from: Phe, Trp, Tyr, and a derivative of Phe, Trp, or Tyr; and Xaa19-Xaa26 are absent. In some embodiments, Xaa1-Xaa7 of the Group B antagonist are absent; Xaa8 and Xaa19 form a linkage Xaa8-Xaa19; Xaa9 is selected from: Phe, Trp, Tyr, and a derivative of Phe, Trp, or Tyr; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is selected from: Phe, Trp, Tyr, and a derivative of Phe, Trp, or Tyr; and Xaa20-Xaa26 are absent. In some embodiments, Xaa1-Xaa8 of the Group B antagonist are absent, Xaa9 is absent or selected from: Phe, Trp, Tyr, Asn, Asp, Gln, Glu, and a derivative of Phe, Trp, Tyr, Asn, Asp, Gln, or Glu; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, Thr; Xaa16 is selected from: Ala, Gly, Val, Leu, Ile, and a derivative of Ala, Gly, Val, Leu, or Ile; Xaa18 is absent or selected from: Cys, Met, Sec, Ser, Thr, Phe, Trp, Tyr, and a derivative of Cys, Met, Sec, Ser, Thr, Phe, Trp, or Tyr; and Xaa19-Xaa26 are absent.

In some aspects, provided herein, is a melanocortin 1 receptor peptide antagonist comprising an amino acid sequence set forth as any of SEQ ID NOS: 4-90. In some embodiments, the N-terminal and C-terminal modifications are as shown for these peptides in Tables 1 and 2. In some embodiments, the N-terminal and C-terminal modifications are selected from any known in the art or described herein.

In some aspects, provided herein, is an MC1R peptide antagonist wherein the MC1R peptide antagonist amino acid sequence consists of a Group A or Group B MC1R peptide antagonist amino acid sequence as described herein, including but not limited to any one of SEQ ID NOS: 4-90. In some aspects, provided herein, is an MC1R peptide antagonist wherein the MC1R peptide antagonist amino acid sequence consists of an isolated Group A or Group B MC1R peptide antagonist amino acid sequence as described herein, including but not limited to any one of SEQ ID NOS: 4-90.

In some embodiments, each linkage in an MC1R peptide antagonist is independently selected from: a Cys-Cys linkage, a Sec-Sec linkage, a cystathionine linkage, a lactam bridge, a Gly-Gly linkage, a thioether linkage, a dicarba linkage; and a diproline linkage selected from Pro-Pro, D-Pro-D-Pro, D-Pro-Pro, and Pro-D-Pro, in the amino to carboxy-terminal direction. In some embodiments, a linkage has a spatial separation between the alpha carbons or the geometric center of each amino acid residue of about 3.5 to about 10 angstroms, wherein the linkage has a spatial separation between the alpha carbons or the geometric centers of each of residue of about 3.5 to about 10 angstroms, or both. In some embodiments, the N-terminus of an MC1R peptide antagonist is modified to $C_1$-$C_6$ acyl, $C_1$-$C_5$ alkyl, $C_6$-$C_{12}$ aralkyl, $C_5$-$C_{10}$ aryl, $C_4$-$C_8$ heteroaryl, formyl, or a lipid. In some embodiments, the C-terminus of an MC1R peptide antagonist is modified to comprise $NH_2$, amino-acyl, amino-$C_1$-$C_5$ alkyl, amino-$C_6$-$C_{12}$-aralkyl, amino-$C_5$-$C_{10}$ aryl, amino-$C_4$-$C_8$ heteroaryl, or O—($C_1$-$C_5$ alkyl). In some embodiments, the N-terminus is not modified with an amino acid or a derivative of an amino acid, and the C-terminus is not modified with an amino acid or a derivative of an amino acid. In some embodiments, a lipid is covalently attached to a cysteine, serine, lysine, threonine or tyrosine of the MC1R peptide antagonist. In some embodiments, wherein a lipid is covalently attached to an amino acid residue of the MC1R peptide antagonist, the lipid comprises a $C_6$-$C_{20}$ alkyl, $C_6$-$C_{20}$ alkenyl, $C_6$-$C_{20}$ alkynyl, or $C_6$-$C_{20}$ acyl group. In some embodiments, the lipid comprises a geranyl, farnesyl, or geranylgeranyl group. In some embodiments, the lipid comprises a undecyloyl, lauroyl, tridecyloyl, myristoyl, palmitoyl, or stearoyl group. In some embodiments, the lipid is a covalent modification of Cys added by palmitoylation or prenylation. In some embodiments, the MC1R receptor peptide antagonist comprises at least one derivative that is a non-canonical amino acid selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid. In some embodiments, the aromatic side chain amino acid is a derivative of tyrosine, histidine, tryptophan, or phenylalanine. In some embodiments, the non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine. In some embodiments, the at least one derivative is a non-canonical amino acid selected from the group consisting of: 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and ornithine. In some embodiments, one or more amino acids in the peptides have the D-amino acid configuration and the remaining amino acids in the peptide have the L-amino acid configuration.

In some aspects, the melanocortin 1 receptor peptide antagonist inhibits a melanocortin 1 receptor. In some embodiments, the inhibition is selective. In some embodiments, the inhibition comprises blocking MSH binding to the melanocortin 1 receptor. In some embodiments, the $IC_{50}$ is: about 1 millimolar to about 1 picomolar, less than about 200 nM, less than about 150 nM, less than about 100 nM, less than about 75 nM, less than about 50 nM, or less than about 25 nM. In some embodiments, the melanocortin 1 receptor peptide antagonist inhibits a melanocortin 1 receptor with an increased activity as compared to the activity of a control. In some embodiments, the melanocortin 1 receptor peptide antagonist is a Group A MC1R peptide antagonist, and the control is a peptide having the amino acid sequence of SEQ ID NO: 1. In some embodiments, the melanocortin 1 receptor peptide antagonist has an amino acid sequence of any one of SEQ ID NOS: 4-43, and the control is a peptide having the amino acid sequence set forth as SEQ ID NO: 1. In some embodiments, the melanocortin 1 receptor peptide antagonist is a Group B MC1R peptide antagonist, and the control is a peptide having the amino acid sequence set forth as any one of SEQ ID NOS: 2, 3, 91, 92, 93 and 94. In some embodiments, the melanocortin 1 receptor peptide antagonist has an amino acid sequence of any one of SEQ ID NOS: 44-90, and the control is a peptide having the amino acid sequence set forth as any one of SEQ ID NOS: 2, 3, 91, 92, 93 and 94. In some embodiments, the melanocortin 1 receptor peptide antagonist is a Group A or Group B MC1R peptide antagonist, and the control is a peptide having the amino acid sequence set forth as any one of SEQ ID NOS: 1, 2, 3, 91, 92, 93 and 94. In some embodiments, the melanocortin 1 receptor peptide antagonist inhibits the melanocortin 1 receptor at an $IC_{50}$ of about 0.4 to about 0.8 times the control $IC_{50}$. In some embodiments, the melanocortin 1 receptor peptide antagonist activity is greater than the activity of the control by about 1.25-fold to about 5-fold. In some embodiments, the activity of the melanocortin 1 receptor peptide antagonist and the activity of the control are determined using the same assay method, in the same experiment, or both.

In some aspects, provided herein, is a composition comprising an MC1R peptide antagonist as described herein. In some embodiments, the composition is a cosmetic composition for prevention, reduction, and/or improvement of the appearance of skin discoloration in an individual in need thereof. In some embodiments, the cosmetic composition is formulated for topical use. The skin discoloration can be caused by pigmentation. The skin discoloration can be caused by hyperpigmentation. In some embodiments, the skin discoloration, e.g., pigmentation or hyperpigmentation, comprises melanin hyperpigmentation, chloasma, melasma, age spots, freckles, or a combination thereof.

In some aspects, provided herein, is a method for preventing or improving skin discoloration in an individual, comprising applying an effective amount of cosmetic composition comprising the MC1R peptide antagonist to the skin of the individual. In some aspects, cosmetic composition comprises more than one active ingredient. In some aspects, the cosmetic composition comprises more than one MC1R peptide antagonist of the present disclosure. In some embodiments, the cosmetic composition comprises one or more excipient selected from the group consisting of: water, a buffer, an absorption enhancer, a stability enhancer, diaminobutyroyl benzylamide, diacetate, glycerin, a gum, a hydrophilic colloid or derivative, a cellulosic derivative, an emulsifier, a fatty alcohol, an acrylic derivative, a mineral, a surfactant, a fat, an oil, a preservative, a monosaccharide, a disaccharide, a polysaccharide, a glycosaminoglycan, and a chelating agent. In some embodiments, the absorption enhancer is selected from the group consisting of: a liposome delivery system, a transfersome delivery system, an ethosome delivery system, a short chain alcohol, a long chain alcohol, a polyalcohol, urea, an amino acid, an amino acid ester, an amine, an amide, 1-dodecylazacycloheptan-2-one (AZONE®), a derivative of 1-dodecylazacycloheptan-2-one, a pyrrolidone, a pyrrolidone derivative, a terpene, a terpene derivative, a fatty acid, a fatty acid ester, a macrocyclic compound, a tenside, a sulfoxide, lecithin vesicles, water surfactants, a polyol, a small molecule tri, tetra, penta, hexa, septa or octa peptide, isoceteth-20, ethoxydiglycol, dimethyl sulfoxide, dimethyl isosorbide, and phloretin. In some embodiments, the stability enhancer is a small molecule peptide. In some embodiments, the small molecule peptide is selected from the group consisting of: a tripeptide, a tetrapeptide, a pentapeptide, a hexapeptide, a septapeptide, an octapeptide, Acetyl Hexapeptide-3 Cosmetic Topical Peptide, Melanotan II, ACVR2B (ACE-031), Argireline® Acetate, Argireline, Matrixyl Acetate (palmitoyl pentapeptide), peptide GHK spontaneously complexes with copper, Palmitoyl Tetrapeptide-3, Argireline, Acetyl Glutamyl Heptapeptide, Matrixyl', Snap-8, Syn-Tacks, Syn-Coll, Syn-Hycan, Leuphasyl, Pepha-Tight, T$_{ego}$® Pep 4-17 and Trylagen. In some embodiments, the cosmetic composition further comprises one or more other active ingredient. In some embodiments, the one or more other active ingredient is selected from the group consisting of: a second, different, MC1R peptide antagonist, an antioxidant, a retinoid, a growth factor, a collagen stimulating peptide, a carrier peptide, a peptide that inhibits tTAT-superoxide dismutase, a peptide that inhibits a proteinase, a peptide that stimulates hyaluronan synthase 2, and a keratin-based peptide. In some embodiments, the cosmetic composition comprises a liposome delivery system. In some embodiments, the cosmetic composition is a cream, balm, gel, solution, serum, cosmetic, liquid, lotion, ointment, emulsion, milk, spray, mask, or the like. In some embodiments, the cosmetic composition comprises about 0.01% to about 5% w/w of the MC1R receptor peptide antagonist.

In some aspects, provided herein, is a cosmetic composition comprising the melanocortin 1 receptor peptide antagonist for use in preventing or improving skin discoloration in an individual.

In some aspects, provided herein, the invention includes a method for preventing or temporarily improving the appearance in an individual of skin discoloration caused by pigmentation, comprising applying an effective amount of a cosmetic composition comprising the MC1R receptor peptide antagonist of the disclosure to the individual. In some embodiments, the MC1R receptor peptide antagonist is applied in one or more doses of the cosmetic composition. In some embodiments, a single dose of the cosmetic composition is applied about once per hour to about once per 2 weeks. In some embodiments, a single dose of the cosmetic composition is applied about once per day. In some embodiments, the cosmetic composition can be applied indefinitely with no adverse effect. In some embodiments, the dose of the cosmetic composition is a subimmunological dose.

In some aspects, provided herein, is a lipid vesicle composition comprising: (a) lipid vesicles each comprising a lipid bilayer comprising vesicle forming lipids, (b) an oil-in-water emulsion entrapped in the lipid vesicles, and stabilized by one or more surfactants; (c) a peptide antagonist of a melanocortin 1 receptor entrapped in the lipid bilayer and/or the oil-in-water emulsion. In some embodiments, the peptide antagonist of a melanocortin 1 receptor comprises an amino acid sequence: Xaa1-Xaa2-Xaa3-Xaa4-Xaa5-Xaa6-Xaa7-Xaa8-Xaa9 wherein: Xaa1 is absent or selected from: Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, D-Glu, and a derivative of Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, or D-Glu; Xaa2 is selected from: Pro, D-Pro, Ala, Gly, Val, Leu, Ile, D-Ala, D-Gly, D-Val, D-Leu, D-Ile, and a derivative of Pro, D-Pro, Ala, Gly, Val, Leu, Ile, D-Ala, D-Gly, D-Val, D-Leu, or D-Ile; Xaa3 is selected from: Phe, Trp, Tyr, D-Phe, D-Trp, D-Tyr, and a derivative of Phe, Trp, Tyr, D-Phe, D-Trp, or D-Tyr; Xaa4 is selected from: Arg, His, Lys, D-Arg, D-His, D-Lys, and a derivative of Arg, His, Lys, D-Arg, D-His, or D-Lys; Xaa5 is selected from: Phe, Trp, Tyr, D-Phe, D-Trp, D-Tyr, and a derivative of Phe, Trp, Tyr, D-Phe, D-Trp, or D-Tyr; Xaa6 is selected from: Phe, Trp, Tyr, D-Phe, D-Trp, D-Tyr, and a derivative of Phe, Trp, Tyr, D-Phe, D-Trp, or D-Tyr; Xaa7 is selected from: Arg, His, Lys, D-Arg, D-His, D-Lys, and a derivative of Arg, His, Lys, D-Arg, D-His, or D-Lys; Xaa8 is selected from: Pro, D-Pro, and a derivative of Pro or D-Pro; Xaa9 is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile; wherein when Xaa1 is Met, Xaa2 is not Pro; the N-terminus is optionally modified; and the C-terminus is optionally modified. In some embodiments, the peptide antagonist of a melanocortin 1 receptor comprises an amino acid: Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-Xaa17-Xaa18-Xaa19-Xaa20-Xaa21-Xaa22-Xaa23-Xaa24-Xaa25-Xaa26 wherein: Xaa1 is absent or Xaa1 and Xaa19 form a linkage Xaa1-Xaa19; Xaa2 is absent or selected from: Ala, Gly, Val, Leu, Ile, and a derivative of Ala, Gly, Val, Leu, or Ile; Xaa3 is absent or selected from: Asn, Asp, Gln, Glu, and a derivative of Asn, Asp, Gln, or Glu; Xaa4 is absent or selected from: Pro and a derivative of Pro; Xaa5 is absent or Xaa5 and Xaa26 form a linkage Xaa5-Xaa26; Xaa6 is absent or selected from: Ala, Gly, Val, Leu, Ile, and a derivative of Ala, Gly, Val, Leu, or Ile; Xaa7 is absent or selected from: Cys, Met, Sec, Ser, Thr, and a derivative of Cys, Met, Sec, Ser, or Thr; Xaa8 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19; Xaa9 is absent or selected from: Phe, Trp, Tyr, Asn, Asp, Gln, Glu, and a derivative of Phe, Trp, Tyr, Asn, Asp, Gln, or Glu; Xaa10 and Xaa17 form a linkage Xaa10-Xaa17; Xaa11 is selected from: Arg, His, Lys, and a derivative of Arg, His, or Lys; Xaa12 is selected from: Phe, Trp, Tyr, and a derivative of Phe, Trp, or Tyr; Xaa13 is selected from: Phe, Trp, Tyr, and a derivative of Phe, Trp, or Tyr; Xaa14 is selected from: Arg, His, Lys, and a derivative of Arg, His, or Lys; Xaa15 is selected from: Cys, Met, Sec, Ser, Thr, and a derivative of Cys, Met, Sec, Ser, or Thr; Xaa16 is selected from: Ala, Gly, Val, Leu, Ile, and a derivative of Ala, Gly, Val, Leu, or Ile; Xaa18 is absent or selected from: Phe, Trp, Tyr, Cys, Met, Sec, Ser, Thr, and a derivative of Phe, Trp, Tyr, Cys, Met, Sec, Ser, or Thr; Xaa19 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19, or Xaa1 and Xaa19 form a linkage Xaa1-Xaa19; Xaa20 is absent or selected from: Arg, His, Lys, and a derivative of Arg, His, or Lys; Xaa21 is selected from: Ala, Gly, Val, Leu, Ile, and a derivative of Ala, Gly, Val, Leu, or Ile; Xaa22 is absent or selected from: Ala, Gly, Val, Leu, Ile, and a derivative of Ala, Gly, Val, Leu, or Ile; Xaa23 is absent or selected from: Cys, Met, Sec, Ser, Thr, and a derivative of Cys, Met, Sec, Ser, Thr; Xaa24 is absent or selected from: Ala, Gly, Val, Leu, Ile, and a derivative of Ala, Gly, Val, Leu, or Ile; Xaa25 is absent or selected from: Asn, Asp, Gln, Glu, and a derivative of Asn, Asp, Gln, or Glu; Xaa26 is absent or Xaa5 and Xaa26 form a linkage Xaa5-Xaa26; the N-terminus is optionally modified; and the C-terminus is optionally modified. In some embodiments, the peptide antagonist of a melanocortin 1 receptor comprises an amino acid sequence as set forth as any one of SEQ ID NOS: 4-90. In some embodiments, the peptide antagonist of a melanocortin 1 receptor consists of an amino acid sequence of any one of the amino acid sequences described herein. In some embodiments, the peptide antagonist is present at a concentration of from about 0.1 mg/mL to about 10 mg/mL. In some embodiments, the lipid vesicle composition further comprises one or more penetration enhancing agents. In some embodiments, the one or more penetration enhancing agents comprises a non-ionic surfactant or a combination of non-ionic surfactants. In some embodiments, the non-ionic surfactant or combination of non-ionic surfactants is selected from polyethylene glycol ethers of fatty alcohols, sorbitan esters, polysorbates, sorbitan esters and polyethylene glycol fatty acid esters and combinations thereof. In some embodiments, the polyethylene glycol ethers of fatty alcohols comprise a $C_8$-$C_{22}$ fatty alcohol and a polyethylene glycol group having from about 2 to about 8 ethylene glycol subunits. In some embodiments, the polyethylene glycol ethers of fatty alcohols comprise diethylene glycol hexadecyl ether, 2-(2-octadecoxyethoxy)ethanol, diethylene glycol monooleyl ether, polyoxyethylene (2) oleyl ether, polyoxyethylene (3) oleyl ether, or polyoxyethylene (5) oleyl ether, or any combination thereof. In some embodiments, the sorbitan esters comprise sorbitan monolaurate, sorbitan monopalmitate, sorbitan monostearate, sorbitan monooleate, sorbitan trioleate, sorbitan sesquioleate, or sorbitan isostearate, or any combinations thereof. In some embodiments, the polyethylene glycol fatty acid ester comprises PEG-8 dilaurate, PEG-4 dilaurate, PEG-4 laurate, PEG-8 dioleate, PEG-8 distearate, PEG-8 distearate, PEG-7 glyceryl cocoate, and PEG-20 almond glycerides, or any combination thereof. In some embodiments, the polysorbate comprises polysorbate 20, polysorbate 21, polysorbate 40, polysorbate 60, polysorbate 80, polysorbate 85, or any combination thereof. In some embodiments, each of the non-ionic surfactants has a hydrophobic-lipophilic balance (HLB) of about 10 or less. In some embodiments, the non-ionic surfactant or combination of non-ionic surfactants is present in an amount of from about 0.5% to about to about 10% (w/w) of the composition. In some embodiments, at least one non-ionic surfactant is present in the oil-in-water emulsion. In some embodiments, at least one non-ionic surfactant is present in the lipid bilayer. In some embodiments, the one or more penetration enhancing agents comprises a combination of a sorbitan ester, a polysorbate, and a polyethylene glycol fatty acid esters. In some embodiments, the one or more penetration enhancing agents comprises a combination of a polyethylene glycol ether of a fatty alcohol, a sorbitan esters, and a polysorbate. In some embodiments, the one or more penetration enhancing agents comprises monolauroyllysine or dipalmitoyllysine, or a combination thereof. In some embodiments, the vesicle forming lipids comprise phospholipids, glycolipids, lecithins, ceramides, lysolecithin, lysophosphatidylethanolamine, phosphatidylserine, phosphatidylinositol, sphingomyelin, cardiolipin, phosphatidic acid, cerebroside, or any combination thereof. In some embodiments, the vesicle forming lipids comprise phospholipids. In some embodiments, the composition comprises vesicle forming lipids in an amount of from about 0.5% to about 25% (w/w) of the composition. In some embodiments, the composition comprises a cationic surfactant. In some embodiments, the cationic surfactant is a mono-cationic surfactant. In some embodiments, the cationic surfactant comprises an amino acid and a fatty acid. In some embodiments, the amino acid comprises lysine, arginine, or histidine. In some embodiments, the cationic surfactant is present in an amount of from about 1% to about 20% (w/w) of the composition. In some embodiments, the oil-in-water emulsion comprises a triglyceride in the oil component. In some embodiments, the triglyceride comprises a medium-chain triglyceride. In some embodiments, the triglyceride is present in an amount of from about 1% to about 35% (w/w) of the composition. In some embodiments, the composition comprises a sterol. In some embodiments, the sterol is present in an amount of from about 1% to about 5% (w/w) of the composition. In some embodiments, the composition comprises propylene glycol. In some embodiments, the propylene glycol is present in an amount of from about 1% to about 25% (w/w) of the composition. In some embodiments, the composition comprises one or more viscosity enhancing agents. In some embodiments, the one or more viscosity enhancing agents are present in an amount of from about 0.5% to about 10% (w/w) of the composition. In some embodiments, the composition further comprises one or more additional agents. In some embodiments, the additional agents comprise one or more of a thickener, a preservative, a moisturizer, an emollient, a humectant, an antimicrobial, or any combination thereof. In some embodiments, the composition is formulated for topical application to the skin of a subject. In some embodiments, the composition is formulated to deliver the peptide antagonist to a specified layer of the skin of a subject. In some embodiments, the composition is formulated as a cream, a lotion, a suspension, or an emulsion.

In some aspects, provided herein, is a method of preparing a lipid vesicle composition, the method comprising: a) preparing an oil-in-water emulsion comprising the peptide antagonist of a melanocortin 1 receptor, by mixing oil components of the oil-in-water emulsion with aqueous components of the oil-in-water emulsion, wherein the aqueous components comprise the peptide antagonist of a melanocortin 1 receptor, wherein the oil components and/or the aqueous components of the oil-in-water emulsion comprises the one or more surfactants; b) solubilizing vesicle forming lipids in an acceptable solvent other than water; c) adding the oil-in-water emulsion to the solubilized vesicle forming lipids; and d) mixing the oil-in-water emulsion and the solubilized vesicle forming lipids under mixing conditions effective to form the lipid vesicles comprising a lipid bilayer comprising vesicle forming lipids, and an oil-in-water emulsion entrapped in the lipid vesicles.

In some aspects, provided herein, is a method of preventing or reducing skin discoloration in a subject, the method comprising administering a lipid composition to said subject, wherein the lipid vesicle composition comprises: (a) lipid vesicles each comprising a lipid bilayer comprising vesicle forming lipids, (b) an oil-in-water emulsion entrapped in the lipid vesicles, and stabilized by one or more surfactants; (c) a peptide antagonist of a melanocortin 1 receptor entrapped in the lipid bilayer and/or the oil-in-water emulsion. In some embodiments, the skin discoloration is melanin hyperpigmentation, chloasma, melasma, age spots, freckles, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
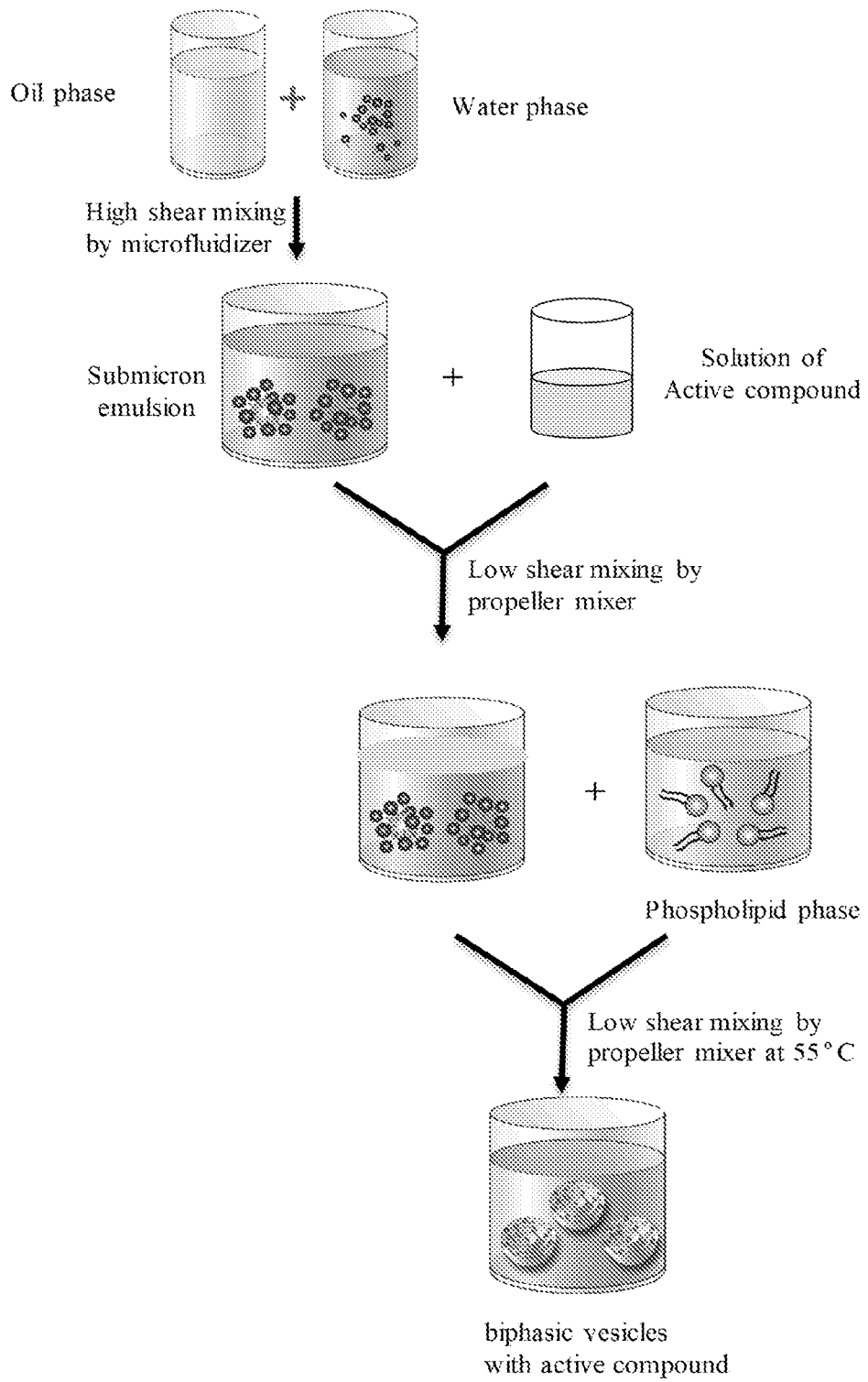
FIG. 1 shows an exemplary pictorial workflow for the preparation of lipid vesicles provided herein.

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of or "consisting of." The phrase "consisting essentially of is used herein to require the specified feature(s) as well as those which do not materially affect the character or function of the claimed invention. As used herein, the term "consisting" is used to indicate the presence of the recited feature alone.

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tent-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, C(O)N($R^a$)$_2$, —N($R^a$)C(O)O$R^a$, —OC(O)—N($R^a$)$_2$, —N($R^a$)C(O)$R^a$, —N($R^a$)C(O)$R^a$ (where t is 1 or 2), —S(O)$_t$O$R^a$(where t is 1 or 2), —S(O)$_t$$R^a$ (where t is 1 or 2) and —S(O)tN($R^a$)$_2$ (where t is 1 or 2) where each $R^a$ independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$ —OC(O)—$R^a$, —N($R^a$)$_2$, —C(O)$R^a$, —C(O)O$R^a$, C(O)N($R^a$)$_2$, —N($R^a$)C(O)O$R^a$, —OC(O)—N($R^a$)$_2$, —N($R^a$)C(O)$R^a$, —N($R^a$)C(O)$R^a$ (where t is 1 or 2), —S(O)$_t$O$R^a$ (where t is 1 or 2), —S(O)$_t$$R^a$ (where t is 1 or 2) and —S(O)tN($R^a$)$_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$ —OC(O)—R$^a$, —N(R$^a$)$_2$, —C(O)R$^a$, —C(O)OR$^a$, C(O)N(R$^a$)$_2$, —N(R$^a$)C(O)OR$^a$, —OC(O)—N(R$^a$)$_2$, —N(R$^a$)C(O)R$^a$, —N(R$^a$)C(O)R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$ —OC(O)—R$^a$, —N(R$^a$)$_2$, —C(O)R$^a$, —C(O)OR$^a$, C(O)N(R$^a$)$_2$, —N(R$^a$)C(O)OR$^a$, —OC(O)—N(R$^a$)$_2$, —N(R$^a$)C(O)R$^a$, —N(R$^a$)C(O)R$^a$ (where t is 1 or 2), —S(O) OR$^a$ (where t is 1 or 2), —S(O) R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$Ra (where t is 1 or 2), —R$^b$—S(O)$_t$Ra (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tRa$ (where t is 1 or 2), —$R^b$—$S(O)_tRa$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tRa$ (where t is 1 or 2), —$R^b$—$S(O) OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$Ra (where t is 1 or 2), —$R^b$—S(O)$_t$Ra (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

The compounds disclosed herein, in some embodiments, contain one or more asymmetric centers and thus give rise to enantiomers, diastereomers, and other stereoisomeric forms that are defined in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para- isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

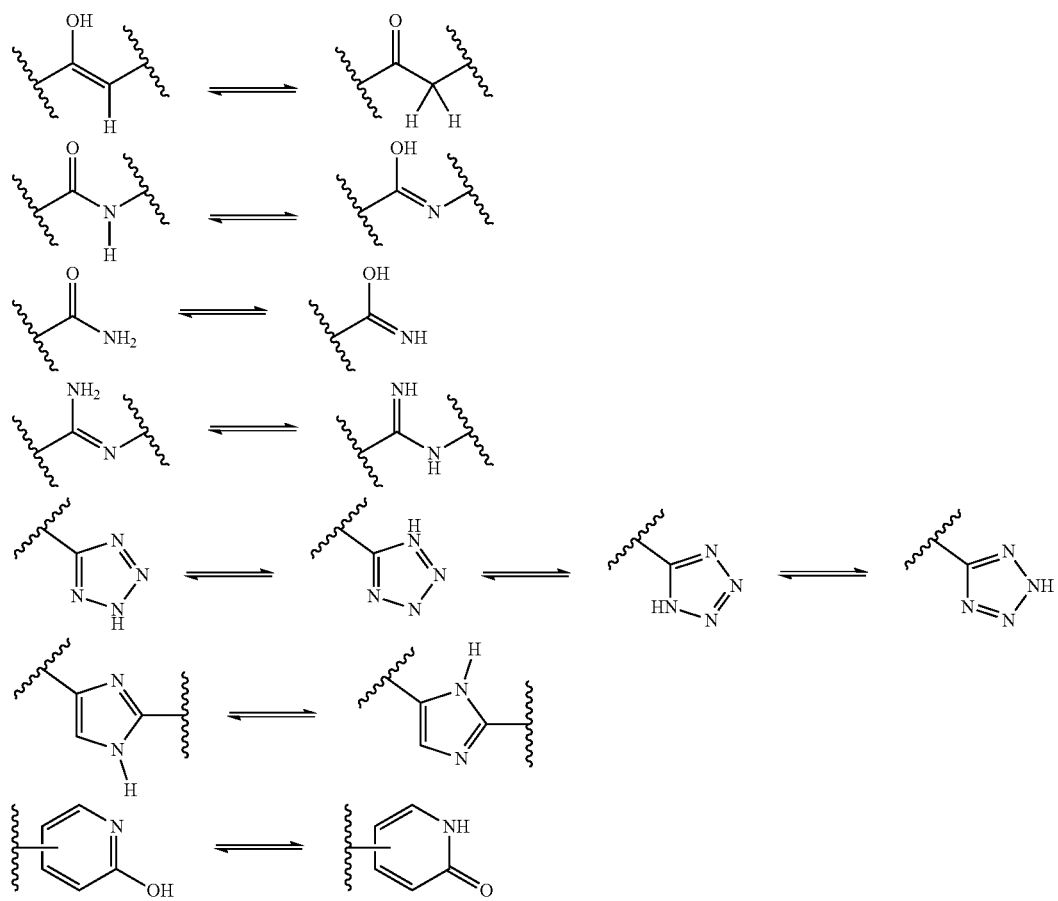

The compounds disclosed herein, in some embodiments, are used in different enriched isotopic forms, e.g., enriched in the content of $^2H$, $^3H$, $^{13}C$, and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium (3H), iodine-125 ($^{125}I$) or carbon-14 ($^{14}C$) Isotopic substitution with $^2H$, $^{11}C$ $^{13}C$, $^{14}C$ $^{15}C$, $^{12}N$ $^{13}N$ $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present disclosure, whether radioactive or not, are encompassed within the scope of the present disclosure.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Raj ender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts. In certain pharmaceutical embodiments of the present disclosure a "pharmaceutically acceptable salt" may be utilized.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal ofPharmaceutical Science, 66:1-19 (1997)). Acid addition salts of basic compounds are, in some embodiments, prepared by contacting the free base forms with a sufficient amount of the desired acid to produce the salt according to methods and techniques with which a skilled artisan is familiar. In certain pharmaceutical embodiments of the present disclosure a "pharmaceutically acceptable acid addition salt" may be utilized.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra. In certain pharmaceutical embodiments of the present disclosure a "pharmaceutically acceptable base addition salt" may be utilized.

As used herein, "treatment of or "treating," "applying," "palliating," or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder or condition being treated. Also, a therapeutic benefit is achieved with the eradication or amelioration of one or more of the physiological symptoms associated with the underlying disorder or condition such that an improvement is observed in the patient, notwithstanding that the patient is still afflicted with the underlying disorder or condition. For prophylactic benefit, the compositions are, in some embodiments, administered to a patient at risk of developing a particular disorder or condition, or to a patient reporting one or more of the physiological symptoms of a disorder or condition, even though a diagnosis of this disorder or condition has not been made. In certain pharmaceutical embodiments of the present disclosure the terms "treatment of or "treating," "applying," "palliating," or "ameliorating" may be utilized.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). In certain pharmaceutical embodiments of the present disclosure the terms "prodrug" may be utilized.

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

As used herein, "conservative substitution" means an exchange of one amino acid for another amino acid with similar properties, such as size, charge, and polarity. The substitution can be for a natural or modified (e.g., unnatural amino acid). Non-limiting of examples which can be interchanged in conservative substitutions include the following groupings: Large Hydrophobics (Valine, Leucine, Isoleucine, Phenylalanine, Tryptophan, Tyrosine, Methionine), Small Non-Polar (Alanine, Glycine), Polar (Serine, Threonine, Glutamine, Asparagine, Cysteine, histidine), Positively Charged (Lysine, Arginine), and Negatively Charged (Glutamate, Aspartate).

When a % is used herein to refer to an amount of a component, unless otherwise specified, it is intended that the % be the % w/w.

The term "penetration enhancing agents" and "penetration enhancers" are used herein interchangeably. As used herein, it refers to one or more ingredients which facilitate or increase the penetration of one or more active ingredients (e.g., anionic polymeric materials such as hyaluronic acid or peptide antagonists) through one or more layers of the skin of a subject. In some embodiments, the penetration enhancing agent is a surfactant, including, for example, non-ionic surfactants having a hydrophilic-lipophilic balance (HLB) of about 10 or less, a cationic group, or another agent such as a terpene, alkaloid, salicylate derivative, nicotinate derivative, or any combination thereof.

The term "multisome" as used herein refers lipid vesicle (such as a biphasic lipid vesicle) which comprises one or more penetration enhancers, which in preferred embodiments include multiple penetration enhancers which work in a synergistic fashion. In some embodiments, multisomes include vesicle whose central core compartments are occupied by an oil-in-water emulsion composed of an aqueous continuous phase and a dispersed hydrophobic, hydrophilic or oil phase. In an embodiment, the spaces between adjacent bilayers of lipid vesicles may also be occupied by the emulsion.

The term "lipid vesicle composition" as used herein refers to a composition which includes one or more lipid vesicles (e.g., multisomal lipid vesicles, lipid bilayer vesicles, etc.). When a lipid vesicle composition is described as "comprising" one or more additional components (e.g., an anionic polymer material or a peptide antagonist provided herein), it is intended that the composition includes the additional component in any manner within the composition (e.g., encapsulated within a lipid vesicle. For example, a lipid vesicle composition comprising an anionic polymer material can include the anionic polymer material encapsulated within a lipid bilayer of the lipid vesicle composition.

The term "emulsion" as used herein refers to a mixture of two immiscible substances.

The term "bilayer" as used herein refers to a structure composed of amphiphilic lipid molecules arranged in two molecular layers, with the hydrophobic tails on the interior and the polar head groups on the exterior surfaces.

The term "topical administration" or "topical delivery" as used herein means intradermal, transdermal and/or transmucosal delivery of a compound by administration of a composition comprising the compound or compounds to skin and/or a mucosal membrane.

The term "gemini surfactant" as used herein refers to a surfactant molecule which contains more than one hydrophobic tail, and each hydrophobic tail having a hydrophilic head wherein he hydrophobic tails or hydrophilic heads are linked together by a spacer moiety. The hydrophobic tails can be identical or differ. Likewise, the hydrophilic heads can be identical or differ. the hydrophilic heads may be anionic, cationic, or neutral.

The term "HLB" or "Hydrophilic-Lipophilic Balance" value refers to standard HLB according to Griffin, J. Soc. Cosm. Chem., vol. 5, 249 (1954), which indicates the degrees of hydrophilicity and lipophilicity of a surfactant.

Melanocortin 1 Receptor (MC1R)

The present disclosure relates to peptide antagonists of Melanocortin 1 Receptor, a 317 amino acid G protein coupled receptor found on melanocyte plasma membrane, also referred to as MC1R. MC1R has 7 a-helical transmembrane domains with a DRY (Asp-Arg-Tyr) motif at the junction of the third transmembrane domain, an intracellular C-terminus with a palmitoylation site, and an extracellular N-terminus with an N-linked glycosylation site. Three intracellular loops and three extracellular loops are formed by its insertion in the membrane. The extracellular and transmembrane domains interact with MC1R ligands. Intracellular and transmembrane domains regulate signaling, including adenylyl cyclase interactions. (See, e.g., Wolf Horrell, 2016, Frontiers in Genetics 7(95): 1-16, incorporated herein by reference.)

MC1R binds pituitary hormones including Adrenocorticotropic hormone (ACTH) and alpha-MSH ($\alpha$-MSH), which is a non-selective agonist of melanocortin receptors (MCR-1, 3, 4, and 5). Upon binding by $\alpha$-MSH, MC1R is activated to cause melanocytes to switch from generating yellow/red phaeomelanin (default) to brown/black eumelanin.

In the adaptive pigmentation pathway, the $\alpha$-melanocyte-stimulating hormone ($\alpha$-MSH) is produced in response to UV radiation damage of epidermal keratinocytes. The $\alpha$-MSH binds to MC1R on the melanocyte surface, signaling an increase in melanin pigment synthesis. $\alpha$-MSH agonism of MC1R raises melanocyte production of eumelanin, which is darkly pigmented, and increases transfer of melanosomes containing eumelanin to keratinocytes. While dark pigment can protect the individual from UV exposure and further damage, excessive pigmentation is often undesirable.

The peptide antagonists of the disclosure bind in the active site of MC1R, blocking the binding of $\alpha$-MSH to MC1R and ultimately resulting in decreased production of eumelanin and decreased melanin deposition in the epidermis.

Peptide Antagonists of the Melanocortin 1 Receptor

The present disclosure provides peptide antagonists of MC1R, and compositions thereof. In some embodiments, a peptide antagonist of the disclosure has a desirable property, or an improved property relative to an MC1R antagonist known in the art. Such a property can include, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist). In some embodiments, a formulation containing a peptide antagonist of the disclosure has a desirable property, or an improved property relative to a formulation containing an MC1R antagonist known in the art. In some embodiments, a desirable or improved property of a formulation of the disclosure is a property relating to the use of the formulation for an indication as described elsewhere herein, e.g., use for reducing or improving the appearance of skin discoloration.

Group A MC1R Peptide Antagonists

In some embodiments, an MC1R peptide antagonist of the disclosure is a Group A MC1R peptide antagonist, also referred to herein as a Group A peptide antagonist. In some embodiments, a Group A MC1R peptide antagonist of the disclosure has 8-9 amino acid residues and comprises or consists of the amino acid sequence:

```
Xaa1-Xaa2-Xaa3-Xaa4-Xaa5-Xaa6-Xaa7-Xaa8-Xaa9
``` wherein:
Xaa1 is absent or selected from: Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, D-Glu, and a derivative of Cys, Met, Sec, Ser, Thr, D-Cys, D-Met, D-Sec, D-Ser, D-Thr, Ala, Gly, Val, Leu, Ile, D-Ala, D-Gly, D-Val, D-Leu, D-Ile, Phe, Trp, Tyr, D-Phe, D-Trp, D-Tyr, Asn, Asp, Gln, Glu, D-Asn, D-Asp, D-Gln, or D-Glu;

Xaa2 is selected from: Pro, D-Pro, Ala, Gly, Val, Leu, Ile, D-Ala, D-Gly, D-Val, D-Leu, D-Ile, and a derivative of Pro, D-Pro, Ala, Gly, Val, Leu, Ile, D-Ala, D-Gly, D-Val, D-Leu, or D-Ile;

Xaa3 is selected from: Phe, Trp, Tyr, D-Phe, D-Trp, D-Tyr, and a derivative of Phe, Trp, Tyr, D-Phe, D-Trp, or D-Tyr;

Xaa4 is selected from: Arg, His, Lys, D-Arg, D-His, D-Lys, and a derivative of Arg, His, Lys, D-Arg, D-His, or D-Lys;

Xaa5 is selected from: Phe, Trp, Tyr, D-Phe, D-Trp, D-Tyr, and a derivative of Phe, Trp, Tyr, D-Phe, D-Trp, or D-Tyr;

Xaa6 is selected from: Phe, Trp, Tyr, D-Phe, D-Trp, D-Tyr, and a derivative of Phe, Trp, Tyr, D-Phe, D-Trp, or D-Tyr;

Xaa7 is selected from: Arg, His, Lys, D-Arg, D-His, D-Lys, and a derivative of Arg, His, Lys, D-Arg, D-His, or D-Lys;

Xaa8 is selected from: Pro, D-Pro, and a derivative of Pro or D-Pro;

Xaa9 is selected from: Ala, Gly, Val, Leu, Ile, D-Ala, D-Gly, D-Val, D-Leu, D-Ile, and a derivative of Ala, Gly, Val, Leu, Ile, D-Ala, D-Gly, D-Val, D-Leu, or D-Ile;

the N-terminus is optionally modified; and
the C-terminus is optionally modified.

In some embodiments, the peptide antagonist of the disclosure does not consist of the following amino acid sequence:

```
(Melanostatine-5, or Nonapeptide-1)
                              (SEQ ID NO: 1)
Met-Pro-D-Phe-Arg-D-Trp-Phe-Lys-Pro-Val.
```

In some embodiments, the number of amino acid residues in a Group A peptide antagonist of the disclosure is not more than 8 or not more than 9. In embodiments, a Group A peptide antagonist of the disclosure consists of 8 or 9 amino acid residues.

Non-limiting examples of amino acid sequences of Group A peptide antagonists of the disclosure are shown in Table 1. In some embodiments, a Group A MC1R peptide antagonist of the disclosure comprises or consists of an amino acid sequence set forth in Table 1. An MC1R peptide antagonist described herein, including those set forth in Table 1 and Table 2, may comprise or consist of the disclosed amino acid sequence having amino and/or carboxy terminal modifications other than those shown

TABLE 1

Group A MC1R Peptide Antagonist Examples (Xaa1-Xaa9)

| SEQ ID NO | SEQUENCE |
|---|---|
| 4 | Met-Val-dPhe-dArg-dTrp-Phe-Lys-Pro-Val-$NH_2$ |
| 5 | Met-Val-dPhe-dArg-Trp-Phe-Lys-Pro-Val-$NH_2$ |
| 6 | Met-Val-dPhe-dArg-dTrp-Phe-Arg-Pro-Val-$NH_2$ |
| 7 | Met-Val-dPhe-dArg-Trp-Phe-Arg-Pro-Val-$NH_2$ |
| 8 | Met-Val-dPhe-Arg-dTrp-Phe-Lys-Pro-Val-$NH_2$ |
| 9 | Met-Val-dPhe-Arg-dTrp-Phe-Arg-Pro-Val-$NH_2$ |
| 10 | Ala-Val-dPhe-dArg-Trp-Phe-Arg-Pro-Val-$NH_2$ |
| 11 | Ala-Val-dPhe-Arg-dTrp-Phe-Lys-Pro-Val-$NH_2$ |
| 12 | Ala-Val-dPhe-dArg-dTrp-Phe-Lys-Pro-Val-$NH_2$ |
| 13 | Ala-Val-dPhe-dArg-Trp-Phe-Lys-Pro-Val-$NH_2$ |
| 14 | Ala-Val-dPhe-dArg-dTrp-Phe-Arg-Pro-Val-$NH_2$ |
| 15 | Phe-Val-dPhe-dArg-dTrp-Phe-Arg-Pro-Val-$NH_2$ |
| 16 | Phe-Val-dPhe-Arg-dTrp-Phe-Lys-Pro-Val-$NH_2$ |
| 17 | Phe-Val-dPhe-dArg-dTrp-Phe-Lys-Pro-Val-$NH_2$ |
| 18 | Phe-Val-dPhe-dArg-Trp-Phe-Lys-Pro-Val-$NH_2$ |
| 19 | Phe-Val-dPhe-Arg-dTrp-Phe-Lys-Pro-Ala-$NH_2$ |
| 20 | Val-Pro-dPhe-Arg-dTrp-Phe-Lys-Pro-Val-$NH_2$ |
| 21 | Val-Val-dPhe-Arg-dTrp-Phe-Lys-Pro-Val-$NH_2$ |
| 22 | Val-dPro-dPhe-Arg-dTrp-Phe-Lys-Pro-Val-$NH_2$ |
| 23 | Val-Pro-dPhe-Arg-dTrp-Phe-Arg-Pro-Val-$NH_2$ |
| 24 | Glu-Pro-dPhe-Arg-dTrp-Phe-Lys-Pro-Val-$NH_2$ |
| 25 | Glu-Val-dPhe-Arg-dTrp-Phe-Lys-Pro-Val-$NH_2$ |
| 26 | Glu-Val-dPhe-Arg-dTrp-Phe-Arg-Pro-Val-$NH_2$ |
| 27 | Met-Val-Phe-Arg-dTrp-Phe-Lys-Pro-Val-$NH_2$ |
| 28 | Met-Val-Phe-dArg-dTrp-Phe-Lys-Pro-Val-$NH_2$ |
| 29 | Met-Val-Phe-Arg-dTrp-Phe-Arg-Pro-Val-$NH_2$ |
| 30 | Met-Val-Phe-Arg-dTrp-Phe-Lys-Pro-Ala-$NH_2$ |
| 31 | Ile-Phe-dArg-dTrp-Phe-Lys-Pro-Val-$NH_2$ |
| 32 | Ile-Phe-Arg-dTrp-Phe-Lys-Pro-Val-$NH_2$ |
| 33 | Ile-dPhe-Arg-dTrp-Phe-Lys-Pro-Val-$NH_2$ |
| 34 | Ile-dPhe-dArg-dTrp-Phe-Lys-Pro-Val-$NH_2$ |
| 35 | Met-Val-dPhe-dArg-dTrp-Phe-Lys-Pro-Val-$NH_2$ |
| 36 | Met-dPro-dPhe-Arg-dTrp-Phe-Lys-Pro-Val-$NH_2$ |
| 37 | Met-dPro-Phe-Arg-dTrp-Phe-Lys-Pro-Val-$NH_2$ |
| 38 | Met-dPro-dPhe-dArg-dTrp-Phe-Lys-Pro-Val-$NH_2$ |
| 39 | Met-dPro-Phe-dArg-dTrp-Phe-Lys-Pro-Val-$NH_2$ |
| 40 | Ala-dLeu-dPhe-Arg-dTrp-Phe-Lys-Pro-Val-$NH_2$ |
| 41 | Ala-dLeu-Phe-Arg-dTrp-Phe-Lys-Pro-Val-$NH_2$ |

TABLE 1-continued

Group A MC1R Peptide Antagonist Examples (Xaa1-Xaa9)

| SEQ ID NO | SEQUENCE |
|---|---|
| 42 | Ala-dLeu-dPhe-dArg-dTrp-Phe-Lys-Pro-Val-NH$_2$ |
| 43 | Ala-dLeu-Phe-dArg-dTrp-Phe-Lys-Pro-Val-NH$_2$ |

In some embodiments, SEQ ID NOs 16 or 32 have a lower IC$_{50}$ value using a competition assay compared to a reference (e.g., SEQ ID NO 1). In some embodiments, the IC$_{50}$ value is about 70 nM to about 160 nM. In some embodiments, the IC$_{50}$ value is about 70 nM to about 75 nM, about 70 nM to about 80 nM, about 70 nM to about 85 nM, about 70 nM to about 90 nM, about 70 nM to about 100 nM, about 70 nM to about 110 nM, about 70 nM to about 120 nM, about 70 nM to about 130 nM, about 70 nM to about 140 nM, about 70 nM to about 150 nM, about 70 nM to about 160 nM, about 75 nM to about 80 nM, about 75 nM to about 85 nM, about 75 nM to about 90 nM, about 75 nM to about 100 nM, about 75 nM to about 110 nM, about 75 nM to about 120 nM, about 75 nM to about 130 nM, about 75 nM to about 140 nM, about 75 nM to about 150 nM, about 75 nM to about 160 nM, about 80 nM to about 85 nM, about 80 nM to about 90 nM, about 80 nM to about 100 nM, about 80 nM to about 110 nM, about 80 nM to about 120 nM, about 80 nM to about 130 nM, about 80 nM to about 140 nM, about 80 nM to about 150 nM, about 80 nM to about 160 nM, about 85 nM to about 90 nM, about 85 nM to about 100 nM, about 85 nM to about 110 nM, about 85 nM to about 120 nM, about 85 nM to about 130 nM, about 85 nM to about 140 nM, about 85 nM to about 150 nM, about 85 nM to about 160 nM, about 90 nM to about 100 nM, about 90 nM to about 110 nM, about 90 nM to about 120 nM, about 90 nM to about 130 nM, about 90 nM to about 140 nM, about 90 nM to about 150 nM, about 90 nM to about 160 nM, about 100 nM to about 110 nM, about 100 nM to about 120 nM, about 100 nM to about 130 nM, about 100 nM to about 140 nM, about 100 nM to about 150 nM, about 100 nM to about 160 nM, about 110 nM to about 120 nM, about 110 nM to about 130 nM, about 110 nM to about 140 nM, about 110 nM to about 150 nM, about 110 nM to about 160 nM, about 120 nM to about 130 nM, about 120 nM to about 140 nM, about 120 nM to about 150 nM, about 120 nM to about 160 nM, about 130 nM to about 140 nM, about 130 nM to about 150 nM, about 130 nM to about 160 nM, about 140 nM to about 150 nM, about 140 nM to about 160 nM, or about 150 nM to about 160 nM. In some embodiments, the IC$_{50}$ value is about 70 nM, about 75 nM, about 80 nM, about 85 nM, about 90 nM, about 100 nM, about 110 nM, about 120 nM, about 130 nM, about 140 nM, about 150 nM, or about 160 nM. In some embodiments, the IC$_{50}$ value is at least about 70 nM, about 75 nM, about 80 nM, about 85 nM, about 90 nM, about 100 nM, about 110 nM, about 120 nM, about 130 nM, about 140 nM, or about 150 nM. In some embodiments, the IC$_{50}$ value is at most about 75 nM, about 80 nM, about 85 nM, about 90 nM, about 100 nM, about 110 nM, about 120 nM, about 130 nM, about 140 nM, about 150 nM, or about 160 nM.

Group B Peptide Antagonists

In some embodiments, an MC1R peptide antagonist of the disclosure is a Group B MC1R peptide antagonist, also referred to herein as a Group B peptide antagonist. In some embodiments, a Group B peptide antagonist of the disclosure has 8-26 amino acid residues and comprises the amino acid sequence:

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-Xaa17-Xaa18-Xaa19-Xaa20-Xaa21-Xaa22-Xaa23-Xaa24-Xaa25-Xaa26 wherein:

Xaa1 is absent or Xaa1 and Xaa19 form a linkage Xaa1-Xaa19;

Xaa2 is absent or selected from: Ala, Gly, Val, Leu, Ile, and a derivative of Ala, Gly, Val, Leu, or Ile;

Xaa3 is absent or selected from: Asn, Asp, Gln, Glu, and a derivative of Asn, Asp, Gln, or Glu;

Xaa4 is absent or selected from: Pro and a derivative of Pro;

Xaa5 is absent or Xaa5 and Xaa26 form a linkage Xaa5-Xaa26;

Xaa6 is absent or selected from: Ala, Gly, Val, Leu, Ile, and a derivative of Ala, Gly, Val, Leu, or Ile;

Xaa7 is absent or selected from: Cys, Met, Sec, Ser, Thr, and a derivative of Cys, Met, Sec, Ser, or Thr;

Xaa8 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19;

Xaa9 is absent or selected from: Phe, Trp, Tyr, Asn, Asp, Gln, Glu, and a derivative of Phe, Trp, Tyr, Asn, Asp, Gln, or Glu;

Xaa10 and Xaa17 form a linkage Xaa10-Xaa17;

Xaa11 is selected from: Arg, His, Lys, and a derivative of Arg, His, or Lys;

Xaa12 is selected from: Phe, Trp, Tyr, and a derivative of Phe, Trp, or Tyr;

Xaa13 is selected from: Phe, Trp, Tyr, and a derivative of Phe, Trp, or Tyr;

Xaa14 is selected from: Arg, His, Lys, and a derivative of Arg, His, or Lys;

Xaa15 is selected from: Cys, Met, Sec, Ser, Thr, and a derivative of Cys, Met, Sec, Ser, Thr;

Xaa16 is selected from: Ala, Gly, Val, Leu, Ile, and a derivative of Ala, Gly, Val, Leu, or Ile;

Xaa18 is absent or selected from: Phe, Trp, Tyr, Cys, Met, Sec, Ser, Thr, and a derivative of Phe, Trp, Tyr, Cys, Met, Sec, Ser, or Thr;

Xaa19 is absent or selected from: Ala, Gly, Val, Leu, Ile, Arg, His, Lys, Asn, Asp, Gln, Glu, and a derivative of Ala, Gly, Val, Leu, Ile, Arg, His, Lys, Asn, Asp, Gln, or Glu, and/or Xaa8 and Xaa19 form a linkage Xaa8-Xaa19, or Xaa1 and Xaa19 form a linkage Xaa1-Xaa19;

Xaa20 is absent or selected from: Arg, His, Lys, and a derivative of Arg, His, or Lys;

Xaa21 is absent or selected from: Ala, Gly, Val, Leu, Ile, and a derivative of Ala, Gly, Val, Leu, or Ile;

Xaa22 is absent or selected from: Ala, Gly, Val, Leu, Ile, and a derivative of Ala, Gly, Val, Leu, or Ile;

Xaa23 is absent or selected from: Cys, Met, Sec, Ser, Thr, and a derivative of Cys, Met, Sec, Ser, Thr;

Xaa24 is absent or selected from: Ala, Gly, Val, Leu, Ile, and a derivative of Ala, Gly, Val, Leu, or Ile;

Xaa25 is absent or selected from: Asn, Asp, Gln, Glu, and a derivative of Asn, Asp, Gln, or Glu;

Xaa26 is absent or Xaa5 and Xaa26 form a linkage Xaa5-Xaa26;

the N-terminus is optionally modified; and the C-terminus is optionally modified.

In some embodiments, the amino acid sequence of a peptide antagonist of the disclosure does not consist of: Cys-Cys-Asp-Pro-Cys-Ala-Ser-Cys-Gln-Cys-Arg-Phe-Phe-Arg-Ser-Ala-Cys-Ser-Cys-Arg-Val-Leu-Ser-Leu-Asn-Cys (SEQ ID NO: 2) (Agouti Signaling Protein or ASIP-subdomain, residues 107-132 of full-length ASIP (SEQ ID NO: 91)). See, e.g., Wolf Horrell, 2016, cited and incorporated by reference above. Referring to the amino acid numbering of SEQ ID NO: 2, the ASIP-subdomain contains linkages between residues 1 and 19, 5 and 26, and 10 and 17. In some embodiments, the amino acid sequence of a peptide antagonist of the disclosure does not consist of SEQ ID NO: 2 containing a linkage between residues 1 and 19 (also referred to herein in the context of a Group B peptide as "Xaa1-Xaa19" linkage), 5 and 26 (also referred to herein in the context of a Group B peptide as "Xaa5-Xaa26" linkage) and/or 10 and 17 (Group B peptide "Xaa10-Xaa17" linkage).

In some embodiments, the amino acid sequence of a peptide antagonist of the disclosure does not consist of the Agouti Signaling Protein amino acid sequence set forth as SEQ ID NO: 91. (See, e.g., UniProtKB—P42127, incorporated herein by reference.) In some embodiments, the amino acid sequence of a peptide antagonist of the disclosure does not consist of a portion of SEQ ID NO: 91 having: an N-terminus at any one of positions 1-106; a C-terminus at any one of positions 125-132, or both. In some embodiments, the amino acid sequence of a peptide antagonist of the disclosure does not consist of a portion of SEQ ID NO: 91 having: an N-terminus at any one of positions 1-106; a C-terminus at any one of positions 125-132, or both, and containing a linkage between residues 107 and 125, 111 and 132 and/or between residues 116 and 123. In some embodiments, the amino acid sequence of a peptide antagonist of the disclosure does not consist of a portion of SEQ ID NO: 91 selected from: 23-132 (mature ASIP, SEQ ID NO: 92), 80-132, 93-132, and 106-132, each having or not having a linkage between residues 107 and 125, 111 and 132 and/or 116 and 123.

In some embodiments, the amino acid sequence of a peptide antagonist of the disclosure does not consist of: Lys-Lys-Val-Val-Arg-Pro-Arg-Thr-Pro-Leu-Ser-Ala-Pro-Cys-Val-Ala-Thr-Arg-Asn-Ser-Cys-Lys-Pro-Pro-Ala-Pro-Ala-Cys-Cys-Asp-Pro-Cys-Ala-Ser-Cys-Tyr-Cys-Arg-Phe-Phe-Arg-Ser-Ala-Cys-Tyr-Cys-Arg-Val-Leu-Ser-Leu-Asn-Cys (ASIP-YY, SEQ ID NO: 93, which is ASIP 80-132, Q115Y, S124Y). ASIP-YY is described by, e.g., McNulty, et al., 2005, J. Mol. Bio.346:1059-1070, incorporated herein by reference in its entirety. In some embodiments, the amino acid sequence of a peptide antagonist of the disclosure does not consist of a portion of SEQ ID NO: 93 having an N-terminus at any one of positions 1, 2, 3, 4, 5, 6, 7, 8, 9, 10, 11, 12, 13, 14, 15, 16, 17, 18, 19, 20, 21, 22, 23, 24, 25, 26, or 27. In some embodiments, the amino acid sequence of a peptide antagonist of the disclosure does not consist of a sequence selected from a portion of SEQ ID NO: 3 having an N-terminus selected from any one of positions 1, 2, 3, 4, 5, 6, 7, 8, 9, 10, 11, 12, 13, 14, 15, 16, 17, 18, 19, 20, 21, 22, 23, 24, 25, 26, or 27, having or not having a linkage between residues 28 and 46, 32 and 53 and/or 37 and 44. In some embodiments, the amino acid sequence of a peptide antagonist of the disclosure does not consist of ASIP-YY subdomain residues 28-53 of SEQ ID NO: 94, having or not having a linkage between residues 15 and 33, 19 and 40 and/or 22 and 31.

In some embodiments, the amino acid sequence of a peptide antagonist of the disclosure does not consist of: Cys-Cys-Asp-Pro-Cys-Ala-Ser-Cys-Tyr-Cys-Arg-Phe-Phe-Arg-Ser-Ala-Cys-Tyr-Cys-Arg-Val-Leu-Ser-Leu-Asn-Cys (SEQ ID NO: 3) (ASIP-YY subdomain, ASIP-YY residues 2853; corresponding to ASIP residues 107-132). In some embodiments, the amino acid sequence of a peptide antagonist of the disclosure does not consist of SEQ ID NO: 3 and having or not having a linkage between residues 1 and 19, 5 and 26 and/or 10 and 17. In some embodiments, a peptide antagonist of the disclosure does not consist of a sequence selected from a portion of SEQ ID NO: 3 having an N-terminus selected from any one of positions 1, 2, 3, 4, 5, 6, 7, 8, or 9. In some embodiments, a peptide antagonist of the disclosure does not consist of a sequence selected from a portion of SEQ ID NO: 3 having an N-terminus selected from any one of positions 1, 2, 3, 4, 5, 6, 7, 8, or 9, and having or not having a linkage between residues 1 and 19, 5 and 26 and/or 10 and 17.

In some embodiments, the number of amino acid residues in a Group B peptide antagonist of the disclosure is 8, 9, 10, 11, 12, 13, 14, 15, 16, 17, 18, 19, 20, 21, 22, 23, 24, 25 or 26. In some embodiments, the number of amino acid residues in a Group B peptide antagonist of the disclosure is not more than 8, 9, 10, 11, 12, 13, 14, 15, 16, 17, 18, 19, 20, 21, 22, 23, 24, 25 or 26. In some embodiments, the number of amino acid residues in a Group B peptide antagonist of the disclosure is not more than 8, 9, 10, 11, 12, 13, 14, 15, 16, 17, 18, 19, 20, 21, 22, 23, 24, 25 or 26.

Non-limiting examples of amino acid sequences of Group B peptide antagonists of the disclosure are shown in Table 2. In some embodiments, a Group B MC1R peptide antagonist of the disclosure comprises or consists of an amino acid sequence set forth in Table 2.

TABLE 2

Group B MC1R Peptide Antagonist Examples (Xaa1-Xaa26)

| SEQ ID NO | SEQUENCE |
|---|---|
| 44[1,2] | Ac-Asp-Pro-Cys-Ala-Ser-Ala-Phe-Cys-Arg-Phe-Phe-Arg-Ser-Ala-Cys-Tyr-Ala-Arg-Val-Leu-Ser-Leu-Asn-Cys |
| 45[1,2] AL1 | Ac-Asp-Pro-Cys-Ala-Ser-Ala-Tyr-Cys-Arg-Phe-Phe-Arg-Ser-Ala-Cys-Tyr-Ala-Arg-Val-Leu-Ser-Leu-Asn-Cys |

TABLE 2-continued

Group B MC1R Peptide Antagonist Examples (Xaa1-Xaa26)

| SEQ ID NO | SEQUENCE |
| --- | --- |
| 46[1,2] | Ac-Asp-Pro-Cys-Val-Ser-Ala-Tyr-Cys-Arg-Phe-Phe-Arg-Ser-Ala-Cys-Tyr-Ala-Arg-Val-Leu-Ser-Leu-Asn-Cys |
| 47[1,2] | Ac-Asp-Pro-Cys-Ala-Thr-Ala-Tyr-Cys-Arg-Phe-Phe-Arg-Ser-Ala-Cys-Tyr-Ala-Arg-Val-Leu-Ser-Leu-Asn-Cys |
| 48[1,2] | Ac-Asp-Pro-Cys-Ala-Ser-Ala-Tyr-Cys-Arg-Phe-Phe-Arg-Ser-Ala-Cys-Tyr-Ala-Lys-Val-Leu-Ser-Leu-Asn-Cys |
| 49[1,2] | Ac-Asp-Pro-Cys-Ala-Thr-Lys-Tyr-Cys-Arg-Phe-Phe-Arg-Ser-Ala-Cys-Tyr-Glu-Arg-Val-Leu-Ser-Leu-Asn-Cys |
| 50[1,2] | Ac-Asp-Pro-Cys-Ala-Ser-Lys-Tyr-Cys-Arg-Phe-Phe-Arg-Ser-Ala-Cys-Tyr-Glu-Arg-Val-Leu-Ser-Leu-Asn-Cys |
| 51[1,2] | Ac-Asp-Pro-Cys-Ala-Ser-Glu-Tyr-Cys-Arg-Phe-Phe-Arg-Ser-Ala-Cys-Tyr-Lys-Arg-Val-Leu-Ser-Leu-Asn-Cys |
| 52[1,2] | Ac-Asp-Pro-Cys-Val-Ser-Glu-Tyr-Cys-Arg-Phe-Phe-Arg-Ser-Ala-Cys-Tyr-Lys-Arg-Val-Leu-Ser-Leu-Asn-Cys |
| 53[1,2] | Ac-Asp-Pro-Cys-Val-Ser-Lys-Tyr-Cys-Arg-Phe-Phe-Arg-Ser-Ala-Cys-Tyr-Glu-Arg-Val-Leu-Ser-Leu-Asn-Cys |
| 54[1,2] | Ac-Asp-Pro-Cys-Ala-Thr-Glu-Tyr-Cys-Arg-Phe-Phe-Arg-Ser-Ala-Cys-Tyr-Lys-Arg-Val-Leu-Ser-Leu-Asn-Cys |
| 55[1,2,4] | Ac-Asp-Pro-Cys-Ala-Ser-Lys-Tyr-Cys-Arg-Phe-Phe-Arg-Ser-Ala-Cys-Tyr-Glu-Arg-Val-Leu-Ser-Leu-Asn-Cys |
| 56[1,2,4] | Ac-Asp-Pro-Cys-Ala-Ser-Glu-Tyr-Cys-Arg-Phe-Phe-Arg-Ser-Ala-Cys-Tyr-Lys-Arg-Val-Leu-Ser-Leu-Asn-Cys |
| 57[1,2,4] | Ac-Asp-Pro-Cys-Ala-Thr-Glu-Tyr-Cys-Arg-Phe-Phe-Arg-Ser-Ala-Cys-Tyr-Lys-Arg-Val-Leu-Ser-Leu-Asn-Cys |
| 58[1,2,4] | Ac-Asp-Pro-Cys-Ala-Thr-Lys-Tyr-Cys-Arg-Phe-Phe-Arg-Ser-Ala-Cys-Tyr-Glu-Arg-Val-Leu-Ser-Leu-Asn-Cys |
| 59[1,2,4] | Ac-Asp-Pro-Cys-Val-Thr-Lys-Tyr-Cys-Arg-Phe-Phe-Arg-Ser-Ala-Cys-Tyr-Glu-Arg-Val-Leu-Ser-Leu-Asn-Cys |
| 60[1,2,4] | Ac-Asp-Pro-Cys-Val-Ser-Glu-Tyr-Cys-Arg-Phe-Phe-Arg-Ser-Ala-Cys-Tyr-Lys-Arg-Val-Leu-Ser-Leu-Asn-Cys |
| 61[1,2,3] | Cys-Ala-Asp-Pro-Cys-Ala-Thr-Ala-Tyr-Cys-Arg-Phe-Phe-Arg-Ser-Ala-Cys-Tyr-Cys-Arg-Val-Leu-Ser-Leu-Asn-Cys |
| 62[1,2,3] | Cys-Ala-Asp-Pro-Cys-Val-Ser-Ala-Tyr-Cys-Arg-Phe-Phe-Arg-Ser-Ala-Cys-Tyr-Cys-Arg-Val-Leu-Ser-Leu-Asn-Cys |
| 63[1,2,3] | Cys-Ala-Asp-Pro-Cys-Val-Thr-Ala-Tyr-Cys-Arg-Phe-Phe-Arg-Ser-Ala-Cys-Tyr-Cys-Arg-Val-Leu-Ser-Leu-Asn-Cys |
| 64[1,2,3] | Cys-Ala-Asp-Pro-Cys-Ala-Ser-Ala-Tyr-Cys-Arg-Phe-Phe-Arg-Ser-Ala-Cys-Tyr-Cys-Arg-Val-Leu-Ser-Leu-Asn-Cys |
| 65[1,2,3] | Cys-Ala-Asp-Pro-Cys-Ala-Ser-Ala-Tyr-Cys-Arg-Phe-Phe-Arg-Ser-Ala-Cys-Tyr-Cys-Lys-Val-Leu-Ser-Leu-Asn-Cys |
| 66[2] | Ac-Cys-Arg-Phe-Phe-Arg-Ser-Ala-Cys-NH2 |
| 67[2] | Ac-Cys-Lys-Phe-Phe-Arg-Ser-Ala-Cys-NH$_2$ |
| 68[2] | Ac-Cys-Arg-Phe-Phe-Arg-Ser-Gly-Cys-NH2 |
| 69[2] | Ac-Cys-Arg-Phe-Phe-Arg-Ser-Val-Cys-NH2 |
| 70[5] | Pro-Arg-Phe-Phe-Arg-Ser-Val-dPro |
| 71[5] | Pro-Arg-Phe-Phe-Arg-Ser-Gly-dPro |
| 72[5] | Pro-Arg-Phe-Phe-Arg-Ser-Ala-dPro |
| 73[5] | Pro-Lys-Phe-Phe-Arg-Ser-Ala-dPro |

TABLE 2-continued

Group B MC1R Peptide Antagonist Examples (Xaa1-Xaa26)

| SEQ ID NO | SEQUENCE |
|---|---|
| 74[2] | Ac-Tyr-Cys-Arg-Phe-Phe-Arg-Ser-Ala-Cys-Tyr-NH$_2$ |
| 75[2] | Ac-Phe-Cys-Arg-Phe-Phe-Arg-Ser-Ala-Cys-Phe-NH$_2$ |
| 76[2] | Ac-Trp-Cys-Arg-Phe-Phe-Arg-Ser-Ala-Cys-Trp-NH$_2$ |
| 77[2] | Ac-Tyr-Cys-Arg-Phe-Phe-Arg-Ser-Val-Cys-Tyr-NH$_2$ |
| 78[2] | Ac-Tyr-Cys-Lys-Phe-Phe-Arg-Ser-Ala-Cys-Tyr-NH$_2$ |
| 79[2] | Ac-Gln-Cys-Arg-Phe-Phe-Arg-Ser-Ala-Cys-Ser-NH$_2$ |
| 80[2] | Ac-Asn-Cys-Arg-Phe-Phe-Arg-Ser-Ala-Cys-Ser-NH2 |
| 81[2] | Ac-Gln-Cys-Arg-Phe-Phe-Arg-Ser-Ala-Cys-Thr-NH$_2$ |
| 82[2] | Ac-Asn-Cys-Arg-Phe-Phe-Arg-Ser-Ala-Cys-Thr-NH$_2$ |
| 83[2] | Ac-Gln-Cys-Lys-Phe-Phe-Arg-Ser-Ala-Cys-Ser-NH2 |
| 84[2] | Ac-Gly-Phe-Cys-Lys-Phe-Phe-Arg-Ser-Ala-Cys-Phe-Gly-NH2 |
| 85[2,6] | Ac-Gly-Tyr-Cys-Arg-Phe-Phe-Arg-Ser-Ala-Cys-Tyr-Gly-NH2 |
| 86[2,6] | Gly-Phe-Cys-Arg-Phe-Phe-Arg-Ser-Ala-Cys-Phe-Gly |
| 87[2,6] | Gly-Phe-Cys-Arg-Phe-Phe-Arg-Ser-Ala-Cys-Tyr-Gly |
| 88[2,6] | Gly-Tyr-Cys-Arg-Phe-Phe-Arg-Ser-Ala-Cys-Phe-Gly |
| 89[2,6] | Gly-Tyr-Cys-Lys-Phe-Phe-Arg-Ser-Ala-Cys-Tyr-Gly |
| 90[2,6] | Gly-Tyr-Cys-Arg-Phe-Phe-Arg-Ser-Val-Cys-Tyr-Gly |

[1]Comprises a disulfide (Cys-Cys) linkage at (Xaa5-Xaa26);
[2]comprises a disulfide (Cys-Cys) linkage at (Xaa10-Xaa17);
[3]comprises a disulfide (Cys-Cys) linkage at (Xaa1-Xaa19);
[4]comprises a lactam bridge at (Xaa8-Xaa19) (see bold font);
[5]comprises a diproline linkage at (Xaa10-Xaa17);
[6]comprises a glycine-glycine head to tail linkage at (Xaa8-Xaa19);
all numbering referring to Xaa1-Xaa26 numbering of Group B peptides (with absent positions not indicated in table).

A peptide of the disclosure, including those listed in Table 1 and Table 2, can comprise L-amino acids, D-amino acids, or a combination thereof. L-amino acids are indicated by no additional designation, e.g., as in "Pro," or by an upper or lower case L, with or without punctuation, e.g., "L-" as in "L-Pro", "(L)" as in "(L)Pro," etc. D-amino acids are indicated by an upper or lower case D, with or without punctuation, e.g., "D-" as in "D-Pro", "(d)" as in "(d)Pro, "d" as in "dPro," etc.

Amino Acid Substitutions

In any embodiment herein, a substitution of an amino acid is made at one or more positions as desired.

Amino acids can be classified based on chemical and structural properties of their sidechains, for example, naturally-occurring amino acids can be classified as hydrophobic (norleucine, Met, Ala, Val, Leu, and Ile), neutral hydrophilic (Cys, Ser, Thr, Asn, and Gln), acidic (Asp and Glu), basic (His, Lys, and Arg), chain orienting (Gly and Pro), and aromatic (Trp, Tyr, and Phe).

In some embodiments, a conservative amino acid substitution is made by substituting an amino acid of one of the above classes with a different member of that class. In some embodiments, conservative substitutions encompass non-naturally occurring amino acid residues, including peptidomimetics and other reversed or inverted forms of amino acid moieties.

In some embodiments, a non-conservative substitution is made by substituting an amino acid of one of the above classes with a member of a different class.

In some embodiments, substitution takes into account the hydropathic index of an amino acid (see, e.g., Kyte et al., 1982, J. Mol. Biol. 157:105-131, incorporated herein by reference). The hydropathic profile of a peptide can be calculated by giving each amino acid a numerical value, or hydropathy index, and repetitively averaging these values along the peptide chain. In such embodiments, each amino acid is assigned a hydropathic index based on hydrophobicity and charge characteristics. In some embodiments, the hydropathic indices used are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In some embodiments, an amino acid is substituted with a different amino acid having a hydropathic index within 0.1 to 0.5 of the original amino acid. In some embodiments, the hydropathic index is within 0.1, 0.2, 0.3, 0.4, or 0.5 of the original amino acid.

In some embodiments, amino acid substitutions are be made based on hydrophilicity. In some embodiments, the hydrophilicity values used are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (1.3); valine (−1.5); leucine (−1.8); isoleucine (−1.8); tyrosine (−2.3); phenylalanine (−2.5) and tryptophan (−3.4).

In some embodiments, an amino acid is substituted with a different amino acid having a hydrophilicity value within 0.1 to 0.5 of the original amino acid. In some embodiments, the hydrophilicity value is within 0.1, 0.2, 0.3, 0.4, or 0.5 of the original amino acid.

In some embodiments, an amino acid is substituted as shown in the table below. In some embodiments, an amino acid is replaced with a conservative substitution as set forth in Table 3(I), or a derivative (also referred to as an analog herein) of a conservative substitution. In some embodiments, an amino acid is replaced with an alternative substitution as set forth in Table 3(II), showing each full list of alternatives for each amino acid, or a derivative of an alternative substitution.

TABLE 3

Amino Acid Substitutions

| Amino Acid | I. Conservative Substitution | II. Alternative Substitution |
|---|---|---|
| Ala | Gly, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Arg | His, Lys | any basic amino acid or derivative thereof (Arg, His, Lys) any charged amino acid or derivative thereof (Asp, Arg, Glu, Lys) any charged amino acid with an electrically charged sidechain or derivative thereof (Arg, His, Lys) |
| Asn | Asp, Gln, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) |
| Asp | Asn, Gln, Glu | any acidic amino acid or derivative thereof, or any amide of any acidic amino acid or derivative thereof (Asn, Asp, Gln, Glu) any charged amino acid or derivative thereof (Asp, Arg, Glu, Lys) any polar neutral amino acid or derivative thereof (Asp, Cys, Gln, Ser, Thr) any acidic amino acid with an electrically charged sidechain or derivative thereof (Asp, Glu) |
| Cys | Met, Sec, Ser, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |

TABLE 3-continued

Amino Acid Substitutions

| Amino Acid | I. Conservative Substitution | II. Alternative Substitution |
|---|---|---|
| Gln | Asn, Asp, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) any polar neutral amino acid or derivative thereof (Asp, Cys, Gln, Ser, Thr) any acidic amino acid with an electrically charged sidechain or derivative thereof (Asp, Glu) |
| Glu | Asn, Asp, Gln | any acidic amino acid or derivative thereof, or any amide of any acidic amino acid or derivative thereof (Asn, Asp, Gln, Glu) any charged amino acid or derivative thereof (Asp, Arg, Glu, Lys) |
| Gly | Ala, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| His | Arg, Lys | any basic amino acid or derivative thereof (Arg, His, Lys) any polar amino acid or derivative thereof (Asn, Cys, Gln, His, Ser, Thr, Trp, Tyr) any basic amino acid with an electrically charged sidechain or derivative thereof (Arg, His, Lys) |
| Ile | Ala, Gly, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Leu | Ala, Gly, Ile, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Lys | Arg, His | any basic amino acid or derivative thereof (Arg, His, Lys) any charged amino acid or derivative thereof (Asp, Arg, Glu, Lys) any basic amino acid with an electrically charged sidechain or derivative thereof (Arg, His, Lys) |
| Met | Cys, Sec, Ser, Thr | any hydroxyl or sulfur/selenium-containing amino acid or derivative thereof (Cys, Sec, Ser, Met, Thr) any hydrophobic amino acid or derivative thereof (Ala, Gly, Ile, Leu, Met, Phe, Pro, Val) |

TABLE 3-continued

Amino Acid Substitutions

| Amino Acid | I. Conservative Substitution | II. Alternative Substitution |
|---|---|---|
| Phe | Trp, Tyr | any aromatic amino acid or derivative thereof (Phe, Trp, Tyr) any hydrophobic amino acid or derivative thereof (Ala, Gly, Ile, Leu, Met, Phe, Pro, Val) |
| Pro | | any cyclic amino acid or derivative thereof (Pro) any hydrophobic amino acid or derivative thereof (Ala, Gly, Ile, Leu, Met, Phe, Pro, Val) |
| Ser | Cys, Met, Sec, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Thr | Cys, Met, Sec, Ser | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Trp | Phe, Tyr, | any aromatic amino acid or derivative thereof (Phe, Trp, Tyr) any polar amino acid or derivative thereof (Asn, Cys, Gln, His, Ser, Thr, Trp, Tyr) |
| Tyr | Phe, Trp | any aromatic amino acid or derivative thereof (Phe, Trp, Tyr) any polar amino acid or derivative thereof (Asn, Cys, Gln, His, Ser, Thr, Trp, Tyr) |
| Val | Ala, Gly, Ile, Leu | any aliphatic amino acid or derivative thereof (Ala, Gly, Ile, Leu, Val) any hydrophobic amino acid or derivative thereof (Ala, Gly, Ile, Leu, Met, Phe, Pro, Val) |

Constraining Structures

In some embodiments, the peptide antagonist of the present disclosure comprises a constraining structure including, but not limited to, a linkage, bridge or any means of ligation between residues at two positions. In some embodiments, the peptide is constrained by its ends or at positions within the peptide, or both. In some embodiments, the constraining structure influences a peptide antagonist property, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist). In certain embodiments, the constraining structure enhances stability of the peptide antagonist. In certain embodiments, the constraining structure enhances permeability through the skin of the peptide antagonist. In certain embodiments, the constraining structure enhances solubility in a formulation, e.g., a topical formulation, of the peptide antagonist.

In embodiments, a peptide antagonist that is constrained as described herein is referred to as a macrocyclic peptide or structure. A macrocyclic peptide refers to a closed-ring structure of a linear peptide intramolecularly formed by linkage between two positions in the peptide, referred to as linkage amino acids, linkage amino acid derivatives, linkage molecule, linkage moiety, linkage residue, linkage entity, or the like, as appropriate. The two linkage amino acids, linkage amino acid derivatives, linkage molecules, linkage moieties, linkage residues, or linkage entities are separated from each other by two or more amino acid residues, bound to each other directly, bound via a linker, or the like.

In embodiments, a linkage of a peptide antagonist of the disclosure is formed by two linkage amino acids, linkage amino acid derivatives, linkage molecules, linkage moieties, linkage residues, or linkage entities bound to each other by, e.g., a disulfide bond, a peptide bond, an alkyl bond, an alkenyl bond, an ester bond, a thioester bond, an ether bond, a thioether bond, a phosphonate ether bond, an azo bond, a C—S—C bond, a C=N—C bond, a C=N—C bond, an amide bond, a lactam bridge, a carbamoyl bond, an urea bond, a thiourea bond, an amine bond, a thioamide bond, or the like. The macrocyclization may be formed by a bond between an N-terminal amino acid and a C-terminal amino acid of a peptide, by a bond between a terminal amino acid and a non-terminal amino acid, or by a bond between non-terminal amino acids.

For convenience, reference to a specific amino acid involved in a linkage can use the nomenclature for the unlinked amino acid (e.g., the structure it may have prior to formation of a linkage). It is also understood that certain linkages, e.g., synthetic linkages, may not be formed by connecting two amino acids or derivatives as commonly referenced in the art. Therefore, references to linked amino acids herein may use the most closely approximating language to describe each involved chemical entity at a given residue position in the peptide antagonist. Correspondingly, linked entities in the peptide sequence, e.g., Group B amino acids Xaa5 and Xaa26, Xaa10 and Xaa17, Xaa1 and Xaa19, and Xaa8 and Xaa19, may be referred to as linked amino acids, regardless of whether they are amino acids as commonly referenced in the art. In some embodiments, Xaa5, Xaa26, Xaa10, Xaa17, Xaa1, Xaa19, Xaa8, and Xaa19, when linked, e.g, to form linkages Xaa5-Xaa26, Xaa10-Xaa17, Xaa1-Xaa19, and/or Xaa8-Xaa19, can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities in the alternative. These terms can be used to refer to amino acids, molecules, moieties, residues, or entities present at any of Xaa5, Xaa26, Xaa10, Xaa17, Xaa1, Xaa19, Xaa8, and Xaa19, in the alternative, either when linked or unlinked. For example, when not linked but intended to be linked in a peptide antagonist of the disclosure, two linkage amino acids also can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities in the alternative. When linked, two linkage amino acids can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities, in the alternative. When not linked and not intended to be linked, two amino acids can be referred to as unlinked (or non-linkage forming) amino acids, unlinked (or non-linkage forming) amino acid derivatives, unlinked molecules, unlinked moieties, unlinked residues, or unlinked entities. In some embodiments, each residue at a non-linked amino acid position in a peptide antagonist of the disclosure can be referred to as an amino acid, amino acid derivative, molecule, moiety, residue or entity, or as an unlinked (or non-linkage forming) amino acid, unlinked (or non-linkage forming) amino acid derivative, unlinked (or non-linkage forming) molecule, unlinked (or non-linkage forming) moiety, unlinked (or non-linkage forming) residue or unlinked (or non-linkage forming) entity.

Any constraining structure known to those of skill in the art is contemplated for linking the residues. Examples of constraining structures and their respective linkage residues include, but are not limited to linkages or bridges selected from: a disulfide bridge (e.g., a Cys-Cys linkage, wherein each linkage amino acid is a Cys); a Sec-Sec linkage (selenocysteine linkage, wherein each linkage amino acid is a selenocysteine); a cystathionine linkage or bridge (e.g., Ser-Homocysteine linkage), also referred to herein as Cyt-Cyt (e.g., $CH_2$—$CH_2$—S—$CH_2$); a lactam bridge (e.g., Asp-Lys or Glu-Lys linkage), a thioether linkage (e.g., a lanthionine linkage, including but not limited to Cys-dehydroalanine or methyl variant), a diproline linkage, a diglycine linkage, and a dicarba linkage (e.g., a linkage of an olefin-containing amino acid, e.g., allyl glycine or prenyl glycine). In some embodiments, a linkage is selected from: a disulfide bridge having linkage residues Cys-Cys; a selenocysteine linkage having linkage residues Sec-Sec; a cystathionine linkage having linkage residues Ser-Homocysteine; a lactam bridge having residues Asp-Lys or Glu-Lys; a lanthionine linkage having linkage residues Cys-dehydroalanine or a methyl variant, a diproline linkage having linkage residues L-proline, D-proline, or any combination thereof, a diglycine linkage having glycine linkage residues, and a dicarba linkage having linkage residues allyl glycine or prenyl glycine. In embodiments, a linkage amino acid, linkage amino acid derivative, linkage molecule, linkage moiety, linkage residue, or linkage entity is selected from Cys, Sec, Ser, Homocysteine, Asp, Lys, Glu, dehydroalanine, D-Pro, L-Pro, Gly, or an olefin containing amino acid (e.g., allyl glycine or prenyl glycine). In some embodiments, the salt bridge forms between Lys and Glu (amino to carboxy terminal direction) or Glu and Lys (amino to carboxy terminal direction).

In some embodiments, each linkage of a peptide antagonist of the disclosure, e.g., Xaa5-Xaa26, Xaa10-Xaa17, Xaa1-Xaa19, or Xaa8-Xaa19 of a Group B MC1R peptide antagonists, is independently selected from any linkage including any described in the preceding paragraph, including a linkage selected from: a disulfide bridge formed by two Cys linkage residues, a Sec-Sec linkage formed by two selenocysteine linkage residues, a cystathionine linkage formed by Ser and homocysteine linkage residues, a lactam bridge formed by Asp and Lys linkage residues or Glu and Lys linkage residues, a thioether linkage that is a lanthionine linkage formed by Cys and dehydroalanine or methyl variant residues, a diproline linkage, a diglycine linkage, a salt bridge, a dicarba linkage formed by olefin-containing linkage residues, e.g., an allyl glycine or prenyl glycine linkage residue, or any of these linkages formed by linkage residues as known and described in the art. In some embodiments, a peptide antagonist of the disclosure comprises linkages that are the same as one another, or different. A peptide antagonist of the disclosure can be a Group B peptide antagonist comprising one or more linkages between two terminal residues, two non-terminal residues, or between a terminal and a non-terminal residue. A Group B peptide antagonist can comprise linkages (i) Xaa5-Xaa26 and Xaa10-Xaa17, (ii) Xaa5-Xaa26, Xaa10-Xaa17, and Xaa8-Xaa19, (iii) Xaa5-Xaa26, Xaa10-Xaa17, and Xaa1-Xaa19, or (iv) Xaa10-Xaa17. In some embodiments, a Group B peptide antagonist is 24 amino acids in length and comprises linkages Xaa5-Xaa26 and Xaa10-Xaa17. In some embodiments, a Group B peptide antagonist is 24 amino acids in length, comprises linkages at Xaa5-Xaa26 and Xaa10-Xaa17, and Xaa8-Xaa19. In some embodiments, a Group B peptide antagonist is 24 amino acids in length, comprises linkages at Xaa5-Xaa26 and Xaa10-Xaa17, and forms a salt bridge at Xaa8-Xaa19. In some embodiments, the salt bridge forms between Lys and Glu (amino to carboxy terminal direction) or Glu and Lys (amino to carboxy terminal direction). In some embodiments, a Group B peptide antagonist is 24 amino acids in length and comprises linkages at Xaa5-Xaa26 and Xaa10-Xaa17, and Xaa8-Xaa19, wherein Xaa8-Xaa19 is a lactam bridge. In some embodiments, a Group B peptide antagonist is 24 amino acids in length, comprises disulfide linkages at Xaa5-Xaa26 and Xaa10-Xaa17, and forms a salt bridge or a lactam bridge at Xaa8-Xaa19. In some embodiments, a Group B peptide antagonist is 26 amino acids in length and comprises linkages at Xaa5-Xaa26 and Xaa10-Xaa17, and Xaa1-Xaa19. In some embodiments, a Group B peptide antagonist is 26 amino acids in length and comprises disulfide linkages at Xaa5-Xaa26 and Xaa10-Xaa17, and Xaa1-Xaa19. In some embodiments, a Group B peptide antagonist is 8 amino acids in length and comprises a linkage at Xaa10-Xaa17. In some embodiments, a Group B peptide antagonist is 8 amino acids in length and comprises a disulfide linkage at Xaa10-Xaa17. In some embodiments, a Group B peptide antagonist is 8 amino acids in length and comprises a diproline linkage at Xaa10-Xaa17. In some embodiments, a Group B peptide antagonist is 10 amino acids in length and comprises a linkage at Xaa10-Xaa17. In some embodiments, a Group B peptide antagonist is 10 amino acids in length and comprises a disulfide linkage at Xaa10-Xaa17. In some embodiments, a Group B peptide antagonist is 12 amino acids in length and comprises linkages at Xaa10-Xaa17 and Xaa8-Xaa19, wherein Xaa8 and Xaa19 are N-terminal and C-terminal residues, respectively. In some embodiments, a Group B peptide antagonist is 12 amino acids in length and comprises a disulfide linkage at Xaa10-Xaa17 and a linkage between N and C terminal residues Xaa8 and Xaa19. In some embodiments, a Group B peptide antagonist is 12 amino acids in length and comprises a disulfide linkage at Xaa10-Xaa17 and a diglycine linkage between N and C terminal residues Xaa8 and Xaa19. (See, e.g., Knerr et al., 2011, "Synthesis and activity of thioether-containing analogues of the complement inhibitor compstatin," ACS Chem Biol. 6(7): 753-760; DiMarco et al., 2006, "Discovery of novel, highly potent and selective b-hairpin mimetic CXCR4 inhibitors with excellent anti-HIV activity and pharmacokinetic profiles," Bioorganic & Medicinal Chemistry 14: 8396-8404; Dekan et al., 2011, "a-Conotoxin ImI incorporating stable cystathionine bridges maintains full potency and identical three-dimensional structure," J. Am. Chem. Soc. 2011, 133: 15866-15869; Nguyen and Wong, 2017, "Making circles: recent advance in chemical and enzymatic approaches in peptide macrocyclization," Journal of Biochemistry and Chemical Sciences 1(1): 1-13; Tam and Wong, 2012, "Chemical Synthesis of Circular Proteins," The Journal of Biological Chemistry 287 (32): 27020-27025, each incorporated herein by reference in its entirety.) In some embodiments, any appropriate constraining structure resulting from the use of linkage residues as known in the art is contemplated for use in a peptide antagonist of the disclosure.

In some embodiments, a particular constraining structure is selected based on its resistance to degradation, e.g., degradation caused by the reduction of a disulfide bond constraining structure. In some embodiments, the peptide antagonist comprises a constraining structure that resists degradation by reduction. For example, in a reducing environment a disulfide bond may be susceptible to degradation and a resulting loss of activity or other desired peptide antagonist property. In some embodiments, a cystathione linkage or a linkage of at least two $C_1$-$C_6$ heterocycloalkyl rings confers increased stability relative to a disulfide bond.

In some embodiments, two amino acids in a chain are joined by a linkage to create a macrocyclic ring structure. In some embodiments, a linkage mimics a hairpin turn in a peptide. In some embodiments, linkages comprise covalent bonds between canonical or non-canonical amino acids such as cystathionine linkages, lactam bridges, diproline bridges, diglycine bridges, or thioether bridges (e.g., a lanthionine linkage). In some embodiments, linkages comprise noncovalent bonds between canonical or non-canonical amino acids such as salt bridges. In some embodiments, a linkage comprises a dipeptide. In some embodiments, a linkage comprises covalent bonds between canonical or non-canonical acid amino acids such as lanthionine or methyllanthionine linkages. In some embodiments, a linkage comprises at least one aromatic or non-aromatic ring. In some embodiments, a linkage comprises at least one cycloalkyl ring. In some embodiments, a linkage comprises at least one heterocyclic ring. In some embodiments, a linkage comprises at least two heterocyclic rings. In some embodiments, a linkage comprises at least one nitrogen-containing heterocycloalkyl ring.

In some embodiments, a linkage comprises the structure

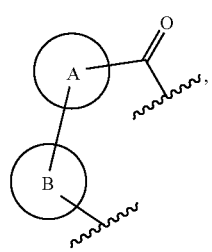

wherein A and B are heterocyclic rings. In some embodiments, a linkage comprises the structure

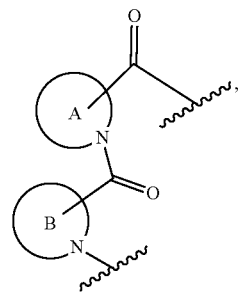

wherein A and B are heterocyclic rings.

In some embodiments, a linkage comprises pyrrolidine, piperidine, dehydropyrrolidine, dehydropiperidine, aziridine, azetidine, oxazolidine, or thiazolidine. In some embodiments, a linkage comprises two $C_1$-$C_6$ heterocycloalkyl rings. In some embodiments, a linkage comprises at least one five-membered heterocycloalkyl ring. In some embodiments, a linkage comprises at least one six-membered heterocycloalkyl ring. In some embodiments, a linkage comprises two five-membered heterocycloalkyl rings. In some embodiments, a linkage comprises two five-membered heterocycloalkyl rings, wherein each ring comprises at least one nitrogen atom. In some embodiments, a linkage comprises two five-membered heterocycloalkyl rings, wherein at least one ring comprises at least one nitrogen atom. In some embodiments, a linkage comprises two six-membered heterocycloalkyl rings. In some embodiments, the linkage comprises two $C_1$-$C_6$ heterocycloalkyl rings connected by an amide bond. In some embodiments, the linkage comprises two $C_1$-$C_6$ heterocycloalkyl rings connected by —C(=O)NH—. In some embodiments, a linkage comprises two pyrrolidine rings. In some embodiments, a linkage comprises at least one non-canonical amino (unnatural) acid residue. In some embodiments, a linkage comprises two amino acids (canonical or non-canonical), wherein a first amino acid has the (S) configuration at the alpha position, and the second amino acid has the (R) configuration at the alpha position. In some embodiments, a linkage comprises two amino acids (canonical or non-canonical) connected by a peptide bond. In some embodiments, a linkage comprises two proline residues (diproline linkage). In some embodiments, a linkage comprises two proline residues connected by a peptide bond. In some embodiments, a linkage comprises a D-proline and an L-proline (D-proline-L-proline or L-proline-D-proline), two D-prolines, or two L-prolines. In some embodiments, the linkage (from N-terminus to C-terminus) comprises L-proline-D-proline. In some embodiments, the linkage (from C-terminus to N-terminus) comprises L-proline-D-proline.

In some embodiments, a linkage comprises a D-proline and an L-proline, or derivatives thereof. In some embodiments, a linkage comprises an L-proline and a proline derivative. In some embodiments, a linkage comprises an L-proline and a proline derivative, wherein the proline derivative has the R configuration. In some embodiments, a linkage comprises an L-proline and a proline derivative, wherein the proline derivative has the S configuration. In some embodiments, a linkage comprises D-proline-D-proline or derivatives thereof. In some embodiments, a linkage comprises L-proline-L-proline or derivatives thereof. In some embodiments, such derivatives comprise substitutions to the pyrrolidine ring of a proline. In some embodiments, a linkage comprises a non-canonical amino acid residue selected from 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline. In some embodiments, a linkage comprises two amino acids selected from proline, 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline.

In some embodiments, a linkage comprises a connection between a C-terminal residue and an N-terminal residue of a peptide to form a macrocyclic structure. In some embodiments, the connection between the C-terminal residue and the N-terminal residue of the peptide is a bond between the N-terminal amine of the N-terminal residue and the C-terminal carboxyl group of the C-terminal residue, a bond between a side chain of the N-terminal residue and the C-terminal carboxyl group of the C-terminal residue, a bond between the N-terminal amine of the N-terminal residue and a side chain of the C-terminal residue, or a bond between a side chain of the N-terminal residue and a side chain of the C-terminal residue. In some embodiments, the bond between the C-terminal residue and the N-terminal residue of the peptide is a bond between the N-terminal amine of the N-terminal residue and the C-terminal carboxyl group of the C-terminal residue. In some embodiments, the bond between the C-terminal residue and the N-terminal residue is a peptide bond. In some embodiments, both the N-terminal residue and the C-terminal residue are glycine.

In some embodiments, the connection between the C-terminal residue and the N-terminal residue of the peptide comprises a linker between the C-terminal residue and the N-terminal residue, such as an alkylene or heteroalkylene linker. In some embodiments, the linker is attached to the N-terminal amine of the N-terminal residue, the C-terminal carboxyl group of the C-terminal residue, or a side chain of one or both of the N-terminal or C-terminal residue. In some embodiments, the linker is a polymeric linker, such as a polyethylene glycol (PEG) linker. In some embodiments, the C-terminal residue and the N-terminal residue of the peptide are separated by about 2, 3, 4, 5, 6, 7, 8, 9, 10, 11, or 12 consecutive amino acid residues.

In some embodiments, a linkage comprises covalent bonds between canonical or non-canonical amino acids lactam bridges. In some embodiments, a linkage comprises the structure:

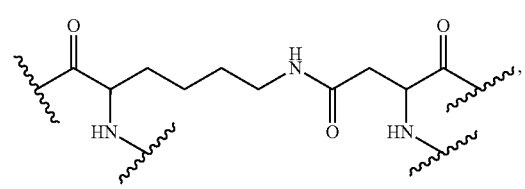

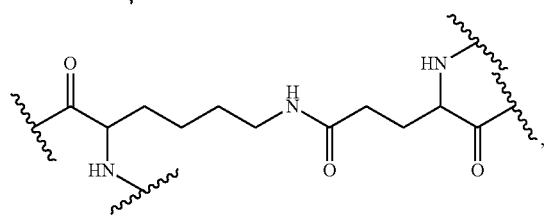

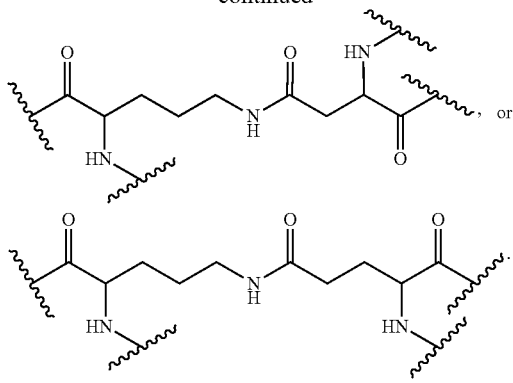

In some embodiments, the linkage comprises covalent bonds between canonical or non-canonical amino acids thioether bridges. In some embodiments, a linkage comprises the structure:

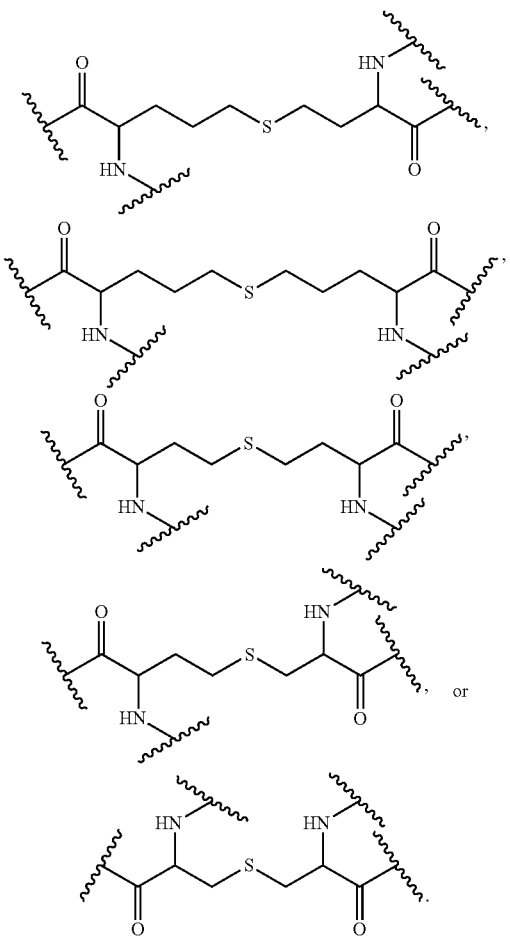

These and similar constraining structures can be used to link residues at terminal and/or nonterminal positions in the peptide. In some embodiments, Xaa3 and Xaa8 of a peptide antagonist of the disclosure are linked. In some embodiments, Xaa4 and Xaa14 of a peptide antagonist of the disclosure are linked. In some embodiments, Xaa3 and Xaa8, and Xaa4 and Xaa14, of a peptide antagonist of the disclosure are linked.

Linkage Spacing

In some embodiments, a constraining structure as described herein is selected based on the resulting spatial separation between the constrained residues. In some embodiments, the spatial separation influences a peptide antagonist property as described above. A peptide antagonist of the disclosure can comprise a constraining structure conferring a spatial separation of about 3.5 to about 10 Angstroms between alpha-carbons of the two linked amino acid residues, or between the geometrical centers of the two linked residues (e.g., amino acid derivatives). In some embodiments, the spatial separation between the alpha-carbons of the two linked amino acid residues, or the spatial separation between the geometrical centers of the two linked residues, is about 3.5 Angstroms to about 10 Angstroms. In some embodiments, the spatial separation between the alpha-carbons of the two linked amino acid residues, or the spatial separation between the geometrical centers of the two linked residues, is at least about 3.5 Angstroms. In some embodiments, the spatial separation between the alpha-carbons of the two linked amino acid residues, or the spatial separation between the geometrical centers of the two linked residues, is at most about 10 Angstroms. In some embodiments, the spatial separation between the alpha-carbons of the two linked amino acid residues, or the spatial separation between the geometrical centers of the two linked residues, is about 3.5 Angstroms to about 4.5 Angstroms, about 3.5 Angstroms to about 5 Angstroms, about 3.5 Angstroms to about 5.5 Angstroms, about 3.5 Angstroms to about 6 Angstroms, about 3.5 Angstroms to about 6.5 Angstroms, about 3.5 Angstroms to about 7 Angstroms, about 3.5 Angstroms to about 7.5 Angstroms, about 3.5 Angstroms to about 8 Angstroms, about 3.5 Angstroms to about 8.5 Angstroms, about 3.5 Angstroms to about 9 Angstroms, about 3.5 Angstroms to about 10 Angstroms, about 4.5 Angstroms to about 5 Angstroms, about 4.5 Angstroms to about 5.5 Angstroms, about 4.5 Angstroms to about 6 Angstroms, about 4.5 Angstroms to about 6.5 Angstroms, about 4.5 Angstroms to about 7 Angstroms, about 4.5 Angstroms to about 7.5 Angstroms, about 4.5 Angstroms to about 8 Angstroms, about 4.5 Angstroms to about 8.5 Angstroms, about 4.5 Angstroms to about 9 Angstroms, about 4.5 Angstroms to about 10 Angstroms, about 5 Angstroms to about 5.5 Angstroms, about 5 Angstroms to about 6 Angstroms, about 5 Angstroms to about 6.5 Angstroms, about 5 Angstroms to about 7 Angstroms, about 5 Angstroms to about 7.5 Angstroms, about 5 Angstroms to about 8 Angstroms, about 5 Angstroms to about 8.5 Angstroms, about 5 Angstroms to about 9 Angstroms, about 5 Angstroms to about 10 Angstroms, about 5.5 Angstroms to about 6 Angstroms, about 5.5 Angstroms to about 6.5 Angstroms, about 5.5 Angstroms to about 7 Angstroms, about 5.5 Angstroms to about 7.5 Angstroms, about 5.5 Angstroms to about 8 Angstroms, about 5.5 Angstroms to about 8.5 Angstroms, about 5.5 Angstroms to about 9 Angstroms, about 5.5 Angstroms to about 10 Angstroms, about 6 Angstroms to about 6.5 Angstroms, about 6 Angstroms to about 7 Angstroms, about 6 Angstroms to about 7.5 Angstroms, about 6 Angstroms to about 8 Angstroms, about 6 Angstroms to about 8.5 Angstroms, about 6 Angstroms to about 9 Angstroms, about 6 Angstroms to about 10 Angstroms, about 6.5 Angstroms to about 7 Angstroms, about 6.5 Angstroms to about 7.5 Angstroms, about 6.5 Angstroms to about 8 Angstroms, about 6.5 Angstroms to about 8.5 Angstroms, about 6.5 Angstroms to about 9 Angstroms, about 6.5 Angstroms to about 10 Angstroms, about 7 Angstroms to about 7.5 Angstroms, about 7 Angstroms to about 8 Angstroms, about 7 Angstroms to about 8.5 Angstroms, about 7 Angstroms to about 9 Angstroms, about 7 Angstroms to about 10 Angstroms, about 7.5 Angstroms to about 8 Angstroms, about 7.5 Angstroms to about 8.5 Angstroms, about 7.5 Angstroms to about 9 Angstroms, about 7.5 Angstroms to about 10 Angstroms, about 8 Angstroms to about 8.5 Angstroms, about 8 Angstroms to about 9 Angstroms, about 8 Angstroms to about 10 Angstroms, about 8.5 Angstroms to about 9 Angstroms, about 8.5 Angstroms to about 10 Angstroms, or about 9 Angstroms to about 10 Angstroms. In some embodiments, the spatial separation between the alpha-carbons of the two linked amino acid residues, or the spatial separation between the geometrical centers of the two linked residues, is about 3.5 Angstroms, about 4.5 Angstroms, about 5 Angstroms, about 5.5 Angstroms, about 6 Angstroms, about 6.5 Angstroms, about 7 Angstroms, about 7.5 Angstroms, about 8 Angstroms, about 8.5 Angstroms, about 9 Angstroms, or about 10 Angstroms. In embodiments, a specific spatial separation is achieved using a linker or spacer molecule, as known in the art.

Amino Acid Derivatives

The present disclosure contemplates the use of an amino acid derivative or analog of any amino acid in any of the peptide antagonists of the disclosure. In some embodiments, amino acid modifications can be made chemically using any known method. Selective protein modifications are described in the literature, e.g., by Spicer and Davis, 2014, "Selective chemical protein modification," Nature Communications 5: 4740, incorporated herein by reference.

In some embodiments, an amino acid derivative is a non-canonical amino acid. In some embodiments, a non-canonical amino acid has an (S) configuration at the alpha position. In some embodiments, a non-canonical amino acid has an (R) configuration at the alpha position. In some embodiments, a non-canonical amino acid is an alpha amino acid. In some embodiments, a non-canonical amino acid is a beta or gamma amino acid. In some embodiments, a non-canonical amino acid is selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid. In some embodiments, a non-canonical amino acid is a derivative of tyrosine, histidine, tryptophan, or phenylalanine. In some embodiments, a derivative of an amino acid comprises an ester, amide, disulfide, carbamate, urea, phosphate, ether of the amino acid. In some embodiments, a non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine. In some embodiments, a non-canonical amino acid is selected from the group consisting of 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and ornithine. In some embodiments, a non-canonical amino acid is a proline derivative. In some embodiments, a proline derivative is a hydroxyproline. In some embodiments, a proline derivative is 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline. In some embodiments, a non-canonical amino acid comprises a lipid.

In some embodiments, a peptide antagonist of the disclosure comprises one or more amino acid derivative or analog, e.g., as known to those of skill in the art and described in the literature or herein. In some embodiments, a peptide antagonist of the disclosure comprises 1, 2, 3, 4, 5, 6, 7, 8, 9, 10, 11, 12, 13, 14, 1-2, 1-3, 1-4, 1-5, 1-6, 1-7, 1-8, 1-9, 1-10, 1-11, 1-12, or 1-13 amino acid derivatives.

In some embodiments, each amino acid derivative present in a peptide antagonist of the disclosure is a non-canonical amino acid independently selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid, selected from e.g., the non-canonical amino acids described herein or known in the art and described in the published literature.

In some embodiments, the peptide antagonist comprises one or more amino acids that have the D-amino acid configuration, and the remaining amino acids in the peptide have the L-amino acid configuration.

In some embodiments, a non-canonical amino acid is a proline derivative. In some embodiments, a proline derivative comprises one or more substitutions on the pyrrolidine ring. In some embodiments, a proline derivative comprises one or more substitutions on the pyrrolidine ring, wherein the substitutions comprise halogen, alkoxy, amino, hydroxyl, alkyl (methyl, ethyl), thiol, or alkylthio. In some embodiments, a proline derivative comprises one or more substitutions on the pyrrolidine ring, wherein the substitutions comprise halogen, or alkyl (methyl, ethyl). In some embodiments, a proline derivative comprises one or more substitutions on the pyrrolidine ring, wherein the substitutions comprise halogen. In some embodiments, a proline derivative comprises one or more substitutions on the pyrrolidine ring, wherein the substitutions comprise alkoxy, hydroxyl, amino. In some embodiments, a proline derivative comprises one or more substitutions on the pyrrolidine ring, wherein the substitutions comprise halogen, alkoxy, alkyl (methyl, ethyl), thiol, or alkylthio.

Peptide Antagonist Tracking

In some embodiments, a peptide antagonist of the present disclosure comprises a tracker amino acid derivative that facilitates tracking of the peptide antagonist. Detection of a noncanonical tracker amino acid present in the peptide antagonist during an assay or following administration of a peptide composition to a subject or patient can provide useful information regarding a peptide antagonist property, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist).

In some embodiments, a peptide comprising a tracker amino acid derivative is detected using any assay appropriate for detecting the particular tracker amino acid derivative present in the peptide antagonist. In some embodiments, a tryptophan derivative is the tracker amino acid. In some embodiments, the assay comprises a spectroscopic or radiolabeling detection method. In some embodiments, the assay measures a pharmacokinetic or pharmacodynamic peptide antagonist property.

N-Terminal Modification of the Peptide Antagonist

In some embodiments, the N-terminus amino group of the peptide antagonist of the disclosure is modified (N-terminal modifications). In some embodiments, the N-terminus of the peptide antagonist is not modified with an additional amino acid or amino acid derivative. In some embodiments, an unmodified N terminus comprises hydrogen. In some embodiments, an N-terminal modification comprises $C_1$-$C_6$ acyl, $C_1$-$C_5$ alkyl, $C_1$-$C_{12}$ aralkyl, $C_5$-$C_{10}$ aryl, $C_4$-$C_8$ heteroaryl, formyl, or a lipid. In some embodiments, an N-terminal modification comprises $C_1$-$C_6$ aralkyl. In some embodiments, an N-terminal modification comprises $C_1$-$C_6$ acyl. In some embodiments, an N-terminal modification comprises acetyl (Ac). In some embodiments, an N-terminal modification comprises $C_1$-$C_6$ alkyl. In some embodiments, an N-terminal modification comprises methyl, ethyl, propyl, or tert-butyl. In some embodiments, an N-terminal modification comprises $C_1$-$C_6$ aralkyl. In some embodiments, an N-terminal modification comprises benzyl. In some embodiments, an N-terminal modification comprises formyl. In some embodiments, a peptide described herein, e.g., any peptide having an amino acid sequence as listed in Table 1 and Table 2 (irrespective of the N-terminus shown in the table), has any of these N-terminal modifications, or an unmodified N-terminus.

C-terminal Modification of the Peptide Antagonist

In some embodiments, the C-terminus acid group of the peptide antagonist of the disclosure is modified (C-terminal modifications). In some embodiments, the C-terminus is not modified with an additional amino acid or amino acid derivative. In some embodiments, the C-terminus is not modified with a glycine residue. In some embodiments, an unmodified C terminus comprises OH.

In some embodiments, a C-terminal modification comprises an amino group, wherein the amino group is optionally substituted. In some embodiments, a C-terminal modification comprises an amino group, wherein the amino group is unsubstituted (—NH2). In some embodiments, a C-terminal modification comprises an amino group, wherein the amino group is substituted. In some embodiments, a C-terminal modification comprises —NH2, -amino-acyl, -amino-$C_1$-$C_8$ alkyl, -amino-$C_1$-$C_6$-aralkyl, -amino-$C_5$-$C_{10}$ aryl, or -amino-$C_4$-$C_8$ heteroaryl, -amino-$C_4$-$C_8$ heteroaryl, or —O—($C_1$-$C_8$ alkyl). In some embodiments, a C-terminal modification comprises -amino-$C_6$-$C_{12}$-aralkyl. In some embodiments, a C-terminal modification comprises —O—($C_1$-$C_8$ alkyl). In some embodiments, a C-terminal modification comprises -amino-$C_6$-$C_{12}$-aralkyl. In some embodiments, a C-terminal modification comprises —NH—CH$_2$Phenyl. In some embodiments, a C-terminal modification comprises —OEt. In some embodiments, a C-terminal modification comprises —OMe. In some embodiments, a peptide described herein, e.g., any peptide having an amino acid sequence as listed in Table 1 and Table 2 (irrespective of the C-terminus shown in the table), has any of these C-terminal modifications or an unmodified C-terminus.

In some embodiments, both the N-terminus amino group and the C-terminus acid group of the peptide antagonist of the disclosure are modified. In some embodiments, a peptide described herein, e.g., any peptide having an amino acid sequence as listed in Table 1 and Table 2 (irrespective of the N- and C-termini shown in the table), has N- and C-termini independently selected from any described herein. In some embodiments, a peptide described herein, e.g., any peptide having an amino acid sequence as listed in Table 1 and Table 2 (irrespective of the N- and C-termini shown in the table), has N- and C-termini independently selected from: Ac, NH$_2$, and H.

Lipids

In some embodiments, a peptide antagonist of the present disclosure comprises a lipid moiety. In some embodiments, the lipid moiety is covalently attached to an amino acid in the peptide. In some embodiments, a lipid is attached to the N-terminus. In some embodiments, a lipid is attached to a cysteine, serine, lysine, threonine or tyrosine residue of the peptide antagonist (also referred to herein as "cys-lipid," "ser-lipid," "lys-lipid," "thr-lipid," or "tyr-lipid," respectively). In some embodiments, the lipid is covalently attached to a cysteine or lysine residue of the peptide antagonist. In some embodiments, a lipid is attached to a non-canonical amino acid. In some embodiments, a lipid comprises a hydrophobic group. In some embodiments, a lipid comprises a fatty acid group. In some embodiments, a lipid comprises a $C_6$-$C_{20}$ fatty acid group. In some embodiments, a lipid comprises a steroid. In some embodiments, a lipid comprises a wax. In some embodiments, a lipid comprises an alkyl group. In some embodiments, the lipid comprises a $C_6$-$C_{20}$ alkyl, $C_6$-$C_{20}$ alkenyl, $C_6$-$C_{20}$ alkynyl, or $C_6$-$C_{20}$ acyl group. In some embodiments, the lipid comprises one or more isoprenyl moieties. In some embodiments, the lipid comprises a geranyl, farnesyl, or geranylgeranyl group. In some embodiments, the lipid comprises an undecyloyl, lauroyl, tridecyloyl, myristoyl, palmitoyl, or stearoyl group. In some embodiments, a peptide described herein comprises an ester, amide, or thioester of a fatty acid.

In some embodiments, the lipid is a covalent modification of cysteine added by palmitoylation. In some embodiments, the lipid added by palmitoylation is a $C_6$-$C_{20}$ alkyl or a palmitoyl group.

In some embodiments, the lipid is a covalent modification of cysteine added by prenylation. In some embodiments, the lipid added by prenylation is a $C_6$-$C_{20}$ alkenyl, geranyl, farnesyl, or geranylgeranyl group.

In some embodiments, a cys-lipid has Structure I or II.

Structure I:

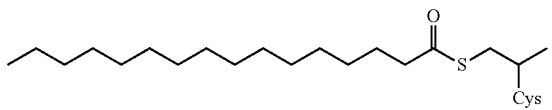

Structure II:

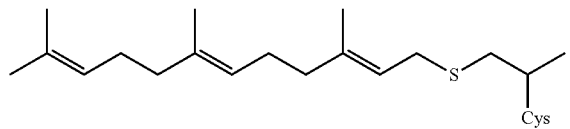

Evaluation of MC1R Peptide Antagonist

In embodiments, a peptide antagonist of the disclosure is assayed to evaluate one or more peptide properties including but not limited to a pharmacokinetic property (e.g., absorption, bioavailability, distribution, metabolism, excretion, and the like), a pharmacodynamic property (including: receptor binding characteristics, e.g., binding half-life; postreceptor effects; chemical interactions, and the like), enhanced activity (e.g., represented by IC$_{50}$), stability (e.g., represented by half-life), solubility (e.g., in a formulation), or permeability (e.g., permeability of the skin by a formulation containing the peptide antagonist).

In some embodiments, an assay is used to measure the inhibition of MC1R binding and/or activation by an MC1R agonist. In some embodiments, the agonist is α-MSH or or β-MSH. In some embodiments, an in vivo or in vitro assay known in the art appropriate for testing a peptide antagonist's effect on a G-protein coupled receptor is contemplated for use in evaluating a peptide antagonist of the disclosure. In some embodiments, the assay is a competitive binding assay. In embodiments, binding specificity is determined based on the ability of a peptide antagonist to compete with α-MSH for binding to MC1R. In some embodiments, the assay is a high-throughput assay. Other assays useful in evaluating a property of the peptide antagonist, e.g., as part of a topical formulation, of the present disclosure include skin and tissue penetration assays. In some embodiments, an assay measures the apparent treatment effect in a subject, e.g., assessment of a potential reduction or prevention of skin pigmentation or discoloration can be used to evaluate a peptide antagonist. Melanocytes reside in the basal layer of epidermis where they form the epidermal melanin units as a result of the relationship between one melanocyte and 30-40 associated keratinocytes. Thus, in some embodiments, an assay used herein evaluates the ability of a topically administered MC1R peptide antagonist to reach the melanocytes, in the basal layer of epidermis. Specific exemplary assays for evaluating a peptide antagonist of the disclosure are described in detail herein in the Examples. Any assay known in the art may be used.

In some embodiments, skin lightening by an MCR1 peptide antagonist is screened in vitro using the Melano-Derm tissue model (MatTek, Inc.), a highly differentiated, three-dimensional tissue culture model of human epidermis containing normal human melanocytes and keratinocytes. See, e.g., Makino et al., 2013, J. Drugs Dermatol. 12(3 suppl 1):s16-s20, incorporated herein by reference in its entirety. Pigmentation can be evaluated over the course of 2-3 weeks using a tristimulus chromometer to measure brightness (L*) in MelanoDerm tissue produced with normal human melanocytes from Black, Asian, or Caucasian donors. In parallel to measurements taken with the chromameter, total melanin content of tissues is also quantified. Over time, cultures become increasingly pigmented with retention of normal epithelial morphology with the expected pigmentation level of the donor tissue, i.e., Black>Asian>Caucasian when cultured in media containing alpha-MSH and beta-FGF. When pigmentation is observed over a 2-3 week treatment period, negative control cultures become increasingly pigmented while tissues treated topically with cosmetic skin lightening agents containing tyosinase inhibitors such as kojic acid and magnesium ascorbyl phosphate remain distinctly lighter when compared to control cultures. After 14 days in culture, total melanin content has been found to inversely correlate with surface reflectance (L*). Two distinct endpoints, total melanin content and skin color measurement can be used to evaluate skin pigmentation by this method.

In some embodiments, a property of a peptide antagonist measured is compared with the property of a suitable control. The result can be expressed as a comparison to an appropriate control, e.g., a negative control or a positive control. A negative control may be a non-specific binding protein, or no treatment. A positive control can be any known MC1R antagonist, e.g., Melanostatine-5/Nonapeptide 1 (SEQ ID NO: 1), the 132-amino acid natural MC1R antagonist Agouti Signaling Protein (ASIP) (SEQ ID NO: 91), mature ASIP (SEQ ID NO: 92), a fragment of ASIP, e.g., ASIP 107-132 (SEQ ID NO: 2), or a variant of ASIP or fragment thereof, e.g., ASIP-YY (SEQ ID NO: 93), ASIP-YY 107-132 subdomain (SEQ ID NO: 3), or ASIP-YY 93-132 subdomain (SEQ ID NO: 94). ASIP prevents α-MSH binding to MC1R and subsequent MC1R activation. See, e.g., Wolf Horrell, 2016.

The effect of a peptide antagonist as disclosed herein can be measured in a human subject using any method known to those of skill in the art, e.g., as described by Zasada et al., 2016, J. Cosmet. Dermatol. 15(4):493-502, incorporated herein by reference. In some embodiments, a composition comprising an MCR1 peptide antagonist may be applied to one side of a subject's face, and a control applied to the other side. A control may comprise a composition comprising a control as described herein, or a commercial skin lightening product, e.g., a hydroquinone or kojic acid-containing product. This application may be repeated one or more times a day, e.g., in the morning and in the evening. A sunscreen may be applied to the skin to minimize the effect of light exposure during the day. Subjects' skin may be photographed at intervals and evaluated by experts and/or by self-assessment, e.g., by questionnaire. Skin tone may be analyzed by taking measurements on the cheeks and forehead using Multi Probe Adapter (Courage-Khazaka Electronic GmbH, Cologne, Germany) the Mexameter® MX 18, or VISTA® Complexion Analysis system (Can-field Company, Parsippany, NJ, USA). In some embodiments, a composition comprising an MCR1 peptide antagonist prevents, reduces, and/or improves the appearance of skin discoloration. In some embodiments, the skin discoloration comprises pigmentation or hyperpigmentation. In some embodiments, the skin discoloration comprises brown spots, red spots, sun damage (photodamage) score, ruggedness of skin texture, blood vessels, and/or any other appropriate parameter understood by those of skill in the art. In some embodiments the reduction of discoloration after about 1 week to about 12 weeks of treatment is about 5% to about 50%. In some embodiments the reduction of discoloration after about 1 week to about 12 weeks of treatment is about 5% to about 50%. In some embodiments the reduction of discoloration after about 1 week to about 12 weeks of treatment is about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 25% to about 50%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%. In some embodiments the reduction of discoloration after about 1 week to about 12 weeks of treatment is about 5%, about 10%, about 15%, about 20%, about 25%, about 30%, about 35%, about 40%, about 45%, or about 50%. In some embodiments the reduction of discoloration after about 1 week to about 12 weeks of treatment is at least about 5%, about 10%, about 15%, about 20%, about 25%, about 30%, about 35%, about 40%, or about 45%. In some embodiments the reduction of discoloration after about 1 week to about 12 weeks of treatment is at most about 10%, about 15%, about 20%, about 25%, about 30%, about 35%, about 40%, about 45%, or about 50%. In some embodiments the reduction of discoloration is about 5% to 50% after about 1 week of treatment to about 12 weeks of treatment. In some embodiments the reduction of discoloration is about 5% to about 50% after about 1 week of treatment to about 2 weeks of treatment, about 1 week of treatment to about 3 weeks of treatment, about 1 week of treatment to about 4 weeks of treatment, about 1 week of treatment to about 5 weeks of treatment, about 1 week of treatment to about 6 weeks of treatment, about 1 week of treatment to about 7 weeks of treatment, about 1 week of treatment to about 8 weeks of treatment, about 1 week of treatment to about 9 weeks of treatment, about 1 week of treatment to about 10 weeks of treatment, about 1 week of treatment to about 11 weeks of treatment, about 1 week of treatment to about 12 weeks of treatment, about 2 weeks of treatment to about 3 weeks of treatment, about 2 weeks of treatment to about 4 weeks of treatment, about 2 weeks of treatment to about 5 weeks of treatment, about 2 weeks of treatment to about 6 weeks of treatment, about 2 weeks of treatment to about 7 weeks of treatment, about 2 weeks of treatment to about 8 weeks of treatment, about 2 weeks of treatment to about 9 weeks of treatment, about 2 weeks of treatment to about 10 weeks of treatment, about 2 weeks of treatment to about 11 weeks of treatment, about 2 weeks of treatment to about 12 weeks of treatment, about 3 weeks of treatment to about 4 weeks of treatment, about 3 weeks of treatment to about 5 weeks of treatment, about 3 weeks of treatment to about 6 weeks of treatment, about 3 weeks of treatment to about 7 weeks of treatment, about 3 weeks of treatment to about 8 weeks of treatment, about 3 weeks of treatment to about 9 weeks of treatment, about 3 weeks of treatment to about 10 weeks of treatment, about 3 weeks of treatment to about 11 weeks of treatment, about 3 weeks of treatment to about 12 weeks of treatment, about 4 weeks of treatment to about 5 weeks of treatment, about 4 weeks of treatment to about 6 weeks of treatment, about 4 weeks of treatment to about 7 weeks of treatment, about 4 weeks of treatment to about 8 weeks of treatment, about 4 weeks of treatment to about 9 weeks of treatment, about 4 weeks of treatment to about 10 weeks of treatment, about 4 weeks of treatment to about 11 weeks of treatment, about 4 weeks of treatment to about 12 weeks of treatment, about 5 weeks of treatment to about 6 weeks of treatment, about 5 weeks of treatment to about 7 weeks of treatment, about 5 weeks of treatment to about 8 weeks of treatment, about 5 weeks of treatment to about 9 weeks of treatment, about 5 weeks of treatment to about 10 weeks of treatment, about 5 weeks of treatment to about 11 weeks of treatment, about 5 weeks of treatment to about 12 weeks of treatment, about 6 weeks of treatment to about 7 weeks of treatment, about 6 weeks of treatment to about 8 weeks of treatment, about 6 weeks of treatment to about 9 weeks of treatment, about 6 weeks of treatment to about 10 weeks of treatment, about 6 weeks of treatment to about 11 weeks of treatment, about 6 weeks of treatment to about 12 weeks of treatment, about 7 weeks of treatment to about 8 weeks of treatment, about 7 weeks of treatment to about 9 weeks of treatment, about 7 weeks of treatment to about 10 weeks of treatment, about 7 weeks of treatment to about 11 weeks of treatment, about 7 weeks of treatment to about 12 weeks of treatment, about 8 weeks of treatment to about 9 weeks of treatment, about 8 weeks of treatment to about 10 weeks of treatment, about 8 weeks of treatment to about 11 weeks of treatment, about 8 weeks of treatment to about 12 weeks of treatment, about 9 weeks of treatment to about 10 weeks of treatment, about 9 weeks of treatment to about 11 weeks of treatment, about 9 weeks of treatment to about 12 weeks of treatment, about 10 weeks of treatment to about 11 weeks of treatment, about 10 weeks of treatment to about 12 weeks of treatment, or about 11 weeks of treatment to about 12 weeks of treatment. In some embodiments the reduction of discoloration is about 5% to 50% after about 1 week of treatment, about 2 weeks of treatment, about 3 weeks of treatment, about 4 weeks of treatment, about 5 weeks of treatment, about 6 weeks of treatment, about 7 weeks of treatment, about 8 weeks of treatment, about 9 weeks of treatment, about 10 weeks of treatment, about 11 weeks of treatment, or about 12 weeks of treatment. In some embodiments the reduction of discoloration is about 5% to 50% after at least about 1 week of treatment, about 2 weeks of treatment, about 3 weeks of treatment, about 4 weeks of treatment, about 5 weeks of treatment, about 6 weeks of treatment, about 7 weeks of treatment, about 8 weeks of treatment, about 9 weeks of treatment, about 10 weeks of treatment, or about 11 weeks of treatment. In some embodiments the reduction of discoloration is about 5% to 50% after at most about 2 weeks of treatment, about 3 weeks of treatment, about 4 weeks of treatment, about 5 weeks of treatment, about 6 weeks of treatment, about 7 weeks of treatment, about 8 weeks of treatment, about 9 weeks of treatment, about 10 weeks of treatment, about 11 weeks of treatment, or about 12 weeks of treatment. In some embodiments the reduction of discoloration after about 1 week to about 12 weeks of treatment is about 5% to about 50% in about 50% to about 100% of subjects. In some embodiments the reduction of discoloration after about 1 week to about 12 weeks of treatment is about 5% to about 50% in about 50% of subjects to about 100% of subjects. In some embodiments the reduction of discoloration after about 1 week to about 12 weeks of treatment is about 5% to about 50% in about 50% of subjects to about 55% of subjects, about 50% of subjects to about 60% of subjects, about 50% of subjects to about 65% of subjects, about 50% of subjects to about 70% of subjects, about 50% of subjects to about 75% of subjects, about 50% of subjects to about 80% of subjects, about 50% of subjects to about 85% of subjects, about 50% of subjects to about 90% of subjects, about 50% of subjects to about 95% of subjects, about 50% of subjects to about 100% of subjects, about 55% of subjects to about 60% of subjects, about 55% of subjects to about 65% of subjects, about 55% of subjects to about 70% of subjects, about 55% of subjects to about 75% of subjects, about 55% of subjects to about 80% of subjects, about 55% of subjects to about 85% of subjects, about 55% of subjects to about 90% of subjects, about 55% of subjects to about 95% of subjects, about 55% of subjects to about 100% of subjects, about 60% of subjects to about 65% of subjects, about 60% of subjects to about 70% of subjects, about 60% of subjects to about 75% of subjects, about 60% of subjects to about 80% of subjects, about 60% of subjects to about 85% of subjects, about 60% of subjects to about 90% of subjects, about 60% of subjects to about 95% of subjects, about 60% of subjects to about 100% of subjects, about 65% of subjects to about 70% of subjects, about 65% of subjects to about 75% of subjects, about 65% of subjects to about 80% of subjects, about 65% of subjects to about 85% of subjects, about 65% of subjects to about 90% of subjects, about 65% of subjects to about 95% of subjects, about 65% of subjects to about 100% of subjects, about 70% of subjects to about 75% of subjects, about 70% of subjects to about 80% of subjects, about 70% of subjects to about 85% of subjects, about 70% of subjects to about 90% of subjects, about 70% of subjects to about 95% of subjects, about 70% of subjects to about 100% of subjects, about 75% of subjects to about 80% of subjects, about 75% of subjects to about 85% of subjects, about 75% of subjects to about 90% of subjects, about 75% of subjects to about 95% of subjects, about 75% of subjects to about 100% of subjects, about 80% of subjects to about 85% of subjects, about 80% of subjects to about 90% of subjects, about 80% of subjects to about 95% of subjects, about 80% of subjects to about 100% of subjects, about 85% of subjects to about 90% of subjects, about 85% of subjects to about 95% of subjects, about 85% of subjects to about 100% of subjects, about 90% of subjects to about 95% of subjects, about 90% of subjects to about 100% of subjects, or about 95% of subjects to about 100% of subjects. In some embodiments the reduction of discoloration after about 1 week to about 12 weeks of treatment is about 5% to about 50% in about 50% of subjects, about 55% of subjects, about 60% of subjects, about 65% of subjects, about 70% of subjects, about 75% of subjects, about 80% of subjects, about 85% of subjects, about 90% of subjects, about 95% of subjects, or about 100% of subjects. In some embodiments the reduction of discoloration after about 1 week to about 12 weeks of treatment is about 5% to about 50% in at least about 50% of subjects, about 55% of subjects, about 60% of subjects, about 65% of subjects, about 70% of subjects, about 75% of subjects, about 80% of subjects, about 85% of subjects, about 90% of subjects, or about 95% of subjects. In some embodiments the reduction of discoloration after about 1 week to about 12 weeks of treatment is about 5% to about 50% in at most about 55% of subjects, about 60% of subjects, about 65% of subjects, about 70% of subjects, about 75% of subjects, about 80% of subjects, about 85% of subjects, about 90% of subjects, about 95% of subjects, or about 100% of subjects.

The inhibition of MC1R activation by a peptide antagonist of the present disclosure can be compared with that of a known antagonist, e.g., Melanostatine-5 (SEQ ID NO: 1), ASIP (SEQ ID NO: 2), or ASIP-YY (SEQ ID NO: 3). In some embodiments, a peptide antagonist is compared in an assay to a control. In some embodiments, the control is a negative control, e.g., a random peptide. In some embodiments, the control is positive control, e.g., any MC1R antagonist known in the art. In some embodiments, the MC1R peptide antagonist tested is a Group A peptide antagonist, e.g., having an amino acid sequence of any one of SEQ ID NOS: 4-43, and the control is a peptide having the amino acid sequence set forth as SEQ ID NO: 1. In some embodiments, the MC1R peptide antagonist is a Group B peptide antagonist, e.g., having an amino acid sequence of any one of SEQ ID NOS: 44-90, and the control is a peptide having the amino acid sequence set forth as any one of SEQ ID NOS: 2, 3, and 91-94. In some embodiments, the MC1R peptide antagonist is a Group B peptide antagonist, e.g., having an amino acid sequence of any one of SEQ ID NOS: 44-90, and the control is a peptide having the amino acid sequence set forth as SEQ ID NO: 2. In some embodiments, the MC1R peptide antagonist is a Group B peptide antagonist, e.g., having an amino acid sequence of any one of SEQ ID NOS: 44-90, and the control is a peptide having the amino acid sequence set forth as SEQ ID NO: 3.

In embodiments, the inhibition of MC1R activation by a peptide antagonist of the present disclosure is compared with that of a known antagonist using the same assay. In embodiments, the inhibition of MC1R activation by a peptide antagonist of the present disclosure is compared with that of a known antagonist in the same experiment. In embodiments, the inhibition of MC1R activation by a peptide antagonist of the present disclosure is compared with that of a known antagonist in the same experiment, using the same assay.

In embodiments, a peptide antagonist of the disclosure inhibits MC1R at an $IC_{50}$ of about 1 millimolar to about 1 picomolar. In some embodiments, the peptide antagonist has an $IC_{50}$ of about 1 millimolar to about 1 picomolar in a receptor binding assay. In some embodiments, the $IC_{50}$ is about 1 millimolar to about 1 micromolar, about 1 millimolar to about 500 micromolar, about 500 micromolar to about 100 micromolar, about 100 micromolar to about 1 micromolar, about 1 micromolar to about 1 nanomolar, about 1 micromolar to about 1 nanomolar, about 1 micromolar to about 500 nanomolar, about 500 nanomolar to about 100 nanomolar, about 100 nanomolar to about 1 nanomolar, about 1 nanomolar to about 1 picomolar, about 1 nanomolar to about 500 picomolar, about 500 picomolar to about 100 picomolar, about 100 micromolar to about 1 picomolar, about or less than about 1 millimolar, about or less than about 500 millimolar, about or less than about 100 millimolar, about or less than about 1 millimolar, about or less than about 1 micromolar, about or less than about 500 micromolar, about or less than about 100 micromolar, about or less than about 50 micromolar, about or less than about 20 micromolar, about or less than about 10 micromolar, about or less than about 5 micromolar, about or less than about 2 micromolar, about or less than about 1 micromolar, about or less than about 1 nanomolar, about or less than about 500 nanomolar, about or less than about 100 nanomolar, about or less than about 1 nanomolar, about or less than about 1 picomolar, about or less than about 500 picomolar, about or less than about 100 picomolar, or about or less than about 1 picomolar. In some embodiments, the $IC_{50}$ is about 20 nanomolar to about 125 nanomolar. In some embodiments, the $IC_{50}$ is about 20 nanomolar to about 25 nanomolar, about 20 nanomolar to about 30 nanomolar, about 20 nanomolar to about 40 nanomolar, about 20 nanomolar to about 50 nanomolar, about 20 nanomolar to about 60 nanomolar, about 20 nanomolar to about 70 nanomolar, about 20 nanomolar to about 75 nanomolar, about 20 nanomolar to about 80 nanomolar, about 20 nanomolar to about 90 nanomolar, about 20 nanomolar to about 100 nanomolar, about 20 nanomolar to about 125 nanomolar, about 25 nanomolar to about 30 nanomolar, about 25 nanomolar to about 40 nanomolar, about 25 nanomolar to about 50 nanomolar, about 25 nanomolar to about 60 nanomolar, about 25 nanomolar to about 70 nanomolar, about 25 nanomolar to about 75 nanomolar, about 25 nanomolar to about 80 nanomolar, about 25 nanomolar to about 90 nanomolar, about 25 nanomolar to about 100 nanomolar, about 25 nanomolar to about 125 nanomolar, about 30 nanomolar to about 40 nanomolar, about 30 nanomolar to about 50 nanomolar, about 30 nanomolar to about 60 nanomolar, about 30 nanomolar to about 70 nanomolar, about 30 nanomolar to about 75 nanomolar, about 30 nanomolar to about 80 nanomolar, about 30 nanomolar to about 90 nanomolar, about 30 nanomolar to about 100 nanomolar, about 30 nanomolar to about 125 nanomolar, about 40 nanomolar to about 50 nanomolar, about 40 nanomolar to about 60 nanomolar, about 40 nanomolar to about 70 nanomolar, about 40 nanomolar to about 75 nanomolar, about 40 nanomolar to about 80 nanomolar, about 40 nanomolar to about 90 nanomolar, about 40 nanomolar to about 100 nanomolar, about 40 nanomolar to about 125 nanomolar, about 50 nanomolar to about 60 nanomolar, about 50 nanomolar to about 70 nanomolar, about 50 nanomolar to about 75 nanomolar, about 50 nanomolar to about 80 nanomolar, about 50 nanomolar to about 90 nanomolar, about 50 nanomolar to about 100 nanomolar, about 50 nanomolar to about 125 nanomolar, about 60 nanomolar to about 70 nanomolar, about 60 nanomolar to about 75 nanomolar, about 60 nanomolar to about 80 nanomolar, about 60 nanomolar to about 90 nanomolar, about 60 nanomolar to about 100 nanomolar, about 60 nanomolar to about 125 nanomolar, about 70 nanomolar to about 75 nanomolar, about 70 nanomolar to about 80 nanomolar, about 70 nanomolar to about 90 nanomolar, about 70 nanomolar to about 100 nanomolar, about 70 nanomolar to about 125 nanomolar, about 75 nanomolar to about 80 nanomolar, about 75 nanomolar to about 90 nanomolar, about 75 nanomolar to about 100 nanomolar, about 75 nanomolar to about 125 nanomolar, about 80 nanomolar to about 90 nanomolar, about 80 nanomolar to about 100 nanomolar, about 80 nanomolar to about 125 nanomolar, about 90 nanomolar to about 100 nanomolar, about 90 nanomolar to about 125 nanomolar, or about 100 nanomolar to about 125 nanomolar. In some embodiments, the $IC_{50}$ is about 20 nanomolar, about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, about 100 nanomolar, or about 125 nanomolar. In some embodiments, the $IC_{50}$ is at least about 20 nanomolar, about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, or about 100 nanomolar. In some embodiments, the $IC_{50}$ is at most about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, about 100 nanomolar, or about 125 nanomolar.

In some embodiments, the $IC_{50}$ of the peptide antagonist is about 25 nanomolar to about 150 nanomolar. In some embodiments, the $IC_{50}$ of the peptide antagonist is at least about 25 nanomolar. In some embodiments, the $IC_{50}$ of the peptide antagonist is at most about 150 nanomolar. In some embodiments, the $IC_{50}$ of the peptide antagonist is about 25 nanomolar to about 35 nanomolar, about 25 nanomolar to about 40 nanomolar, about 25 nanomolar to about 45 nanomolar, about 25 nanomolar to about 50 nanomolar, about 25 nanomolar to about 60 nanomolar, about 25 nanomolar to about 70 nanomolar, about 25 nanomolar to about 75 nanomolar, about 25 nanomolar to about 100 nanomolar, about 25 nanomolar to about 110 nanomolar, about 25 nanomolar to about 125 nanomolar, about 25 nanomolar to about 150 nanomolar, about 35 nanomolar to about 40 nanomolar, about 35 nanomolar to about 45 nanomolar, about 35 nanomolar to about 50 nanomolar, about 35 nanomolar to about 60 nanomolar, about 35 nanomolar to about 70 nanomolar, about 35 nanomolar to about 75 nanomolar, about 35 nanomolar to about 100 nanomolar, about 35 nanomolar to about 110 nanomolar, about 35 nanomolar to about 125 nanomolar, about 35 nanomolar to about 150 nanomolar, about 40 nanomolar to about 45 nanomolar, about 40 nanomolar to about 50 nanomolar, about 40 nanomolar to about 60 nanomolar, about 40 nanomolar to about 70 nanomolar, about 40 nanomolar to about 75 nanomolar, about 40 nanomolar to about 100 nanomolar, about 40 nanomolar to about 110 nanomolar, about 40 nanomolar to about 125 nanomolar, about 40 nanomolar to about 150 nanomolar, about 45 nanomolar to about 50 nanomolar, about 45 nanomolar to about 60 nanomolar, about 45 nanomolar to about 70 nanomolar, about 45 nanomolar to about 75 nanomolar, about 45 nanomolar to about 100 nanomolar, about 45 nanomolar to about 110 nanomolar, about 45 nanomolar to about 125 nanomolar, about 45 nanomolar to about 150 nanomolar, about 50 nanomolar to about 60 nanomolar, about 50 nanomolar to about 70 nanomolar, about 50 nanomolar to about 75 nanomolar, about 50 nanomolar to about 100 nanomolar, about 50 nanomolar to about 110 nanomolar, about 50 nanomolar to about 125 nanomolar, about 50 nanomolar to about 150 nanomolar, about 60 nanomolar to about 70 nanomolar, about 60 nanomolar to about 75 nanomolar, about 60 nanomolar to about 100 nanomolar, about 60 nanomolar to about 110 nanomolar, about 60 nanomolar to about 125 nanomolar, about 60 nanomolar to about 150 nanomolar, about 70 nanomolar to about 75 nanomolar, about 70 nanomolar to about 100 nanomolar, about 70 nanomolar to about 110 nanomolar, about 70 nanomolar to about 125 nanomolar, about 70 nanomolar to about 150 nanomolar, about 75 nanomolar to about 100 nanomolar, about 75 nanomolar to about 110 nanomolar, about 75 nanomolar to about 125 nanomolar, about 75 nanomolar to about 150 nanomolar, about 100 nanomolar to about 110 nanomolar, about 100 nanomolar to about 125 nanomolar, about 100 nanomolar to about 150 nanomolar, about 110 nanomolar to about 125 nanomolar, about 110 nanomolar to about 150 nanomolar, or about 125 nanomolar to about 150 nanomolar. In some embodiments, the IC50 of the peptide antagonist is about 25 nanomolar, about 35 nanomolar, about 40 nanomolar, about 45 nanomolar, about 50 nanomolar, about 60 nanomolar, about 70 nanomolar, about 75 nanomolar, about 100 nanomolar, about 110 nanomolar, about 125 nanomolar, or about 150 nanomolar.

In embodiments, the $IC_{50}$ is less than about 200 nM, less than about 150 nM, less than about 100 nM, less than about 75 nM, less than about 50 nM, or less than about 25 nM.

The IC5o can be determined by any appropriate activity assay as described herein or known in the art. In embodiments, the $IC_{50}$ represents the concentration of peptide antagonist at which 50% of the MC1R binding to an MC1R agonist is blocked.

In some embodiments, the $IC_{50}$ observed using a peptide antagonist of the disclosure is lower than that of a control (comparison) MC1R peptide antagonist. A control MC1R peptide antagonist can be any MC1R peptide antagonist known in the art, e.g., Melanostatine-5/Nonapeptide 1 (SEQ ID NO: 1), the 132-amino acid natural MC1R antagonist Agouti Signaling Protein (ASIP) (SEQ ID NO: 91), mature ASIP (SEQ ID NO: 92), a fragment of ASIP, e.g., ASIP 107-132 (SEQ ID NO: 2), or a variant of ASIP or fragment thereof, e.g., ASIP-YY (SEQ ID NO: 93), ASIP-YY 107-132 subdomain (SEQ ID NO: 3), or ASIP-YY 93-132 subdomain (SEQ ID NO: 94). In some embodiments, the $IC_{50}$ observed using a peptide antagonist of the disclosure is about 0.4 to about 0.8 times that of the control antagonist. In some embodiments, the $IC_{50}$ observed using a peptide antagonist of the disclosure is lower that of the control antagonist by about 2-fold to about 10-fold, i.e., the $IC_{50}$ is about 10% to about 50% that observed with the control antagonist. In some embodiments, the $IC_{50}$ observed using a peptide antagonist of the disclosure is lower than that of the control antagonist by about 2-fold to about 10-fold. In some embodiments, the $IC_{50}$ observed using a peptide antagonist of the disclosure is lower that of the control antagonist by about 2-fold to about 3-fold, about 2-fold to about 4-fold, about 2-fold to about 5-fold, about 2-fold to about 6-fold, about 2-fold to about 7-fold, about 2-fold to about 8-fold, about 2-fold to about 9-fold, about 2-fold to about 10-fold, about 3-fold to about 4-fold, about 3-fold to about 5-fold, about 3-fold to about 6-fold, about 3-fold to about 7-fold, about 3-fold to about 8-fold, about 3-fold to about 9-fold, about 3-fold to about 10-fold, about 4-fold to about 5-fold, about 4-fold to about 6-fold, about 4-fold to about 7-fold, about 4-fold to about 8-fold, about 4-fold to about 9-fold, about 4-fold to about 10-fold, about 5-fold to about 6-fold, about 5-fold to about 7-fold, about 5-fold to about 8-fold, about 5-fold to about 9-fold, about 5-fold to about 10-fold, about 6-fold to about 7-fold, about 6-fold to about 8-fold, about 6-fold to about 9-fold, about 6-fold to about 10-fold, about 7-fold to about 8-fold, about 7-fold to about 9-fold, about 7-fold to about 10-fold, about 8-fold to about 9-fold, about 8-fold to about 10-fold, or about 9-fold to about 10-fold. In some embodiments, the $IC_{50}$ observed using a peptide antagonist of the disclosure is lower than that of the control antagonist by about 2-fold, about 3-fold, about 4-fold, about 5-fold, about 6-fold, about 7-fold, about 8-fold, about 9-fold, or about 10-fold. In some embodiments, the $IC_{50}$ observed using a peptide antagonist of the disclosure is lower than that of the control antagonist by at least about 2-fold, about 3-fold, about 4-fold, about 5-fold, about 6-fold, about 7-fold, about 8-fold, or about 9-fold. In some embodiments, the $IC_{50}$ observed using a peptide antagonist of the disclosure is lower than that of the control antagonist by at most about 3-fold, about 4-fold, about 5-fold, about 6-fold, about 7-fold, about 8-fold, about 9-fold, or about 10-fold. In some embodiments, the activity of a peptide antagonist of the disclosure activity is greater than the activity of a control by about 1.25-fold to about 5-fold.

In some embodiments, the activity of a peptide antagonist of the disclosure activity is greater than the activity of a control by about 1.25-fold to about 5-fold. In some embodiments, the activity of a peptide antagonist of the disclosure activity is greater than the activity of a control by about 1.25-fold to about 1.5-fold, about 1.25-fold to about 1.75-fold, about 1.25-fold to about 2-fold, about 1.25-fold to about 2.5-fold, about 1.25-fold to about 3-fold, about 1.25-fold to about 3.5-fold, about 1.25-fold to about 4-fold, about 1.25-fold to about 4.5-fold, about 1.25-fold to about 5-fold, about 1.5-fold to about 1.75-fold, about 1.5-fold to about 2-fold, about 1.5-fold to about 2.5-fold, about 1.5-fold to about 3-fold, about 1.5-fold to about 3.5-fold, about 1.5-fold to about 4-fold, about 1.5-fold to about 4.5-fold, about 1.5-fold to about 5-fold, about 1.75-fold to about 2-fold, about 1.75-fold to about 2.5-fold, about 1.75-fold to about 3-fold, about 1.75-fold to about 3.5-fold, about 1.75-fold to about 4-fold, about 1.75-fold to about 4.5-fold, about 1.75-fold to about 5-fold, about 2-fold to about 2.5-fold, about 2-fold to about 3-fold, about 2-fold to about 3.5-fold, about 2-fold to about 4-fold, about 2-fold to about 4.5-fold, about 2-fold to about 5-fold, about 2.5-fold to about 3-fold, about 2.5-fold to about 3.5-fold, about 2.5-fold to about 4-fold, about 2.5-fold to about 4.5-fold, about 2.5-fold to about 5-fold, about 3-fold to about 3.5-fold, about 3-fold to about 4-fold, about 3-fold to about 4.5-fold, about 3-fold to about 5-fold, about 3.5-fold to about 4-fold, about 3.5-fold to about 4.5-fold, about 3.5-fold to about 5-fold, about 4-fold to about 4.5-fold, about 4-fold to about 5-fold, or about 4.5-fold to about 5-fold. In some embodiments, the activity of a peptide antagonist of the disclosure activity is greater than the activity of a control by about 1.25-fold, about 1.5-fold, about 1.75-fold, about 2-fold, about 2.5-fold, about 3-fold, about 3.5-fold, about 4-fold, about 4.5-fold, or about 5-fold. In some embodiments, the activity of a peptide antagonist of the disclosure activity is greater than the activity of a control by at least about 1.25-fold, about 1.5-fold, about 1.75-fold, about 2-fold, about 2.5-fold, about 3-fold, about 3.5-fold, about 4-fold, or about 4.5-fold. In some embodiments, the activity of a peptide antagonist of the disclosure activity is greater than the activity of a control by at most about 1.5-fold, about 1.75-fold, about 2-fold, about 2.5-fold, about 3-fold, about 3.5-fold, about 4-fold, about 4.5-fold, or about 5-fold.

In some embodiments, the $IC_{50}$ observed for a Group A peptide antagonist of the disclosure is about 10% to about 50% of the $IC_{50}$ observed for a control, e.g., SEQ ID NO: 1. In some embodiments, the observed for a Group B peptide antagonist of the disclosure is about 10% to about 50% of the $IC_{50}$ observed for a control, e.g., SEQ ID NO: 2, 3, or 91-94. In some embodiments, the $IC_{50}$ observed for a Group A or B peptide antagonist of the disclosure is about 10% to about 50% of the $IC_{50}$ observed for a control, e.g., SEQ ID NO: 1, 2, 3, or 91-94.

Indications

The MC1R peptide antagonists of the disclosure are contemplated for cosmetic uses in a subject in need thereof, for indications including but not limited to the prevention, reduction, and/or improvement of the appearance of undesirable skin discoloration. The skin discoloration can be caused by pigmentation. The skin discoloration can be caused by hyperpigmentation. In some embodiments, the skin discoloration, e.g., pigmentation or hyperpigmentation, comprises melanin hyperpigmentation, post-inflammatory hyperpigmentation, chloasma, melasma, age spots (e.g., liver spots, senile lentigines, solar lentigines, sunspots), freckles, or a combination thereof. The MC1R peptide antagonists of the disclosure can be used to treat skin discoloration resulting from a disorder, e.g., an adrenal disorder. In embodiments, the MC1R peptide antagonists of the disclosure are used to treat skin discoloration caused by Addison's disease, in which MC1R agonists ACTH and MSH are overproduced. In embodiments, the MC1R peptide antagonists of the disclosure are used to treat skin discoloration due to hyperpigmentation of any known cause, e.g., drug use (e.g., calcium antagonists), cyanic melasma, senile melasma, vitiligo, adverse sequelae following sclerotherapy, or postinflammatory or traumatic responses. In some embodiments, existing skin discoloration is reduced. In some embodiments, further skin discoloration is prevented. In some embodiments, the skin discoloration is improved in appearance, e.g., due to a change in the texture (ruggedness) of the skin.

In some embodiments, the subject is a mammal. In specific embodiments, the mammal is a human. In some embodiments, the human subject is a pediatric or adult subject, of any age.

Formulations

In certain embodiments, including pharmaceutical embodiments, peptide antagonists of the disclosure can be provided in a cosmetic or pharmaceutical composition. In some embodiments, cosmetic or pharmaceutical compositions of the disclosure are: formulated using excipients or carriers that are not toxic to keratinous tissue, e.g., skin, and are cosmetically, pharmaceutically and/or dermatologically acceptable; and administered in treatments comprising a subimmunological dose of the composition.

In certain embodiments, including pharmaceutical embodiments, administration of a formulation of the disclosure, e.g., a cosmetic or pharmaceutical composition, to a subject is not expected to result in adverse effects, even when administered repeatedly and often, e.g., as described herein. In embodiments, adverse effects are minor, few, or nonexistent. Adverse effects of topical application can include, e.g., mild to severe skin pain, redness, burning, itching, irritation, or any other side effects commonly associated with topical compositions.

More severe effects avoided by formulations of the disclosure can include side effects associated with injectable neurotoxins as described in product labeling, e.g., as referenced herein.

Cosmetic and Pharmaceutical Compositions

The present disclosure includes a cosmetic composition comprising a peptide antagonist of the disclosure. In some embodiments, the cosmetic composition is formulated for topical administration. In some embodiments, the cosmetic composition is formulated for topical administration as a cream, balm, gel, solution, serum, cosmetic, liquid, lotion, ointment, emulsion, milk, spray, mask, or the like.

In certain embodiments, including pharmaceutical embodiments, a topical cosmetic or pharmaceutical composition comprises an excipient or carrier or a suitable combination of two, three, or more excipients or carriers. In some embodiments, any appropriate excipient or carrier or combination of multiple excipients and/or carriers is selected from excipients known to those of skill in the art and described in the literature, e.g., those useful in a topical formulation. In some embodiments, an excipient or carrier useful in a topical formulation is selected from the group consisting of: an inert excipient or carrier, a buffer, an absorption enhancer (penetrating agent), and a stability enhancer. In some embodiments, the inert excipient or carrier is water, isopropyl alcohol, gaseous fluorocarbons, ethyl alcohol, polyvinyl pyrrolidone, propylene glycol, a fragrance, a gel-producing material, stearyl alcohol, stearic acid, spermaceti, sorbitan monooleate, or methylcellulose. In some embodiments, the excipient is an inorganic compound. In some embodiments, an excipient is a carbohydrate. In some embodiments, the excipient is diaminobutyroyl benzylamide, diacetate, glycerin, a gum, a hydrophilic colloid or derivative, a cellulosic derivative, an emulsifier, a fatty alcohol, an acrylic derivative, a mineral, a surfactant, a fat, an oil, a preservative, a monosaccharide, a disaccharide, a polysaccharide, a glycosaminoglycan, or a chelating agent.

In some embodiments, the absorption enhancer is selected from the group consisting of: a liposome delivery system, a transfersome delivery system, an ethosome delivery system, a short chain alcohol, a long chain alcohol, a polyalcohol, urea, an amino acid, an amino acid ester, an amine, an amide, an azacyclo compound (e.g., 1-dodecylazacycloheptan-2-one (AZONE®) or a derivative of 1-dodecylazacycloheptan-2-one) a pyrrolidone, a pyrrolidone derivative, a terpene, a terpene derivative, a fatty acid, a fatty acid ester, a macrocyclic compound, a tenside, a sulfoxide, lecithin vesicles, water surfactants, a polyol, a small molecule tri, tetra, penta, hexa, septa or octa peptide, isoceteth-20, ethoxydiglycol, dimethyl sulfoxide (DMSO), dimethyl isosorbide, and phloretin. In some embodiments, the absorption enhancer is selected to have a minimal allergic or irritating effect.

In some embodiments, the stability enhancer is a small molecule peptide. In some embodiments, the small molecule peptide is selected from the group consisting of: a tripeptide, a tetrapeptide, a pentapeptide, a hexapeptide, a septapeptide, an octapeptide, Acetyl Hexapeptide-3 Cosmetic Topical Peptide, Melanotan II, ACVR2B (ACE-031), Argireline® Acetate, Argireline, Matrixyl Acetate (palmitoyl pentapeptide), peptide GHK spontaneously complexes with copper, Palmitoyl Tetrapeptide-3, Argireline, Acetyl Glutamyl Heptapeptide, Matrixyl™, Snap-8, Syn°-Tacks, Syn®-Coll, Syn®-Hycan, Leuphasyl®, Pepha®-Tight, Tego® Pep 4-17 and Trylagen®.

In some embodiments, the cosmetic composition further comprises one or more additional active ingredient. In some embodiments, the one or more additional active ingredient is selected from the group consisting of: a second, different, MC1R peptide antagonist, another skin-lightening agent, an anti-wrinkle agent, a retinoid, an antioxidant, a growth factor, a collagen stimulating peptide, a carrier peptide, a peptide that inhibits tTAT-superoxide dismutase, a peptide that inhibits a proteinase, a peptide that stimulates hyaluronan synthase 2, and a keratin-based peptide.

In some embodiments, the cosmetic composition comprises a liposome delivery system. In some embodiments, the liposome delivery system includes, e.g., oil-in-water emulsions, micelles, mixed micelles, or liposomes. In some embodiments, a colloidal system is a liposome or microsphere. In some embodiments, a composition is formulated as a poly(D,L)lactide microspheres. In certain embodiments, including pharmaceutical embodiments, the cosmetic composition is formulated to incorporate features as described below, for use in a pharmaceutical composition.

In some embodiments, the excipient(s) and/or liposome delivery system are selected using methods known to those of skill in the art to achieve the desired degree of penetration, e.g., to achieve substantially local delivery. In some embodiments, the excipient(s) and/or liposome delivery system are selected to target melanocytes in the basal layer of the epidermis.

In some embodiments, transdermal delivery of an MC1R peptide antagonist described herein is achieved using a liposome or lipid vesicle composition. In some embodiments, the lipid vesicle composition comprises lipid vesicles each comprising a lipid bilayer comprising vesicle forming lipids. In some embodiments, the lipid vesicle composition comprises an oil-in-water emulsion entrapped in the lipid vesicles. In some embodiments, the oil-in-water emulsion is stabilized by one or more surfactants. In some embodiments, the MC1R peptide antagonist is entrapped in the lipid bilayer and/or the oil-in-water emulsion. In some embodiments, the MC1R peptide antagonist is entrapped in the lipid bilayer. In some embodiments, the MC1R peptide antagonist is entrapped in the oil-in-water emulsion. In some embodiments, the lipid vesicle composition comprises: (a) lipid vesicles each comprising a lipid bilayer comprising vesicle forming lipids; (b) an oil-in-water emulsion entrapped in the lipid vesicles, and stabilized by one or more surfactants; and (c) an MC1R peptide antagonist entrapped in the lipid bilayer and/or the oil-in-water emulsion.

In certain embodiments, including pharmaceutical embodiments, the present disclosure also includes pharmaceutical compositions comprising a peptide antagonist of the disclosure. In some embodiments, the pharmaceutical composition is formulated as described above for a cosmetic composition comprising a peptide antagonist of the disclosure.

In certain embodiments, including pharmaceutical embodiments, a cosmetic or pharmaceutical composition of the disclosure is formulated using any excipient, carrier, or additive as appropriate.

Methods for Using Cosmetic or Pharmaceutical Compositions

The disclosure includes compositions comprising one or more MC1R peptide antagonist as described herein, e.g., a Group A or Group B MC1R peptide antagonist having an amino acid sequence as set forth in Table 1 and Table 2, or as otherwise described herein. In certain embodiments, including pharmaceutical embodiments, the composition is a cosmetic or pharmaceutical composition.

The disclosure also relates to methods for blocking or inhibiting MSH-MC1R interactions using MC1R peptide antagonist composition, comprising contacting the MC1R peptide antagonist with the MC1R peptide antagonist composition. The disclosure also relates to the use of an MC1R peptide antagonist or composition thereof to prevent or reduce skin discoloration in a subject.

In certain embodiments, including pharmaceutical embodiments, the present disclosure also relates to methods for using cosmetic or pharmaceutical compositions comprising a peptide antagonist of the disclosure. In some embodiments, the disclosure relates to methods for using the cosmetic or pharmaceutical composition to prevent, reduce, and/or improve the appearance in a subject of skin discoloration, comprising applying an effective amount of the cosmetic or pharmaceutical composition to the skin of the subject. In some embodiments, the skin discoloration comprises melanin hyperpigmentation, post-inflammatory hyperpigmentation, chloasma, melasma, age spots (e.g., liver spots, senile lentigines, solar lentigines, sunspots), freckles, or a combination thereof. In some embodiments, the skin discoloration results from a disorder, e.g., an adrenal disorder. In some embodiments, the MC1R peptide antagonists of the disclosure are used to prevent or reduce skin discoloration caused by Addison's disease. In some embodiments, administration is topical. In some embodiments, administration is to the skin. In some embodiments, administration is topically applied to the skin.

In some embodiments, a subject in the context of the present disclosure is a mammalian subject. In some embodiments, the mammal is a human. In some embodiments, the human subject is a pediatric, juvenile, or adult subject, of any age. In some embodiments, the subject has a disease or disorder that causes unwanted skin pigmentation. In embodiments the subject has Addison's disease.

In certain embodiments, including pharmaceutical embodiments, the cosmetic or pharmaceutical composition is topically applied to a subject. Topical application as referred to herein can refer to application onto one or more surface, e.g., keratinous tissue. Topical application may relate to direct application to the desired area. A topical cosmetic or pharmaceutical composition or preparation can be applied by, e.g., pouring, dropping, or spraying, when present as a liquid or aerosol composition; smoothing, rubbing, spreading, and the like, when in ointment, lotion, cream, gel, or a like composition; dusting, when a powder; or by any other appropriate means.

In certain embodiments, including pharmaceutical embodiments, a subject is treated with an effective amount of the topical cosmetic or pharmaceutical composition during a period between treatments with a skin peeling agent. In some embodiments a subject is treated with a topical cosmetic or pharmaceutical composition of the disclosure periodically beginning on the day after, for 1, 2, 3, 4, 5, 6, 7, 8, 9, 10, 11, 12, 13, 14, 15, 16, 17, 18, 19, 20, 21, 22, 23, 24, 25, or 26 weeks after a treatment with the skin peeling agent.

In certain embodiments, including pharmaceutical embodiments, the subject is treated by topical application of an effective amount of the cosmetic or pharmaceutical composition one time or more during a course of treatment, e.g., 1-3 times per day, 1-21 times per week, 1 time per day, 2 times per day, or 3 times per day. In some embodiments, a subject is treated with an effective amount of the cosmetic or pharmaceutical composition about 1 time per week to about 12 times per week. In some embodiments, a subject is treated with an effective amount of the cosmetic or pharmaceutical composition at least about 1 time per week. In some embodiments, a subject is treated with an effective amount of the cosmetic or pharmaceutical composition at most about 12 times per week. In some embodiments, a subject is treated with an effective amount of the cosmetic or pharmaceutical composition about 1 time per week to about 2 times per week, about 1 time per week to about 3 times per week, about 1 time per week to about 4 times per week, about 1 time per week to about 5 times per week, about 1 time per week to about 6 times per week, about 1 time per week to about 7 times per week, about 1 time per week to about 8 times per week, about 1 time per week to about 9 times per week, about 1 time per week to about 10 times per week, about 1 time per week to about 11 times per week, about 1 time per week to about 12 times per week, about 2 times per week to about 3 times per week, about 2 times per week to about 4 times per week, about 2 times per week to about 5 times per week, about 2 times per week to about 6 times per week, about 2 times per week to about 7 times per week, about 2 times per week to about 8 times per week, about 2 times per week to about 9 times per week, about 2 times per week to about 10 times per week, about 2 times per week to about 11 times per week, about 2 times per week to about 12 times per week, about 3 times per week to about 4 times per week, about 3 times per week to about 5 times per week, about 3 times per week to about 6 times per week, about 3 times per week to about 7 times per week, about 3 times per week to about 8 times per week, about 3 times per week to about 9 times per week, about 3 times per week to about 10 times per week, about 3 times per week to about 11 times per week, about 3 times per week to about 12 times per week, about 4 times per week to about 5 times per week, about 4 times per week to about 6 times per week, about 4 times per week to about 7 times per week, about 4 times per week to about 8 times per week, about 4 times per week to about 9 times per week, about 4 times per week to about 10 times per week, about 4 times per week to about 11 times per week, about 4 times per week to about 12 times per week, about 5 times per week to about 6 times per week, about 5 times per week to about 7 times per week, about 5 times per week to about 8 times per week, about 5 times per week to about 9 times per week, about 5 times per week to about 10 times per week, about 5 times per week to about 11 times per week, about 5 times per week to about 12 times per week, about 6 times per week to about 7 times per week, about 6 times per week to about 8 times per week, about 6 times per week to about 9 times per week, about 6 times per week to about 10 times per week, about 6 times per week to about 11 times per week, about 6 times per week to about 12 times per week, about 7 times per week to about 8 times per week, about 7 times per week to about 9 times per week, about 7 times per week to about 10 times per week, about 7 times per week to about 11 times per week, about 7 times per week to about 12 times per week, about 8 times per week to about 9 times per week, about 8 times per week to about 10 times per week, about 8 times per week to about 11 times per week, about 8 times per week to about 12 times per week, about 9 times per week to about 10 times per week, about 9 times per week to about 11 times per week, about 9 times per week to about 12 times per week, about 10 times per week to about 11 times per week, about 10 times per week to about 12 times per week, or about 11 times per week to about 12 times per week. In some embodiments, a subject is treated with an effective amount of the cosmetic or pharmaceutical composition about 1 time per week, about 2 times per week, about 3 times per week, about 4 times per week, about 5 times per week, about 6 times per week, about 7 times per week, about 8 times per week, about 9 times per week, about 10 times per week, about 11 times per week, about 12 times per week, about 13 times per week, or about 14 times per week.

In certain embodiments, including pharmaceutical embodiments, a pharmaceutical composition of the disclosure is administered to a subject, for indications including but not limited to: preventing or reducing skin discoloration, comprising applying an effective amount of the cosmetic or pharmaceutical composition to the skin of the subject. In some embodiments, the skin discoloration comprises melanin hyperpigmentation, post-inflammatory hyperpigmentation, chloasma, melasma, age spots (e.g., liver spots, senile lentigines, solar lentigines, sunspots), freckles, or a combination thereof. In some embodiments, the skin discoloration results from a disorder, e.g., an adrenal disorder. In some embodiments, the MC1R peptide antagonists of the disclosure are used to treat skin discoloration caused by Addison's disease.

In some embodiments, a topical cosmetic composition of the disclosure is self-applied or administered by a patient. In certain embodiments, including pharmaceutical embodiments, a cosmetic or pharmaceutical composition of the disclosure is applied or administered by a medical professional, e.g., in a medical office setting.

Lipid Vesicle Compositions of Melanocortin 1 Receptor Antagonist Peptides for Intradermal Delivery In one aspect, provided herein, is a lipid vesicle composition comprising a peptide antagonist of a melanocortin 1 receptor, such as those described herein (e.g., SEQ ID NOs: 1-90). In some embodiments, the lipid vesicle composition comprises lipid vesicles each comprising a lipid bilayer comprising vesicle forming lipids. In some embodiments, the lipid vesicle composition comprises an oil-in-water emulsion entrapped in the lipid vesicles. In some embodiments, the oil-in-water emulsion is stabilized by one or more surfactants. In some embodiments, the peptide antagonist is entrapped in the lipid bilayer and/or the oil-in-water emulsion. In some embodiments, the peptide antagonist is entrapped in the lipid bilayer. In some embodiments, the peptide antagonist is entrapped in the oil-in-water emulsion.

Concentrations of Peptide Antagonist in the Composition

In some embodiments, the peptide antagonist is present in the vesicle composition in an amount of about 0.1 mg/mL to about 50 mg/mL. In some embodiments, the peptide antagonist is present in the vesicle composition in an amount of about 0.1 mg/mL to about 0.5 mg/mL, about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 10 mg/mL, about 0.1 mg/mL to about 20 mg/mL, about 0.1 mg/mL to about 50 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 10 mg/mL, about 0.5 mg/mL to about 20 mg/mL, about 0.5 mg/mL to about 50 mg/mL, about 1 mg/mL to about 2 mg/mL, about 1 mg/mL to about 3 mg/mL, about 1 mg/mL to about 4 mg/mL, about 1 mg/mL to about 5 mg/mL, about 1 mg/mL to about 10 mg/mL, about 1 mg/mL to about 20 mg/mL, about 1 mg/mL to about 50 mg/mL, about 2 mg/mL to about 3 mg/mL, about 2 mg/mL to about 4 mg/mL, about 2 mg/mL to about 5 mg/mL, about 2 mg/mL to about 10 mg/mL, about 2 mg/mL to about 20 mg/mL, about 2 mg/mL to about 50 mg/mL, about 3 mg/mL to about 4 mg/mL, about 3 mg/mL to about 5 mg/mL, about 3 mg/mL to about 10 mg/mL, about 3 mg/mL to about 20 mg/mL, about 3 mg/mL to about 50 mg/mL, about 4 mg/mL to about 5 mg/mL, about 4 mg/mL to about 10 mg/mL, about 4 mg/mL to about 20 mg/mL, about 4 mg/mL to about 50 mg/mL, about 5 mg/mL to about 10 mg/mL, about 5 mg/mL to about 20 mg/mL, about 5 mg/mL to about 50 mg/mL, about 10 mg/mL to about 20 mg/mL, about 10 mg/mL to about 50 mg/mL, or about 20 mg/mL to about 50 mg/mL. In some embodiments, the peptide antagonist is present in the vesicle composition in an amount of about 0.1 mg/mL, about 0.5 mg/mL, about 1 mg/mL, about 2 mg/mL, about 3 mg/mL, about 4 mg/mL, about 5 mg/mL, about 10 mg/mL, about 20 mg/mL, or about 50 mg/mL. In some embodiments, the peptide antagonist is present in the vesicle composition in an amount of at least about 0.1 mg/mL, about 0.5 mg/mL, about 1 mg/mL, about 2 mg/mL, about 3 mg/mL, about 4 mg/mL, about 5 mg/mL, about 10 mg/mL, or about 20 mg/mL. In some embodiments, the peptide antagonist is present in the vesicle composition in an amount of at most about 0.5 mg/mL, about 1 mg/mL, about 2 mg/mL, about 3 mg/mL, about 4 mg/mL, about 5 mg/mL, about 10 mg/mL, about 20 mg/mL, or about 50 mg/mL. In some embodiments, the peptide antagonist is present in the composition in an amount of about 1 mg/mL, about 2 mg/mL, about 3 mg/mL, about 4 mg/mL, or about 5 mg/mL.

Vesicle Forming Lipids

In some embodiments, the vesicle composition comprises one or more vesicle forming lipids. The vesicle forming lipids act to encapsulate portions of the oil-in-water emulsions. In some embodiments, this allows the oil-in-water emulsion to remain stable for a period of time.

The vesicle forming lipids may be any suitable lipids for such a purpose. In some embodiments, the vesicle forming lipids comprise phospholipids, glycolipids, lecithins, ceramides, lysolecithin, lysophosphatidylethanolamine, phosphatidylserine, phosphatidylinositol, sphingomyelin, cardiolipin, phosphatidic acid, cerebroside, or any combination thereof. In some embodiments, the vesicle forming lipids comprise a combination of lipids.

In some embodiments, the vesicle forming lipids comprise phospholipids. In some embodiments, the phospholipids are naturally occurring, semisynthetic, or synthetically prepared, or a mixture thereof. In an embodiment, the phospholipids are one or more esters of glycerol with one or two (equal or different) residues of fatty adds and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), or inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing 12 to 24 carbon atoms, or 14 to 22 carbon atoms; the aliphatic chain may contain one or more unsaturations or is completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Saturated fatty acids such as myristic acid, palmitic acid, stearic acid and arachidic acid may be employed.

In some embodiments, the phospholipid comprises one or more natural phospholipids. In some embodiments, the phospholipid comprises one or more semisynthetic phospholipids. In some embodiments, the semisynthetic phospholipids are the partially or fully hydrogenated derivatives of the naturally occurring lecithins. In some embodiments, the phospholipids include fatty acids di-esters of phosphatidylcholine, ethylphosphatidylcholine, phosphatidylglycerol, phosphatidic acid, phosphatidylethanolamine, phosphatidylserine or of sphingomyelin. In some embodiments, the phospholipids include hydrogenated phosphatidylcholine (e.g., Sunlipon 90H). In some embodiments, the phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroylphosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoylphosphatidylethanolamine (DMPE), dipalmitoylphosphatidylethanolamine (DPPE), distearoyl phosphatidyl-ethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoylphosphatidylinositol (DOPI).

In some embodiments, the vesicle forming lipids are present in an amount of about 0.5% to about 25% (w/w) of the composition. In some embodiments, the vesicle forming lipids are present in an amount of about 0.5% to about 2%, about 0.5% to about 5%, about 0.5% to about 8%, about 0.5% to about 10%, about 0.5% to about 12%, about 0.5% to about 15%, about 0.5% to about 20%, about 0.5% to about 25%, about 2% to about 5%, about 2% to about 8%, about 2% to about 10%, about 2% to about 12%, about 2% to about 15%, about 2% to about 20%, about 2% to about 25%, about 5% to about 8%, about 5% to about 10%, about 5% to about 12%, about 5% to about 15%, about 5% to about 20%, about 5% to about 25%, about 8% to about 10%, about 8% to about 12%, about 8% to about 15%, about 8% to about 20%, about 8% to about 25%, about 10% to about 12%, about 10% to about 15%, about 10% to about 20%, about 10% to about 25%, about 12% to about 15%, about 12% to about 20%, about 12% to about 25%, about 15% to about 20%, about 15% to about 25%, or about 20% to about 25% (w/w) of the composition. In some embodiments, the vesicle forming lipids are present in an amount of about 0.5%, about 2%, about 5%, about 8%, about 10%, about 12%, about 15%, about 20%, or about 25%. In some embodiments, the vesicle forming lipids are present in an amount of at least about 0.5%, about 2%, about 5%, about 8%, about 10%, about 12%, about 15%, or about 20% (w/w) of the composition. In some embodiments, the vesicle forming lipids are present in an amount of at most about 2%, about 5%, about 8%, about 10%, about 12%, about 15%, about 20%, or about 25% (w/w) of the composition.

In some embodiments, the vesicle forming lipids are present in an amount of about 5% to about 15% (w/w) of the composition. In some embodiments, the vesicle forming lipids are present in an amount of about 5% to about 8%, about 5% to about 9%, about 5% to about 10%, about 5% to about 11%, about 5% to about 12%, about 5% to about 13%, about 5% to about 14%, about 5% to about 15%, about 8% to about 9%, about 8% to about 10%, about 8% to about 11%, about 8% to about 12%, about 8% to about 13%, about 8% to about 14%, about 8% to about 15%, about 9% to about 10%, about 9% to about 11%, about 9% to about 12%, about 9% to about 13%, about 9% to about 14%, about 9% to about 15%, about 10% to about 11%, about 10% to about 12%, about 10% to about 13%, about 10% to about 14%, about 10% to about 15%, about 11% to about 12%, about 11% to about 13%, about 11% to about 14%, about 11% to about 15%, about 12% to about 13%, about 12% to about 14%, about 12% to about 15%, about 13% to about 14%, about 13% to about 15%, or about 14% to about 15%. In some embodiments, the vesicle forming lipids are present in an amount of about 5%, about 8%, about 9%, about 10%, about 11%, about 12%, about 13%, about 140%, or about 15% (w/w) of the composition. In some embodiments, the vesicle forming lipids are present in an amount of at least about 5%, about 8%, about 9%, about 10%, about 11%, about 12%, about 13%, or about 14% (w/w) of the composition. In some embodiments, the vesicle forming lipids are present in an amount of at most about 8%, about 9%, about 10%, about 11%, about 12%, about 13%, about 14%, or about 15% (w/w) of the composition.

In some embodiments, the composition comprises a short chain polyol. In some embodiments, the short chain polyol acts to enhance the stability of the resulting lipid vesicles. In some embodiments, the short chain polyol is a $C_2$-$C_4$ polyol comprising two or three alcohol groups. In some embodiments, the short chain polyol is propylene glycol. In some embodiments, the composition comprises propylene glycol.

In some embodiments, the propylene glycol is present in an amount of about 0.5% to about 25% (w/w) of the composition. In some embodiments, the propylene glycol is present in an amount of about 0.5% to about 2%, about 0.5% to about 5%, about 0.5% to about 8%, about 0.5% to about 10%, about 0.5% to about 12%, about 0.5% to about 15%, about 0.5% to about 20%, about 0.5% to about 25%, about 2% to about 5%, about 2% to about 8%, about 2% to about 10%, about 2% to about 12%, about 2% to about 15%, about 2% to about 20%, about 2% to about 25%, about 2% to about 5% to about 8%, about 5% to about 10%, about 5% to about 12%, about 5% to about 15%, about 5% to about 20%, about 5% to about 25%, about 8% to about 10%, about 8% to about 12%, about 8% to about 15%, about 8% to about 20%, about 8% to about 25%, about 10% to about 12%, about 10% to about 15%, about 10% to about 20%, about 10% to about 25%, about 12% to about 15%, about 12% to about 20%, about 12% to about 25%, about 15% to about 20%, about 15% to about 25%, or about 20% to about 25%. In some embodiments, the propylene glycol is present in an amount of about 0.5%, about 2%, about 5%, about 8%, about 10%, about 12%, about 15%, about 20%, or about 25%. In some embodiments, the propylene glycol is present in an amount of at least about 0.5%, about 2%, about 5%, about 8%, about 10%, about 12%, about 15%, or about 20%. In some embodiments, the propylene glycol is present in an amount of at most about 2%, about 5%, about 8%, about 10%, about 12%, about 15%, about 20%, or about 25%. In some embodiments, the propylene glycol is present in an amount of about 1% to about 10%. In some embodiments, the propylene glycol is present in an amount of about 1% to about 2%, about 1% to about 4%, about 1% to about 6%, about 1% to about 8%, about 1% to about 10%, about 2% to about 4%, about 2% to about 6%, about 2% to about 8%, about 2% to about 10%, about 4% to about 6%, about 4% to about 8%, about 4% to about 10%, about 6% to about 8%, about 6% to about 10%, or about 8% to about 10%. In some embodiments, the propylene glycol is present in an amount of about 1%, about 2%, about 4%, about 6%, about 8%, or about 10%. In some embodiments, the propylene glycol is present in an amount of at least about 1%, about 2%, about 4%, about 6%, or about 8%. In some embodiments, the propylene glycol is present in an amount of at most about 2%, about 4%, about 6%, about 8%, or about 10%.

In some embodiments, propylene glycol is present in about the same amount as the vesicle forming lipid. In some embodiments, the ratio of propylene glycol to vesicle forming lipid in the composition is form about 2:1 to about 1:2 (w/w).

Oil Phases

The lipid vesicle compositions provided herein comprise an oil-in-water emulsion. The oil component is selected such that the material is a liquid at operative temperatures (e.g., room temperature) and is non-miscible with water.

Any suitable oil may be used as the oil phase. In some embodiments, the oil comprises a naturally occurring oil. In some embodiments, the naturally occurring oil is derived from one or more plants or plant parts (e.g., seeds or nuts). In some embodiments, the oil is a naturally occurring oil such as olive oil, vegetable oil, sunflower oil, or other similar plant derived oil.

In some embodiments, the oil phase is selected from the group consisting of vegetable oils, mono-, di-, and triglycerides, silicone fluids, mineral oils, and combinations thereof.

In some embodiments, the oil comprises a silicon oil or derivative, such as dimethicone. In some embodiments, the oil silicon oil comprises a siloxane polymer. In some embodiments, the siloxane polymer comprises $C_1$-$C_3$ substituents. In some embodiments, the siloxane is polydimethylsiloxane (PDMS). In some embodiments, the oil is a mixture which comprises a silicon oil (e.g., dimethicone) as a smaller component. In some embodiments, the silicon oil is incorporated in order to enhance the feel of the resulting composition or as a moisturizer. In some embodiments, the oil comprises a silicon oil in an amount of up to about 5%, up to about 4%, up to about 3%, up to about 2%, or up to about 1%. In some embodiments, the silicon oil is present in an amount of from about 0.1% to about 2% (w/w) of the composition. In some embodiments, the silicon oil is present in an amount of about 0.5%, about 0.6%, about 0.7%, about 0.8%, about 0.9% or about 1%.

In some embodiments, the oils are present in an amount of about 1% to about 35% (w/w) of the composition. In some embodiments, the oils are present in an amount of about 1% to about 5%, about 1% to about 10%, about 1% to about 15%, about 1% to about 20%, about 1% to about 25%, about 1% to about 30%, about 1% to about 35%, about 5% to about 10%, about 5% to about 15%, about 5% to about 20%, about 5% to about 25%, about 5% to about 30%, about 5% to about 35%, about 10% to about 15%, about 10% to about 20%, about 10% to about 25%, about 10% to about 30%, about 10% to about 35%, about 15% to about 20%, about 15% to about 25%, about 15% to about 30%, about 15% to about 35%, about 20% to about 25%, about 20% to about 30%, about 20% to about 35%, about 25% to about 30%, about 25% to about 35%, or about 30% to about 35%. In some embodiments, the oils are present in an amount of about 1%, about 5%, about 10%, about 15%, about 20%, about 25%, about 30%, or about 35%. In some embodiments, the oils are present in an amount of at least about 1%, about 5%, about 10%, about 15%, about 20%, about 25%, or about 30%. In some embodiments, the oils are present in an amount of at most about 5%, about 10%, about 15%, about 20%, about 25%, about 30%, or about 35%. In some embodiments, the oils are present in an amount of about 5% to about 15%. In some embodiments, the oils are present in an amount of about 5% to about 8%, about 5% to about 9%, about 5% to about 10%, about 5% to about 11%, about 5% to about 12%, about 5% to about 13%, about 5% to about 14%, about 5% to about 15%, about 8% to about 9%, about 8% to about 10%, about 8% to about 11%, about 8% to about 12%, about 8% to about 13%, about 8% to about 14%, about 8% to about 15%, about 9% to about 10%, about 9% to about 11%, about 9% to about 12%, about 9% to about 13%, about 9% to about 14%, about 9% to about 15%, about 10% to about 11%, about 10% to about 12%, about 10% to about 13%, about 10% to about 14%, about 10% to about 15%, about 11% to about 12%, about 11% to about 13%, about 11% to about 14%, about 11% to about 15%, about 12% to about 13%, about 12% to about 14%, about 12% to about 15%, about 13% to about 14%, about 13% to about 15%, or about 14% to about 15%. In some embodiments, the oils are present in an amount of about 5%, about 8%, about 900, about 10%, about 11%, about 12%, about 13%, about 14%, or about 15%. In some embodiments, the oils are present in an amount of at least about 5%, about 8%, about 900, about 10%, about 11%, about 12%, about 13%, or about 14%. In some embodiments, the oils are present in an amount of at most about 8%, about 9%, about 10%, about 11%, about 120%, about 13%, about 14%, or about 15%.

In some embodiments, the oil comprises one or more triglycerides. In some embodiments the triglyceride is a medium chain triglyceride. In some embodiments, the medium chain triglyceride comprises fatty acid esters having a chain length of $C_6$-$C_{12}$.

In some embodiments, the triglyceride is present in an amount of about 1% to about 35% (w/w) of the composition. In some embodiments, the triglyceride is present in an amount of about 1% to about 5%, about 1% to about 10%, about 1% to about 15%, about 1% to about 20%, about 1% to about 25%, about 1% to about 30%, about 1% to about 35%, about 5% to about 10%, about 5% to about 15%, about 5% to about 20%, about 5% to about 25%, about 5% to about 30%, about 5% to about 35%, about 10% to about 15%, about 10% to about 20%, about 10% to about 25%, about 10% to about 30%, about 10% to about 35%, about 15% to about 20%, about 15% to about 25%, about 15% to about 30%, about 15% to about 35%, about 20% to about 25%, about 20% to about 30%, about 20% to about 35%, about 25% to about 30%, about 25% to about 35%, or about 30% to about 35%. In some embodiments, the triglyceride is present in an amount of about 1%, about 1.5%, about 2%, about 2.5%, about 3%, about 3.5%, about 4%, about 4.5%, about 5%, about 10%, about 15%, about 20%, about 25%, about 30%, or about 35%. In some embodiments, the triglyceride is present in an amount of at least about 1%, about 1.5%, about 2%, about 2.5%, about 3%, about 3.5%, about 400 about 4.5%, about 5%, about 10%, about 15%, about 20%, about 25%, or about 30%. In some embodiments, the triglyceride is present in an amount of at most about 1.5%, about 2%, about 2.5%, about 3%, about 3.5%, about 4%, about 4.5%, about 5%, about 10%, about 15%, about 20%, about 25%, about 30%, or about 35%.

In some embodiments, the oil phase of the lipid vesicle and/or the lipid vesicle portion of the composition comprises a sterol. In some embodiments, the sterol is cholesterol. In some embodiments, the cholesterol may be plant-derived cholesterol. In some embodiments, the plant-derived cholesterol may be PhytoChol®, SyntheChol®, or any other plant-derived cholesterol (e.g., Avanti #700100), or any combination thereof. In some embodiments, the sterol may be phytosterol or a derivative thereof. In some embodiments, the phytosterol or derivative thereof may be Phytosterol MM, Advasterol™ 90 IP or 95 IP F, NET Sterol-ISO, canola sterols, sitosterol 700095, lanosterol-95, brassicasterol, or any combination thereof.

In some embodiments, the sterol is present in an amount of about 1% to about 5% (w/w) of the composition. In some embodiments, the sterol is present in an amount of about 1% to about 1.5%, about 1% to about 2%, about 1% to about 2.5%, about 1% to about 3%, about 1% to about 4%, about 1% to about 5%, about 1.5% to about 2%, about 1.5% to about 2.5%, about 1.5% to about 3%, about 1.5% to about 4%, about 1.5% to about 5%, about 2% to about 2.5%, about 2% to about 3%, about 2% to about 4%, about 2% to about 5%, about 2.5% to about 3%, about 2.5% to about 4%, about 2.5% to about 5%, about 3% to about 4%, about 3% to about 5%, or about 4% to about 5% (w/w) of the composition. In some embodiments, the sterol is present in an amount of about 1%, about 1.5%, about 2%, about 2.5%, about 3%, about 4%, or about 5% (w/w) of the composition. In some embodiments, the sterol is present in an amount of at least about 1%, about 1.5%, about 2%, about 2.5%, about 3%, or about 4% (w/w) of the composition. In some embodiments, the sterol is present in an amount of at most about 1.5%, about 2%, about 2.5%, about 3%, about 4%, or about 5% (w/w) of the composition.

Penetration Enhancers

In some embodiments, the lipid vesicle compositions comprise one or more penetration enhancers. Permeation enhancers act to increase the amount of penetration of an anionic polymer material, a peptide, or a combination thereof through one or more layers of skin when applied to the skin of an individual.

In some embodiments, the penetration enhancer is included in the oil-in-water emulsion of the composition. In some embodiments, the penetration enhancer is included in the lipid bilayer of the composition.

There are many types of penetration enhancing agents that may be employed. In some embodiments, the penetration enhancing agent comprising an ionic surfactant, a nonionic surfactant, or a combination thereof.

In some embodiments, the penetration enhancing agent comprises a non-ionic surfactant or a combination of non-ionic surfactants. In some embodiments, the penetration enhancing agent is a single non-ionic surfactant. In some embodiments, the penetration enhancing agent is a combination of at least 2, 3, 4, or more non-ionic surfactants. In some embodiments, the penetration enhancing agent is a combination 2 non-ionic surfactants. In some embodiments, the penetration enhancing agent is a combination 3 non-ionic surfactants.

In some embodiments, the non-ionic surfactant or combination of non-ionic surfactants is selected from polyethylene glycol ethers of fatty alcohols, sorbitan esters, polysorbates, and polyethylene glycol fatty acid esters and combinations thereof.

In some embodiments, the combination of non-ionic surfactants is a combination of a polyethylene glycol ether of a fatty alcohol and a sorbitan ester. In some embodiments, the combination of non-ionic surfactants is a combination of a polyethylene glycol ethers of fatty alcohol and a polysorbate. In some embodiments, the combination of non-ionic surfactants is a combination of a polyethylene glycol ethers of fatty alcohol and a sorbitan ester. In some embodiments, the combination of non-ionic surfactants is a combination of a polyethylene glycol ethers of fatty alcohol and a polyethylene glycol fatty acid ester. In some embodiments, the combination of non-ionic surfactants is a combination of a polyethylene glycol ether of a fatty alcohol, a sorbitan ester, and a polysorbate. In some embodiments, the combination of non-ionic surfactants is a combination of a polyethylene glycol ether of a fatty alcohol, a sorbitan ester, and a polyethylene glycol fatty acid ester. In some embodiments, the combination of non-ionic surfactants is a combination of a polyethylene glycol ether of a fatty alcohol, a polysorbate, and a polyethylene glycol fatty acid ester.

In some embodiments, the combination of non-ionic surfactants comprises a polyethylene glycol fatty acid ester and a sorbitan ester. In some embodiments, the combination of non-ionic surfactants comprises a polyethylene glycol fatty acid ester and a polysorbate. In some embodiments, the combination of non-ionic surfactants is a combination of a polyethylene glycol fatty acid ester, a polysorbate, and a sorbitan ester.

In some embodiments, the non-ionic surfactant comprises a polyethylene glycol (PEG) ether of a fatty alcohol. In some embodiments, the PEG ether of the fatty alcohol comprises from about 2 to about 8 PEG groups and a $C_{12}$-$C_{22}$ fatty alcohol. In some embodiments, the polyethylene glycol ether of a fatty alcohol comprises diethylene glycol hexadecyl ether, 2-(2-octadecoxyethoxy)ethanol, diethylene glycol monooleyl ether, polyoxyethylene (2) oleyl ether, polyoxyethylene (3) oleyl ether, or polyoxyethylene (5) oleyl ether, or any combination thereof.

In some embodiments, the polyethylene glycol ether of a fatty alcohol comprises 2-(2-octadecoxyethoxy)ethanol. In some embodiments, the PEG ether of a fatty alcohol is super refined Brij® 02 or a derivative thereof.

In some embodiments, the PEG ether of the fatty alcohol is present in an amount of from about 0.5% to about 10% (w/w) of the composition. In some embodiments, the PEG ether of the fatty alcohol is present in an amount of about 0.5% to about 2.5%. In some embodiments, the PEG ether of the fatty alcohol is present in an amount of about 0.5% to about 0.8%, about 0.5% to about 1%, about 0.5% to about 1.2%, about 0.5% to about 1.5%, about 0.5% to about 2%, about 0.5% to about 2.5%, about 0.8% to about 1%, about 0.8% to about 1.2%, about 0.8% to about 1.5%, about 0.8% to about 2%, about 0.8% to about 2.5%, about 1% to about 1.2%, about 1% to about 1.5%, about 1% to about 2%, about 1% to about 2.5%, about 1.2% to about 1.5%, about 1.2% to about 2%, about 1.2% to about 2.5%, about 1.5% to about 2%, about 1.5% to about 2.5%, or about 2% to about 2.5%. In some embodiments, the PEG ether of the fatty alcohol is present in an amount of about 0.5%, about 0.8%, about 1%, about 1.2%, about 1.5%, about 2%, or about 2.5%. In some embodiments, the PEG ether of the fatty alcohol is present in an amount of at least about 0.5%, about 0.8%, about 1%, about 1.2%, about 1.5%, or about 2%. In some embodiments, the PEG ether of the fatty alcohol is present in an amount of at most about 0.8%, about 1%, about 1.2%, about 1.5%, about 2%, or about 2.5%.

In some embodiments, the non-ionic surfactant comprises a fatty acid ester. In some embodiments, the non-ionic surfactant comprises PPG benzyl ether myristate, ethylhexyl stearate, isostearyl isostearate (e.g., Crodamol ISIS), myristyl myristate (e.g., Crodamol MM), glyceryl stearate (e.g., Crodamol GMS, Cithrol GMS). In some embodiments, the non-ionic surfactant comprises a sorbitan ester. In some embodiments, the sorbitan ester is a fatty acid ester. In some embodiments, the sorbitan ester is a $C_{12}$-$C_{22}$ fatty acid ester. In some embodiments, the sorbitan ester comprises sorbitan monolaurate, sorbitan monopalmitate, sorbitan monostearate, sorbitan monooleate, sorbitan trioleate, sorbitan sesquioleate, or sorbitan isostearate, or any combinations thereof. In some embodiments, the sorbitan ester comprises sorbitan monolaurate. In some embodiments, the sorbitan ester comprises sorbitan monopalmitate. In some embodiments, the sorbitan ester comprises sorbitan monostearate. In some embodiments, the sorbitan ester comprises sorbitan monooleate. In some embodiments, the sorbitan ester comprises sorbitan trioleate. In some embodiments, the sorbitan ester comprises sorbitan sesquioleate. In some embodiments, the sorbitan ester comprises sorbitan isostearate.

In some embodiments, the sorbitan ester is present in an amount of about 0.1% to about 2.5% (w/w) of the composition. In some embodiments, the sorbitan ester is present in an amount of about 0.1% to about 0.3%, about 0.1% to about 0.5%, about 0.1% to about 0.8%, about 0.1% to about 1%, about 0.1% to about 1.2%, about 0.1% to about 1.5%, about 0.1% to about 2%, about 0.1% to about 2.5%, about 0.30% to about 0.5%, about 0.3% to about 0.8%, about 0.3% to about 1%, about 0.3% to about 1.2%, about 0.3% to about 1.5%, about 0.3% to about 2%, about 0.3% to about 2.5%, about 0.5% to about 0.8%, about 0.5% to about 1%, about 0.5% to about 1.2%, about 0.5% to about 1.5%, about 0.5% to about 2%, about 0.5% to about 2.5%, about 0.8% to about 1%, about 0.8% to about 1.2%, about 0.8% to about 1.5%, about 0.8% to about 2%, about 0.8% to about 2.5%, about 1% to about 1.2%, about 1% to about 1.5%, about 1% to about 2%, about 1% to about 2.5%, about 1.2% to about 1.5%, about 1.2% to about 2%, about 1.2% to about 2.5%, about 1.5% to about 2%, about 1.5% to about 2.5%, or about 2% to about 2.5%. In some embodiments, the sorbitan ester is present in an amount of about 0.1%, about 0.3%, about 0.5%, about 0.8%, about 1%, about 1.2%, about 1.5%, about 2%, or about 2.5%. In some embodiments, the sorbitan ester is present in an amount of at least about 0.1%, about 0.3%, about 0.5%, about 0.8%, about 1%, about 1.2%, about 1.5%, or about 2%. In some embodiments, the sorbitan ester is present in an amount of at most about 0.1%, about 0.3%, about 0.5%, about 0.8%, about 1%, about 1.2%, about 1.5%, about 2%, or about 2.5%.

In some embodiments, the non-ionic surfactant comprises a polysorbate. In some embodiments, the polysorbate comprises polysorbate 20, polysorbate 21, polysorbate 40, polysorbate 60, polysorbate 80, polysorbate 85, or any combination thereof. In some embodiments, the polysorbate is polysorbate 80. In some embodiments, the polysorbate is polysorbate 20.

In some embodiments, the polysorbate is present in an amount of about 0.1% to about 2.5% (w/w) of the composition. In some embodiments, the polysorbate is present in an amount of about 0.1% to about 0.2%, about 0.1% to about 0.3%, about 0.1% to about 0.5%, about 0.1% to about 0.8%, about 0.1% to about 1%, about 0.1% to about 1.2%, about 0.1% to about 1.5%, about 0.1% to about 2%, about 0.1% to about 2.5%, about 0.2% to about 0.3%, about 0.2% to about 0.5%, about 0.2% to about 0.8%, about 0.2% to about 1%, about 0.2% to about 1.2%, about 0.2% to about 1.5%, about 0.2% to about 2%, about 0.2% to about 2.5%, about 0.3% to about 0.5%, about 0.3% to about 0.8%, about 0.3% to about 1%, about 0.3% to about 1.2%, about 0.3% to about 1.5%, about 0.3% to about 2%, about 0.3% to about 2.5%, about 0.5% to about 0.8%, about 0.5% to about 1%, about 0.5% to about 1.2%, about 0.5% to about 1.5%, about 0.5% to about 2%, about 0.5% to about 2.5%, about 0.8% to about 1%, about 0.8% to about 1.2%, about 0.8% to about 1.5%, about 0.8% to about 2%, about 0.8% to about 2.5%, about 1% to about 1.2%, about 1% to about 1.5%, about 1% to about 2%, about 1% to about 2.5%, about 1.2% to about 1.5%, about 1.2% to about 2%, about 1.2% to about 2.5%, about 1.5% to about 2%, about 1.5% to about 2.5%, or about 2% to about 2.5%. In some embodiments, the polysorbate is present in an amount of about 0.1%, about 0.2%, about 0.3%, about 0.5%, about 0.8%, about 1%, about 1.2%, about 1.5%, about 2%, or about 2.5%. In some embodiments, the polysorbate is present in an amount of at least about 0.1%, about 0.2%, about 0.3%, about 0.5%, about 0.8%, about 1%, about 1.2%, about 1.5%, or about 2%. In some embodiments, the polysorbate is present in an amount of at most about 0.2%, about 0.3%, about 0.5%, about 0.8%, about 1%, about 1.2%, about 1.5%, about 2%, or about 2.5%.

In some embodiments, the non-ionic surfactant comprises a polyethylene glycol (PEG) fatty acid ester. In some embodiments, the PEG fatty acid ester is a PEG chain of about 2-8 subunits comprising $C_8$-$C_{22}$ fatty acids affixed to each terminal hydroxyl to form the fatty acid ester. In some embodiments, the PEG fatty acid ester comprises PEG-8 dilaurate, PEG-4 dilaurate, PEG-4 laurate, PEG-8 dioleate, PEG-8 distearate, PEG-8 distearate, PEG-7 glyceryl cocoate, and PEG-20 almond glycerides, or any combination thereof. In some embodiments, the PEG fatty acid ester is PEG-4 dilaurate.

In some embodiments, the PEG fatty acid ester is present in an amount of about 0.5% to about 2.5% (w/w) of the composition. In some embodiments, the PEG fatty acid ester is present in an amount of about 0.5% to about 0.8%, about 0.5% to about 1%, about 0.5% to about 1.2%, about 0.5% to about 1.5%, about 0.5% to about 2%, about 0.5% to about 2.5%, about 0.8% to about 1%, about 0.8% to about 1.2%, about 0.8% to about 1.5%, about 0.8% to about 2%, about 0.8% to about 2.5%, about 1% to about 1.2%, about 1% to about 1.5%, about 1% to about 2%, about 1% to about 2.5%, about 1.2% to about 1.5%, about 1.2% to about 2%, about 1.2% to about 2.5%, about 1.5% to about 2%, about 1.5% to about 2.5%, or about 2% to about 2.5%. In some embodiments, the PEG fatty acid ester is present in an amount of about 0.5%, about 0.8%, about 1%, about 1.2%, about 1.5%, about 2%, or about 2.5%. In some embodiments, the PEG fatty ester is present in an amount of at least about 0.5%, about 0.8%, about 1%, about 1.2%, about 1.5%, or about 2%. In some embodiments, the PEG fatty acid ester is present in an amount of at most about 0.8%, about 1%, about 1.2%, about 1.5%, about 2%, or about 2.5%.

In some embodiments, the non-ionic surfactant has a hydrophobic-lipophilic balance (HLB) of about 10 or less. In some embodiments, the non-ionic surfactant may be Cithrol GMS 40. In some embodiments, the composition comprises a plurality of non-ionic surfactants, each having an HLB of about 10 or less. In some embodiments, the non-ionic surfactant with an HLB of 10 or less is selected from the Table 1, or any combination thereof.

In some embodiments, the non-ionic surfactant or combination of non-ionic surfactants are present in an amount of about 0.5% to about 10% (w/w) of the composition. In some embodiments, the non-ionic surfactant or combination of non-ionic surfactants are present in an amount of about 0.5% to about 1%, about 0.5% to about 1.5%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 10%, about 1% to about 1.5%, about 1% to about 2%, about 1% to about 3%, about 1% to about 4%, about 1% to about 5%, about 1% to about 6%, about 1% to about 7%, about 1% to about 8%, about 1% to about 10%, about 1.5% to about 2%, about 1.5% to about 3%, about 1.5% to about 4%, about 1.5% to about 5%, about 1.5% to about 6%, about 1.5% to about 7%, about 1.5% to about 8%, about 1.5% to about 10%, about 2% to about 3%, about 2% to about 4%, about 2% to about 5%, about 2% to about 6%, about 2% to about 7%, about 2% to about 8%, about 2% to about 10%, about 3% to about 4%, about 3% to about 5%, about 3% to about 6%, about 3% to about 7%, about 3% to about 8%, about 3% to about 10%, about 4% to about 5%, about 4% to about 6%, about 4% to about 7%, about 4% to about 8%, about 4% to about 10%, about 5% to about 6%, about 5% to about 7%, about 5% to about 8%, about 5% to about 10%, about 6% to about 7%, about 6% to about 8%, about 6% to about 10%, about 7% to about 8%, about 7% to about 10%, or about 8% to about 10%. In some embodiments, the non-ionic surfactant or combination of non-ionic surfactants are present in an amount of about 0.5%, about 1%, about 1.5%, about 2%, about 3%, about 4%, about 5%, about 6%, about 7%, about 8%, or about 10%. In some embodiments, the non-ionic surfactant or combination of non-ionic surfactants are present in an amount of at least about 0.5%, about 1%, about 1.5%, about 2%, about 3%, about 4%, about 5%, about 6%, about 7%, or about 8%. In some embodiments, the non-ionic surfactant or combination of non-ionic surfactants are present in an amount of at most about 1%, about 1.5%, about 2%, about 3%, about 4%, about 5%, about 6%, about 7%, about 8%, or about 10%.

In some embodiments, the composition comprises a non-ionic surfactant in the oil-in-water emulsion, the lipid bilayer, or both. In some embodiments, the composition comprises a non-ionic surfactant in the oil-in-water emulsion. In some embodiments, the composition comprises a non-ionic surfactant in the lipid bilayer. In some embodiments, the composition comprises a non-ionic surfactant in the oil-in-water emulsion and the lipid bilayer, wherein the composition comprises two or more different non-ionic surfactants.

In some embodiments, the penetration enhancing agent comprises a salicylate ester or a nicotinate ester. In some embodiments, the ester is a $C_1$-$C_6$ alkyl ester or a benzyl ester. In some embodiments, the penetration enhancing agent comprises methyl salicylate or benzyl nicotinate. In some embodiments, the penetration enhancing agent is a nicotinate ester present in an amount of up to about 0.1%, 0.5%, 1%, 2%, or 3% (w/w) of the composition. In some embodiments, the nicotinate ester is present in an amount of from about 0.1% to about 3%, about 0.1% to about 2%, or about 0.1% to about 1%.

In some embodiments, the penetration enhancing agent comprises a fatty acid acylated amino acid. In some embodiments, the fatty acid acylated amino acid is lysine. In some embodiments, the lysine is mono-acylated with a fatty acid. In some embodiments, the penetration enhancing agent is monolauryl lysine. In some embodiments, the lysine is di-acylated. In some embodiments, the penetration enhancing agent is dipalmitoyllysine. In some embodiments, the fatty acylated amino acid is present in an amount of about 1%, about 2%, about 3%, about 4%, or about 5% (w/w) of the composition. In some embodiments, the fatty acylated amino acid is present in an amount of at least about 1%, about 2%, about 3%, about 4%, or about 5% (w/w) of the composition. In some embodiments, the fatty acylated amino acid is present in an amount of up to about 1%, up to about 2%, up to about 3%, up to about 4%, or up to about 5% (w/w) of the composition. In some embodiments, the fatty acylated amino acid is present in an amount of from about 0.1% to about 5%, from about 0.1% to about 4%, from about 0.1% to about 3%, from about 0.1% to about 2%, from about 0.5% to about 5%, from about 0.5% to about 4%, from about 0.5% to about 3%, from about 0.5% to about 2%, from about 1% to about 5%, from about 1% to about 4%, from about 1% to about 3%, from about 1% to about 2%, or from about 1.5% to about 2.5%.

In some embodiments, the non-ionic surfactant has a hydrophobic-lipophilic balance (HLB) of about 10 or less. In some embodiments, the composition comprises a plurality of non-ionic surfactants, each having an HLB of about 10 or less. In some embodiments, the non-ionic surfactant with an HLB of 10 or less is selected from the Table A below, or any combination thereof.

TABLE A

| Category | |
| --- | --- |
| INCI/Chemical name | Properties |
| Ceteth-2 ®(Diethylene glycol hexadecyl ether) | HLB = 5.3 |
| Steareth-2 ® (2-(2-octadecoxyethoxy)ethanol) | HLB = 4.9 |
| Oleth-2 ® (Polyoxyethylene (2) Oleyl Ether/Diethylene glycol monooleyl ether) | HLB = 4.9 |
| Oleth-3 ®(Polyoxyethylene (3) Oleyl Ether) | HLB = 6.6 |
| Oleth-5 ®(Polyoxyethylene (5) Oleyl Ether) | HLB = 9 |
| Polysorbate 61 ® | HLB = 9.6 |
| Sorbitan monolaurate | HLB = 8.6 |
| Sorbitan monopalmitate | HLB = 6.7 |
| Sorbitan monostearate | HLB = 4.7 |
| Sorbitan monooleate | HLB = 4.3 |
| Sorbitan trioleate | HLB = 1.8 |
| Sorbitan sesquioleate | HLB = 3.7 |
| Sorbitan Isostearate | HLB = 4.7 |
| PEG-8 dilaurate | HLB = 10 |
| PEG-4 dilaurate (Polyoxyethylene (8) dilaurate) | HLB = 6 |
| PEG-4 laurate ((Polyoxyethylene (4) dilaurate) | HLB = 9 |
| PEG-8 dioleate | HLB = 7.2 |
| PEG-8 distearate | HLB = 8 |
| PEG-7 glyceryl cocoate | HLB = 10 |
| PEG-20 almond glycerides | HLB = 10 |
| Propylene glycol isostearate | HLB = 2.5 |
| Glycol stearate | HLB = 2.9 |
| Glyceryl stearate | HLB = 3.8 |
| Glyceryl stearate SE | HLB = 5.8 |
| Glyceryl laurate | HLB = 5.2 |

TABLE A-continued

| Category | |
| --- | --- |
| INCI/Chemical name | Properties |
| Glyceryl caprylate | HLB = 5-6 |
| PEG-30 dipolyhydroxy-stearate | HLB = 5.5 |
| Glycol distearate | HLB = 1, and |
| Phospholipid/lecithin | HLB = 4-10 |

In some embodiments, the non-ionic surfactant has a hydrophobic-lipophilic balance (HLB) of about 10 or more. In some embodiments, the composition comprises a plurality of non-ionic surfactants, each having an HLB of about 10 or more.

In some embodiments, the non-ionic surfactant or combination of non-ionic surfactants are present in an amount of about 0.5% to about 10% (w/w) of the composition. In some embodiments, the non-ionic surfactant or combination of non-ionic surfactants are present in an amount of about 0.5% to about 1%, about 0.5% to about 1.5%, about 0.5% to about 20%, about 0.5% to about 3%, about 0.5% to about 4%, about 0.5% to about 5%, about 0.5% to about 6%, about 0.5% to about 7%, about 0.5% to about 8%, about 0.5% to about 10%, about 1% to about 1.5%, about 1% to about 2%, about 1% to about 3%, about 1% to about 4%, about 1% to about 5%, about 1% to about 6%, about 1% to about 7%, about 1% to about 8%, about 1% to about 10%, about 1.5% to about 2%, about 1.5% to about 3%, about 1.5% to about 4%, about 1.5% to about 5%, about 1.5% to about 6%, about 1.5% to about 7%, about 1.5% to about 8%, about 1.5% to about 10%, about 2% to about 3%, about 2% to about 4%, about 2% to about 5%, about 2% to about 6%, about 2% to about 7%, about 2% to about 8%, about 2% to about 10%, about 3% to about 4%, about 3% to about 5%, about 3% to about 6%, about 3% to about 7%, about 3% to about 8%, about 3% to about 10%, about 4% to about 5%, about 4% to about 6%, about 4% to about 7%, about 4% to about 8%, about 4% to about 10%, about 5% to about 6%, about 5% to about 7%, about 5% to about 8%, about 5% to about 10%, about 6% to about 7%, about 6% to about 8%, about 6% to about 10%, about 7% to about 8%, about 7% to about 10%, or about 8% to about 10%. In some embodiments, the non-ionic surfactant or combination of non-ionic surfactants are present in an amount of about 0.5%, about 1%, about 1.5%, about 2%, about 3%, about 4%, about 5%, about 6%, about 7%, about 8%, or about 10%. In some embodiments, the non-ionic surfactant or combination of non-ionic surfactants are present in an amount of at least about 0.5%, about 1%, about 1.5%, about 2%, about 3%, about 4%, about 5%, about 6%, about 7%, or about 8%. In some embodiments, the non-ionic surfactant or combination of non-ionic surfactants are present in an amount of at most about 1%, about 1.5%, about 2%, about 3%, about 4%, about 5%, about 6%, about 7%, about 8%, or about 10%.

In some embodiments, the composition comprises a non-ionic surfactant in the oil-in-water emulsion, the lipid bilayer, or both. In some embodiments, the composition comprises a non-ionic surfactant in the oil-in-water emulsion. In some embodiments, the composition comprises a non-ionic surfactant in the lipid bilayer. In some embodiments, the composition comprises a non-ionic surfactant in the oil-in-water emulsion and the lipid bilayer, wherein the composition comprises two or more different non-ionic surfactants.

In some embodiments, the penetration enhancing agent comprises a salicylate ester or a nicotinate ester. In some embodiments, the ester is a $C_1$-$C_6$ alkyl ester or a benzyl ester. In some embodiments, the penetration enhancing agent comprises methyl salicylate or benzyl nicotinate. In some embodiments, the penetration enhancing agent is a nicotinate ester present in an amount of up to about 0.1%, 0.5%, 1%, 2%, or 3% (w/w) of the composition. In some embodiments, the nicotinate ester is present in an amount of from about 0.1% to about 3%, about 0.1% to about 2%, or about 0.1% to about 1%.

Cationic Surfactants

In some embodiments, the composition comprises an ionic surfactant. In some embodiments, the ionic surfactant is a cationic surfactant. In some embodiments, the cationic surfactant is a mono-cationic surfactant, a di-cationic surfactant, or a poly-cationic surfactant.

In some embodiments, the mono-cationic surfactant is used in the composition to form a submicron emulsion prior to formation of a final lipid vesicle composition provided herein (e.g., before the lipid forming vesicles are added). In some embodiments, the mono-cationic surfactant is net-mono-cationic (e.g., a phosphate salt comprising two side chains each with a single cationic functionality, which is partially neutralized by a phosphate anion).

In some embodiments, the mono-cationic surfactant is a fatty-amide derived propylene glycol-diammonium phosphate ester. Fatty-amide derived propylene glycol-diammonium phosphate esters are phospholipids which comprise at least one propylene glycol phosphoester linked to a quaternary ammonium group, which is in turn linked with a fatty acid amide. One non-limiting example of a fatty-amide derived propylene glycol-diammonium phosphate ester is linoleamidopropyl PG-dimonium chloride phosphate. Similar compounds with different fatty acid amide groups attached are also known. In some embodiments, the fatty-amide derived propylene glycol-diammoniom phosphate ester has the structure:

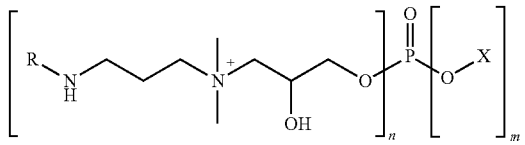

wherein n is an integer from 1 to 3, m is an integer from 0 to 2, wherein the sum of m and n is 3; X is a cation selected from a proton, sodium, potassium, magnesium, and calcium; and R is an acyl group of a $C_8$-$C_{30}$ fatty acid.

In some embodiments, the fatty acid is a $C_{12}$-$C_{24}$ fatty acid. In some embodiments, the fatty acid is an unsaturated fatty acid. In some embodiments, the fatty acid is linoleic acid. In some embodiments, the mono-cationic penetration enhancing agent is linoleamidopropyl PG-dimonium chloride phosphate (e.g., Arlasilk™ PTM, Arlasilk™ EFA).

In some embodiments, the fatty amide derived propylene glycol-diammonium phosphate ester is present in an amount of about 1% to about 10% (w/w) of the composition. In some embodiments, the fatty amide derived propylene glycol-diammonium phosphate ester is present in an amount of about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 9% to about 10%. In some embodiments, the fatty amide derived propylene glycol-diammonium phosphate ester is present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% (w/w) of the composition. In some embodiments, the fatty amide derived propylene glycol-diammonium phosphate ester is present in an amount of at least about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, or about 9.5%. In some embodiments, the fatty amide derived propylene glycol-diammonium phosphate ester is present in an amount of at most about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%.

In some embodiments, the cationic surfactant is a di-cationic penetration enhancing agent. In some embodiments, the di-cationic surfactant is a gemini surfactant. In some embodiments, a gemini surfactant is a surfactant comprising two quaternary amines represented by the formula, wherein each of A and C is independently an optionally substituted $C_6$-$C_{24}$ alkyl group, each R is independently optionally substituted $C_1$-$C_6$ alkyl, and B is an optionally substituted $C_2$-$C_{10}$ alkylene chain. In some embodiments, the each of A and C is a $C_6$-$C_{24}$ saturated or unsaturated hydrocarbon. In some embodiments, the each of A and C is a $C_6$-$C_{24}$ saturated hydrocarbon. In some embodiments, each R is methyl. In some embodiments, B is a saturated $C_2$-$C_{10}$ alkylene chain. In some cases, gemini surfactants follow the nomenclature X—Y—Z, wherein each of X, Y, and Z is an integer representing the number of carbon atoms of each substituent, and Y is the spacer between the two quaternary amines. Thus, for example, a 12-3-12 gemini surfactant has the formula $CH_3(CH_2)_{11}$—[$N^+(CH_3)_2$]—$(CH_2)_3$—[$N^+(CH_3)_2$]—$(CH_2)_{11}CH_3$. In some embodiments, the gemini surfactant is a 10-2-10, 12-2-12, 14-2-14, 10-3-10, 12-3-12, 14-3-14, 10-4-10, 12-4-12, or 14-4-14 gemini surfactant. In some embodiments, the gemini surfactant is a 12-3-12 gemini surfactant.

In some embodiments, the gemini surfactant is present in an amount of about 0.1% to about 1.5% (w/w) of the composition. In some embodiments, the gemini surfactant is present in an amount of about 0.1% to about 0.2%, about 0.1% to about 0.3%, about 0.1% to about 0.5%, about 0.1% to about 0.7%, about 0.1% to about 0.9%, about 0.1% to about 1%, about 0.1% to about 1.2%, about 0.1% to about 1.5%, about 0.2% to about 0.3%, about 0.2% to about 0.5%, about 0.2% to about 0.7%, about 0.2% to about 0.9%, about 0.2% to about 1%, about 0.2% to about 1.2%, about 0.2% to about 1.5%, about 0.3% to about 0.5%, about 0.3% to about 0.7%, about 0.3% to about 0.9%, about 0.3% to about 1%, about 0.3% to about 1.2%, about 0.3% to about 1.5%, about 0.5% to about 0.7%, about 0.5% to about 0.9%, about 0.5% to about 1%, about 0.5% to about 1.2%, about 0.5% to about 1.5%, about 0.7% to about 0.9%, about 0.7% to about 1%, about 0.7% to about 1.2%, about 0.7% to about 1.5%, about 0.9% to about 1%, about 0.9% to about 1.2%, about 0.9% to about 1.5%, about 1% to about 1.2%, about 1% to about 1.5%, or about 1.2% to about 1.5%. In some embodiments, the gemini surfactant is present in an amount of about 0.1%, about 0.2%, about 0.3%, about 0.5%, about 0.7%, about 0.9%, about 1%, about 1.2%, or about 1.5%. In some embodiments, the gemini surfactant is present in an amount of at least about 0.1%, about 0.2%, about 0.3%, about 0.5%, about 0.7%, about 0.9%, about 1%, or about 1.2%. In some embodiments, the gemini surfactant is present in an amount of at most about 0.2%, about 0.3%, about 0.5%, about 0.7%, about 0.9%, about 1%, about 1.2%, or about 1.5%.

In some embodiments, the cationic surfactant comprises a polycationic group. In some embodiments, the polycationic group is a polymer wherein each monomer of the polymer comprises a charged group (e.g., an amino group). In some embodiments, the polycationic group is polylysine. In some embodiments, the polycationic group is polyarginine.

In some cases, the cationic surfactant may comprise an amino acid and a fatty acid. In some cases, the cationic surfactant may be derived from an amino acid and a fatty acid. In some instances, the amino acid may comprise a cationic amino acid, such as lysine, arginine, or histidine. In some instances, the fatty acid may comprise a undecyloyl, lauroyl, tridecyloyl, myristoyl, palmitoyl, or stearoyl group In some examples, the cationic surfactant may comprise lauroyl lysine or lauroyl arginine.

In some embodiments, the polylysine has a molecular weight of from about 1 kDa to about 10 kDa, from about 1 kDa to about 5 kDa, or from about 3 kDa to about 5 kDa. In some embodiments, the polylysine is present in an amount of from about 0.01% to about 1%, from about 0.01% to about 0.5%, from about 0.01% to about 0.2%, from about 0.05% to about 1%, from about 0.05% to about 0.5%, or from about 0.05% to about 0.2% (w/w) of the composition.

Additional Components

In some embodiments, the vesicle composition comprises additional components. In some embodiments, these additional components improve one or more properties of the vesicles without dramatically altering the delivery of an active ingredient. In some cases, the active ingredient comprises a peptide antagonist of a melanocortin 1 receptor. In some embodiments, the peptide antagonist is present in the composition in an amount of about 0.1% to about 1.5% (w/w). In some embodiments, the peptide antagonist is present in an amount of about 0.1% to about 0.2%, about 0.1% to about 0.3%, about 0.1% to about 0.5%, about 0.1% to about 0.7%, about 0.1% to about 0.9%, about 0.1% to about 1%, about 0.1% to about 1.2%, about 0.1% to about 1.5%, about 0.2% to about 0.3%, about 0.2% to about 0.5%, about 0.2% to about 0.7%, about 0.2% to about 0.9%, about 0.2% to about 1%, about 0.2% to about 1.2%, about 0.2% to about 1.5%, about 0.3% to about 0.5%, about 0.3% to about 0.7%, about 0.3% to about 0.9%, about 0.3% to about 1%, about 0.3% to about 1.2%, about 0.3% to about 1.5%, about 0.5% to about 0.7%, about 0.5% to about 0.9%, about 0.5% to about 1%, about 0.5% to about 1.2%, about 0.5% to about 1.5%, about 0.7% to about 0.9%, about 0.7% to about 1%, about 0.7% to about 1.2%, about 0.7% to about 1.5%, about 0.9% to about 1%, about 0.9% to about 1.2%, about 0.9% to about 1.5%, about 1% to about 1.2%, about 1% to about 1.5%, or about 1.2% to about 1.5%. In some embodiments, the peptide antagonist is present in an amount of about 0.1%, about 0.2%, about 0.3%, about 0.5%, about 0.7%, about 0.9%, about 1%, about 1.2%, or about 1.5%. In some embodiments, the peptide antagonist is present in an amount of at least about 0.1%, about 0.2%, about 0.3%, about 0.5%, about 0.7%, about 0.9%, about 1%, or about 1.2%. In some embodiments, the peptide antagonist is present in an amount of at most about 0.2%, about 0.3%, about 0.5%, about 0.7%, about 0.9%, about 1%, about 1.2%, or about 1.5%.

In some embodiments, the vesicle composition further comprises one or more viscosity enhancing agents. In some embodiments, the viscosity enhancing agents thicken the composition for increased stability and/or feel to a user of the vesicle composition. In some embodiments, the viscosity enhancing agents also act as surfactants. In some embodiments, the viscosity enhancing agent comprises one or more of a fatty alcohol, a wax, a fatty ester of glycerol, or any combination thereof. In some embodiments, the fatty alcohol is a $C_8$-$C_{20}$ fatty alcohol. In some embodiments, the fatty alcohol is cetyl alcohol. In some embodiments, the cetyl alcohol is Crodacol C95. In some embodiments, the wax is a naturally occurring or synthetic wax. In some embodiments, the wax is beeswax. In some embodiment, the wax is synthetic beeswax. In some embodiments, the synethetic beeswax is Syncrowax™ BB4. In some embodiments, the synthetic beeswax is non-animal derived beeswax. In some embodiments the non-animal derived beeswax is Syncrowax™ SB1. In some embodiments, the wax comprises jojoba wax, candelilla wax, carnauba wax, or vegetable oil. In some embodiments, the fatty ester of glycerol is a monoester. In some embodiments, the monoester is an ester of a $C_8$-$C_{24}$ fatty acid. In some embodiments, the fatty ester of glycerol is glycerol monostearate.

In some embodiments, the viscosity enhancing agents are present in an amount of from about 0.5% to about 10% (w/w) of the composition. In some embodiments, the viscosity enhancing agents are present in an amount of from about 0.5% to about 5%, about 0.5% to about 5%, about 0.5% to about 4%, about 0.5% to about 3%, or from about 0.5% to about 2% (w/w) of the composition. In some embodiments, the viscosity enhancing agents comprise a fatty alcohol in an amount of up to about 2%, a wax in an amount of up to about 2%, and a fatty ester of glycerol in an amount of up to about 5%. In some embodiments, the fatty alcohol is present in an amount of from about 0.1 to about 1.5%. In some embodiments, the fatty alcohol is present in an amount of about 0.4%. In some embodiments, the wax is present in an amount of from about 0.1% to about 1%. In some embodiments, the wax is present in an amount of about 0.2%. In some embodiments, two or more waxes are each present in an amount of about 0.2%. In some embodiments, the fatty ester of glycerol is present in an amount of from about 0.5% to about 2%.

In some embodiments, the vesicle composition further comprises one or more of a thickener, a preservative, a moisturizer, an emollient, a humectant, or any combination thereof. In some embodiments, the vesicle composition further comprises a thickener. In some embodiments, the vesicle composition further comprises a preservative. In some embodiments, the vesicle composition further comprises a moisturizer. In some embodiments, the vesicle composition further comprises an emollient. In some cases, the emollient may be derived from an amino acid and a fatty acid. In some instances, the amino acid may comprise lysine, arginine, histidine, glutamate, aspartate, or sarcosinate. In some examples, the emollient may comprise lauroyl lysine, lauroyl arginine, isopropyl lauroyl sarcosinate, phytosteryl lauroyl glutamate, behenyl lauroyl glutamate, octyldodecyl lauroyl glutamate, or cholesteryl lauroyl glutamate. In some embodiments, the vesicle composition further comprises a humectant.

In some embodiments, the vesicle composition further comprises an antimicrobial. In some embodiments, the antimicrobial is a paraben ester. In some embodiments, the antimicrobial is methylparaben or propylparaben, or a combination thereof. In some embodiments, the antimicrobial is present in an amount of up to about 1%, up to about 0.9%, up to about 0.8%, up to about 0.7%, up to about 0.6%, up to about 0.5%, up to about 0.4%, up to about 0.3%, up to about 0.2% (w/w) of the composition.

In some embodiments, the vesicle composition further comprises a thickener. In some embodiments, the thickener is an inert polymer material. In some embodiments, the thickener is a siloxane polymer. In some embodiments, the thickener polydimethyl siloxane (PDMS). In some embodiments, the PDMS is present in an amount of up to about 5%, up to about 4%, up to about 3%, up to about 2%, or up to about 1%. In some embodiments, the PDMS is present in an amount of from about 0.1% to about 2% (w/w) of the composition.

In some embodiments, the vesicle composition further comprises a humectant. In some embodiments, the composition comprises glycerol. In some embodiments, the glycerol is present in an amount of from about 0.5% to about 25%, about 0.5% to about 20%, about 0.5% to about 15%, or about 0.5% to about 10% (w/w) of the composition. In some embodiments, the glycerol is present in an amount of about 1% to about 10%. In some embodiments, the glycerol is present in an amount of about 1% to about 2%, about 1% to about 4%, about 1% to about 6%, about 1% to about 8%, about 1% to about 10%, about 2% to about 4%, about 2% to about 6%, about 2% to about 8%, about 2% to about 10%, about 4% to about 6%, about 4% to about 8%, about 4% to about 10%, about 6% to about 8%, about 6% to about 10%, or about 8% to about 10%. In some embodiments, the glycerol is present in an amount of about 1%, about 2%, about 4%, about 6%, about 8%, or about 10%. In some embodiments, the glycerol is present in an amount of at least about 1%, about 2%, about 4%, about 6%, or about 8%. In some embodiments, the glycerol is present in an amount of at most about 2%, about 4%, about 6%, about 8%, or about 10%.

In some embodiments, the vesicle composition further comprises a preservative. In some embodiments, the preservative is a paraben ester. In some embodiments, the preservative is methylparaben or propylparaben, or a combination thereof. In some embodiments, the preservative is present in an amount of up to about 1%, up to about 0.9%, up to about 0.8%, up to about 0.7%, up to about 0.6%, up to about 0.5%, up to about 0.4%, up to about 0.3%, up to about 0.2% (w/w) of the composition. In some embodiments, the preservative is a cosmetic preservative, such as Euxyl® PE 9010 or Spectrastat®. In some embodiments, the preservative comprises a phenoxyethanol/ethylhexylglycerin mixture. In some embodiments, the preservative comprises a blend of caprylhydroxamic acid, caprylyl glycol, and glycerin. In some embodiments, the preservative is present in an amount of up to about 2%, up to about 1.5%, or up to about 1% (w/w) of the composition. In some embodiments, the preservative is present in an amount of from about 0.1% to about 2%, from about 0.1% to about 1.5%, or from about 0.1% to about 1%.

In some embodiments, the preservative is present in an amount of about 0.1%, 0.2%, 0.3%, 0.4%, 0.5%, 0.6%, 0.7%, 0.8%, 0.9%, 1%, 1.1%, 1.2%, 1.3%, 1.4%, or 1.5%.

In some embodiments, an additional component in the lipid vesicle composition may comprise a molecule that can directly or indirectly reduce melanogenesis. In some embodiments, the molecule may directly or indirectly inhibit tyrosinase. In some cases, the additional component is an antioxidant. In some cases, the antioxidant may comprise vitamin C or a derivative thereof. In some instances, the antioxidant may comprise ascorbic acid, ascorbyl palmitate, sodium ascorbyl phosphate, magnesium ascorbyl phosphate, retinyl ascorbate, aminopropyl ascorbyl phosphate (K3 Vita-C), tetrahexyldecyl ascorbate, ascorbyl methylsilanol pectinate (ascorbosilane SP), or a combination thereof. In some embodiments, the antioxidant, such as a vitamin C or derivative thereof, may also aid in collagen synthesis. In some embodiments, the additional component may comprise resorcinol (e.g., 4-butyl resorcinol). In some cases, 4-butyl resorcinol may be used to reduce hyperpigmentation in a layer of the skin, such as the epidermis. In some embodiments, resorcinol is present in the composition in an amount of from about 0.005% to about 0.1%. In some embodiments, resorcinol is present in the composition in an amount of from about 0.005% to about 0.01%, about 0.005% to about 0.02%, about 0.005% to about 0.05%, about 0.005% to about 0.07%, about 0.005% to about 0.1%, about 0.01% to about 0.02%, about 0.01% to about 0.05%, about 0.01% to about 0.07%, about 0.01% to about 0.1%, about 0.02% to about 0.05%, about 0.02% to about 0.07%, about 0.02% to about 0.1%, about 0.05% to about 0.07%, about 0.05% to about 0.1%, or about 0.07% to about 0.1%. In some embodiments, resorcinol is present in the composition in an amount of about 0.005%, about 0.01%, about 0.02%, about 0.05%, about 0.07%, or about 0.1%. In some embodiments, resorcinol is present in the composition in an amount of at least about 0.005%, about 0.01%, about 0.02%, about 0.05%, or about 0.07%. In some embodiments, resorcinol is present in the composition in an amount of at most about 0.01%, about 0.02%, about 0.05%, about 0.07%, or about 0.1%.

In some embodiments, an additional component may comprise one or more vitamins or derivatives thereof. In some cases, the one or more vitamins or derivatives thereof may provide one or more desired effects (e.g., smoothing, toning, moisturizing, brightening, reducing acne, eczema, wrinkles, etc.) when applied to the skin or epidermis. In some instances, the additional component may comprise vitamin B, vitamin C (ascorbic acid), vitamin A (retinol), vitamin E, vitamin D, vitamin F, vitamin K or any derivative thereof. In some examples, the additional component may comprise vitamin B3 (niacin). In some instances, a vitamin B3 derivative may comprise niacinamide. In some examples, the additional component may comprise provitamin B5 (panthenol). In some embodiments, the one or more vitamins or derivatives thereof are present in the composition in an about from about 0.1% to about 2.5% (w/w). In some embodiments, the one or more vitamins or derivatives thereof is present in an amount of about 0.1% to about 0.2%, about 0.1% to about 0.3%, about 0.1% to about 0.5%, about 0.1% to about 0.8%, about 0.1% to about 1%, about 0.1% to about 1.2%, about 0.1% to about 1.5%, about 0.1% to about 2%, about 0.1% to about 2.5%, about 0.2% to about 0.3%, about 0.2% to about 0.5%, about 0.2% to about 0.8%, about 0.2% to about 1%, about 0.2% to about 1.2%, about 0.2% to about 1.5%, about 0.2% to about 2%, about 0.2% to about 2.5%, about 0.3% to about 0.5%, about 0.3% to about 0.8%, about 0.3% to about 1%, about 0.3% to about 1.2%, about 0.3% to about 1.5%, about 0.3% to about 2%, about 0.3% to about 2.5%, about 0.5% to about 0.8%, about 0.5% to about 1%, about 0.5% to about 1.2%, about 0.5% to about 1.5%, about 0.5% to about 2%, about 0.5% to about 2.5%, about 0.8% to about 1%, about 0.8% to about 1.2%, about 0.8% to about 1.5%, about 0.8% to about 2%, about 0.8% to about 2.5%, about 1% to about 1.2%, about 1% to about 1.5%, about 1% to about 2%, about 1% to about 2.5%, about 1.2% to about 1.5%, about 1.2% to about 2%, about 1.2% to about 2.5%, about 1.5% to about 2%, about 1.5% to about 2.5%, or about 2% to about 2.5%. In some embodiments, the one or more vitamins or derivatives thereof is present in an amount of about 0.1%, about 0.2%, about 0.30%, about 0.5%, about 0.8%, about 1%, about 1.2%, about 1.5%, about 2%, or about 2.5%. In some embodiments, the one or more vitamins or derivatives thereof is present in an amount of at least about 0.1%, about 0.2%, about 0.3%, about 0.5%, about 0.8%, about 1%, about 1.2%, about 1.5%, or about 2%. In some embodiments, the one or more vitamins or derivatives thereof is present in an amount of at most about 0.2%, about 0.3%, about 0.50%, about 0.8%, about 1%, about 1.2%, about 1.5%, about 2%, or about 2.5%.

In some aspects, the lipid vesicle composition provided herein comprise an anionic polymer material. The anionic polymer material is desirably one which is compatible with delivery beneath the surface of the skin of a subject. In some embodiments, the anionic polymer material is one which acts as a volumizer or filler after delivery beneath the surface of the skin. In some embodiments, the anionic polymer material acts as a support for another layer of skin (e.g., the epidermis) in order to correct depressions of the skin or restore facial volume.

In some embodiments, the anionic polymer material comprises an anionic polysaccharide. In some embodiments, the anionic polysaccharide is non-sulfated glycosaminoglycan. In some embodiments, the anionic polymeric material is a naturally occurring substance. In some embodiments, the anionic polymeric material naturally occurs in a human. In some embodiments, the anionic polymer material naturally occurs in connective or epithelial tissue in a human. In some embodiments, the anionic polymeric material is hyaluronic acid, or a pharmaceutically acceptable salt thereof. In some embodiments, the anionic polymer material may not be crosslinked in the lipid vesicle composition as described herein.

In some embodiments, the hyaluronic acid is a pharmaceutically acceptable salt of hyaluronic acid. In some embodiments, the salt is the sodium salt, the potassium salt, the magnesium salt, or any combination thereof. In some embodiments, the salt is the sodium salt.

In some embodiments, the anionic polymer material has a molecular weight of from about 5 kDa to about 500 kDa. In some embodiments, the molecular weight is the weight average molecular weight. In some embodiments, the anionic polymeric material has a molecular weight of about 5 kDa to about 500 kDa. In some embodiments, the anionic polymeric material has a molecular weight of about 5 kDa to about 10 kDa, about 5 kDa to about 20 kDa, about 5 kDa to about 50 kDa, about 5 kDa to about 100 kDa, about 5 kDa to about 200 kDa, about 5 kDa to about 250 kDa, about 5 kDa to about 300 kDa, about 5 kDa to about 400 kDa, about 5 kDa to about 500 kDa, about 10 kDa to about 20 kDa, about 10 kDa to about 50 kDa, about 10 kDa to about 100 kDa, about 10 kDa to about 200 kDa, about 10 kDa to about 250 kDa, about 10 kDa to about 300 kDa, about 10 kDa to about 400 kDa, about 10 kDa to about 500 kDa, about 20 kDa to about 50 kDa, about 20 kDa to about 100 kDa, about 20 kDa to about 200 kDa, about 20 kDa to about 250 kDa, about 20 kDa to about 300 kDa, about 20 kDa to about 400 kDa, about 20 kDa to about 500 kDa, about 50 kDa to about 100 kDa, about 50 kDa to about 200 kDa, about 50 kDa to about 250 kDa, about 50 kDa to about 300 kDa, about 50 kDa to about 400 kDa, about 50 kDa to about 500 kDa, about 100 kDa to about 200 kDa, about 100 kDa to about 250 kDa, about 100 kDa to about 300 kDa, about 100 kDa to about 400 kDa, about 100 kDa to about 500 kDa, about 200 kDa to about 250 kDa, about 200 kDa to about 300 kDa, about 200 kDa to about 400 kDa, about 200 kDa to about 500 kDa, about 250 kDa to about 300 kDa, about 250 kDa to about 400 kDa, about 250 kDa to about 500 kDa, about 300 kDa to about 400 kDa, about 300 kDa to about 500 kDa, or about 400 kDa to about 500 kDa. In some embodiments, the anionic polymeric material has a molecular weight of about 5 kDa, about 10 kDa, about 20 kDa, about 50 kDa, about 100 kDa, about 200 kDa, about 250 kDa, about 300 kDa, about 400 kDa, or about 500 kDa. In some embodiments, the anionic polymeric material has a molecular weight of at least about 5 kDa, about 10 kDa, about 20 kDa, about 50 kDa, about 100 kDa, about 200 kDa, about 250 kDa, about 300 kDa, or about 400 kDa. In some embodiments, the anionic polymeric material has a molecular weight of at most about 10 kDa, about 20 kDa, about 50 kDa, about 100 kDa, about 200 kDa, about 250 kDa, about 300 kDa, about 400 kDa, or about 500 kDa.

In some embodiments, the lipid vesicle composition comprises a first and a second anionic polymer material. In some embodiments, the lipid vesicle composition further comprises a third anionic polymer material.

In some embodiments, the first and the second anionic polymer material are the same type. In some embodiments, each of the first and the second anionic polymer material is an anionic polysaccharide. In some embodiments, each of the first and the second anionic polymer is hyaluronic acid.

In cases where the first and second anionic polymer materials are the same type, each anionic polymer material has a different molecular weight. In some embodiments, the first anionic polymer material has a molecular weight of up to about 75 kDa and the second anionic polymer material has a molecule weight of greater than about 75 kDa. In some embodiments, the first anionic polymer material has a molecular weight of up to about 75 kDa and the second anionic polymer material has a molecular weight of greater than about 75 kDa.

In cases where the lipid vesicle comprises a first and second anionic polymer material, each component may be included in a different amount. In some embodiments, the first and second anionic polymer material are present in about the same amount. In some embodiments, the ratio of the fist and the second anionic material is about 10:1, 9:1. 8:1, 7:1, 6:1, 5:1, 4:1, 3:1, 3:2, 2:1, or about 1:1.

In some embodiments, wherein the composition comprises a first, second, and third anionic polymer material, each of the anionic polymer materials can be of the same type (e.g., three different molecular weights of hyaluronic acid). In some embodiments, the composition comprises a first, second, and a third anionic polymer material, wherein the first anionic polymer material has a molecular weight of from about 5 kDa to about 20 kDa, the second anionic polymer has a molecular weight of from about 20 kDa to about 75 kDa, and the third anionic polymer material has a molecular weight of greater than about 75 kDa. In some embodiments, each of the three anionic polymer materials is present in about the same amount.

In some embodiments, the anionic polymer material is present in an amount of from about 0.01 mg/mL to about 10 mg/mL. In some embodiments, the anionic polymer material is present in an amount of about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 1.25 mg/mL, about 0.01 mg/mL to about 1.5 mg/mL, about 0.01 mg/mL to about 1.75 mg/mL, about 0.01 mg/mL to about 2 mg/mL, about 0.01 mg/mL to about 5 mg/mL, about 0.01 mg/mL to about 10 mg/mL, about 0.05 mg/mL to about 0.1 mg/mL, about 0.05 mg/mL to about 0.5 mg/mL, about 0.05 mg/mL to about 1 mg/mL, about 0.05 mg/mL to about 1.25 mg/mL, about 0.05 mg/mL to about 1.5 mg/mL, about 0.05 mg/mL to about 1.75 mg/mL, about 0.05 mg/mL to about 2 mg/mL, about 0.05 mg/mL to about 5 mg/mL, about 0.05 mg/mL to about 10 mg/mL, about 0.1 mg/mL to about 0.5 mg/mL, about 0.1 mg/mL to about 1 mg/mL, about 0.1 mg/mL to about 1.25 mg/mL, about 0.1 mg/mL to about 1.5 mg/mL, about 0.1 mg/mL to about 1.75 mg/mL, about 0.1 mg/mL to about 2 mg/mL, about 0.1 mg/mL to about 5 mg/mL, about 0.1 mg/mL to about 10 mg/mL, about 0.5 mg/mL to about 1 mg/mL, about 0.5 mg/mL to about 1.25 mg/mL, about 0.5 mg/mL to about 1.5 mg/mL, about 0.5 mg/mL to about 1.75 mg/mL, about 0.5 mg/mL to about 2 mg/mL, about 0.5 mg/mL to about 5 mg/mL, about 0.5 mg/mL to about 10 mg/mL, about 1 mg/mL to about 1.25 mg/mL, about 1 mg/mL to about 1.5 mg/mL, about 1 mg/mL to about 1.75 mg/mL, about 1 mg/mL to about 2 mg/mL, about 1 mg/mL to about 5 mg/mL, about 1 mg/mL to about 10 mg/mL, about 1.25 mg/mL to about 1.5 mg/mL, about 1.25 mg/mL to about 1.75 mg/mL, about 1.25 mg/mL to about 2 mg/mL, about 1.25 mg/mL to about 5 mg/mL, about 1.25 mg/mL to about 10 mg/mL, about 1.5 mg/mL to about 1.75 mg/mL, about 1.5 mg/mL to about 2 mg/mL, about 1.5 mg/mL to about 5 mg/mL, about 1.5 mg/mL to about 10 mg/mL, about 1.75 mg/mL to about 2 mg/mL, about 1.75 mg/mL to about 5 mg/mL, about 1.75 mg/mL to about 10 mg/mL, about 2 mg/mL to about 5 mg/mL, about 2 mg/mL to about 10 mg/mL, or about 5 mg/mL to about 10 mg/mL. In some embodiments, the anionic polymer material is present in an amount of about 0.01 mg/mL, about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, about 5 mg/mL, or about 10 mg/mL. In some embodiments, the anionic polymer material is present in an amount of at least about 0.01 mg/mL, about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, or about 5 mg/mL. In some embodiments, the anionic polymer material is present in an amount of at most about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, about 5 mg/mL, or about 10 mg/mL.

In some embodiments, the additional components comprise purified water. In some embodiments, purified water is present in an amount of about 50% to 80% (w/w). In some embodiments, purified water is present in an amount of about 50% to about 55%, about 50% to about 60%, about 50% to about 65%, about 50% to about 70%, about 50% to about 75%, about 50% to about 80%, about 55% to about 60%, about 55% to about 65%, about 55% to about 70%, about 55% to about 75%, about 55% to about 80%, about 60% to about 65%, about 60% to about 70%, about 60% to about 75%, about 60% to about 80%, about 65% to about 70%, about 65% to about 75%, about 65% to about 80%, about 70% to about 75%, about 70% to about 80%, or about 75% to about 80%. In some embodiments, purified water is present in an amount of about 50%, about 55%, about 60%, about 65%, about 70%, about 75%, or about 80%. In some embodiments, purified water is present in an amount of at least about 50%, about 55%, about 60%, about 65%, about 70%, or about 75%. In some embodiments, purified water is present in an amount of at most about 55%, about 60%, about 65%, about 70%, about 75%, or about 80%.

Exemplary Compositions for Delivery of Peptide Antagonists

Provided below are exemplary compositions for the delivery of peptide antagonists. In some embodiments, the delivery of the peptide antagonist comprises a method of preparing a lipid vesicle composition, the method comprising: a) preparing an oil-in-water emulsion comprising the peptide antagonist of a melanocortin 1 receptor, by mixing oil components of the oil-in-water emulsion with aqueous components of the oil-in-water emulsion; b) solubilizing vesicle forming lipids in an acceptable solvent other than water; c) adding the oil-in-water emulsion to the solubilized vesicle forming lipids; and d) mixing the oil-in-water emulsion and the solubilized vesicle forming lipids under mixing conditions effective to form the lipid vesicles comprising a lipid bilayer comprising vesicle forming lipids, and an oil-in-water emulsion entrapped in the lipid vesicles. In some cases, the aqueous components comprise the peptide antagonist of a melanocortin 1 receptor. In some cases, the oil components and/or the aqueous components of the oil-in-water emulsion comprises the one or more surfactants. The embodiments below may additional comprise any of the other ingredients or components provided herein.

Peptide Composition 1: In one aspect, provided herein, is a lipid vesicle composition comprising:
(a) lipid vesicles each comprising a lipid bilayer comprising vesicle forming lipids, wherein the vesicle forming lipids are present in an amount of from about 5% to about 20%;
(b) an oil-in-water emulsion entrapped in the lipid vesicles, stabilized by one or more surfactants;
(c) a peptide antagonist of a melanocortin 1 receptor in an amount of from about 0.1 mg/mL to about 50 mg/mL entrapped in the lipid bilayer and/or the oil-in-water emulsion,
wherein the composition further comprises:
a fatty amide derived propylene glycol-diammonium phosphate ester in an amount of from about 1% to about 10%; and
a non-ionic surfactant in an amount of from about 0.1% to about 3%.

In some embodiments, the oil component is present in an amount of from about 2.5% to about 20%.

In some embodiments, the lipid vesicle composition comprises the peptide antagonist in an amount of about 0.1 mg/mL to about 0.5 mg/mL, about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 10 mg/mL, about 0.1 mg/mL to about 20 mg/mL, about 0.1 mg/mL to about 50 mg/mL. In some embodiments the lipid vesicle composition comprises the peptides antagonist in an amount of about 0.1 mg/mL, about 0.5 mg/mL, about 1 mg/mL, about 2 mg/mL, about 3 mg/mL, about 4 mg/mL, about 5 mg/mL, about 10 mg/mL, about 20 mg/mL, or about 50 mg/mL. In some embodiments, the lipid vesicle composition comprises the peptides antagonist in an amount of about 1 mg/mL, about 2 mg/mL, about 3 mg/mL, about 4 mg/mL, or about 5 mg/mL.

In some embodiments, the composition further comprises a fatty acylated amino acid in an amount of from about 0.5% to about 3%. In some embodiments, the fatty acylated amino acid is monoloauryl lysine.

In some embodiments, the lipid vesicle composition further comprises viscosity enhancing agents in an amount of from about 0.5% to about 5%. In some embodiments, the viscosity enhancing agents comprise one or more of a fatty alcohol, a wax, a fatty ester of glycerol, or any combination thereof.

In some embodiments, the non-ionic surfactant comprises a PEG ether of a fatty alcohol.

In some embodiments, the lipid vesicle composition further comprises an anionic polymer material in an amount of from about 0.01 mg/mL to about 10 mg/mL entrapped in the lipid bilayer, the oil-in-water emulsion, or a combination thereof. In some embodiments, the lipid vesicle composition comprises the anionic polymer material in an amount of about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 1.25 mg/mL, about 0.01 mg/mL to about 1.5 mg/mL, about 0.01 mg/mL to about 1.75 mg/mL, about 0.01 mg/mL to about 2 mg/mL, about 0.01 mg/mL to about 5 mg/mL, about 0.01 mg/mL to about 10 mg/mL, about 0.1 mg/mL to about 0.5 mg/mL, about 0.1 mg/mL to about 1 mg/mL, about 0.1 mg/mL to about 1.25 mg/mL, about 0.1 mg/mL to about 1.5 mg/mL, about 0.1 mg/mL to about 1.75 mg/mL, about 0.1 mg/mL to about 2 mg/mL, about 0.1 mg/mL to about 5 mg/mL, about 0.1 mg/mL to about 10 mg/mL, about 0.5 mg/mL to about 1 mg/mL, about 1 mg/mL to about 1.5 mg/mL, about 1 mg/mL to about 1.75 mg/mL, about 1 mg/mL to about 2 mg/mL, about 1 mg/mL to about 5 mg/mL, about 1 mg/mL to about 10 mg/mL. In some embodiments, the lipid vesicle composition comprises the anionic polymer material in an amount of about 0.01 mg/mL, about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, about 5 mg/mL, or about 10 mg/mL.

Peptide Composition 2: In one aspect, provided herein, is a lipid vesicle composition comprising:
  (a) lipid vesicles each comprising a lipid bilayer comprising vesicle forming lipids, wherein the vesicle forming lipids are present in an amount of from about 2% to about 20%;
  (b) an oil-in-water emulsion entrapped in the lipid vesicles, and stabilized by one or more surfactants;
  (c) a peptide antagonist of a melanocortin 1 receptor in an amount of from about 0.1 mg/mL to about 50 mg/mL entrapped in the lipid bilayer and/or the oil-in-water emulsion,
  wherein the composition further comprises:
  a PEG fatty acid ester in an amount of from about 0.1% to about 2%;
  a polysorbate in an amount of from about 0.5% to about 3%; and
  a sorbate ester in an amount of from about 0.1% to about 2%.

In some embodiments, the oil component is present in an amount of from about 2.5% to about 20%.

In some embodiments, the lipid vesicle composition comprises the peptide antagonist in an amount of about 0.1 mg/mL to about 0.5 mg/mL, about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 10 mg/mL, about 0.1 mg/mL to about 20 mg/mL, about 0.1 mg/mL to about 50 mg/mL. In some embodiments the lipid vesicle composition comprises the peptides antagonist in an amount of about 0.1 mg/mL, about 0.5 mg/mL, about 1 mg/mL, about 2 mg/mL, about 3 mg/mL, about 4 mg/mL, about 5 mg/mL, about 10 mg/mL, about 20 mg/mL, or about 50 mg/mL. In some embodiments, the lipid vesicle composition comprises the peptides antagonist in an amount of about 1 mg/mL, about 2 mg/mL, about 3 mg/mL, about 4 mg/mL, or about 5 mg/mL.

In some embodiments, the lipid vesicle composition further comprises viscosity enhancing agents in an amount of from about 0.5% to about 5%. In some embodiments, the viscosity enhancing agents comprise one or more of a fatty alcohol, a wax, a fatty ester of glycerol, or any combination thereof.

In some embodiments, the PEG fatty acid ester comprises PEG4-dilaurate. In some embodiments, the polysorbate is polysorbate 80. In some embodiments, the sorbate ester is sorbitan palmitate.

In some embodiments, the lipid vesicle composition further comprises an anionic polymer material in an amount of from about 0.01 mg/mL to about 10 mg/mL entrapped in the lipid bilayer, the oil-in-water emulsion, or a combination thereof. In some embodiments, the lipid vesicle composition comprises the anionic polymer material in an amount of about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 1.25 mg/mL, about 0.01 mg/mL to about 1.5 mg/mL, about 0.01 mg/mL to about 1.75 mg/mL, about 0.01 mg/mL to about 2 mg/mL, about 0.01 mg/mL to about 5 mg/mL, about 0.01 mg/mL to about 10 mg/mL, about 0.1 mg/mL to about 0.5 mg/mL, about 0.1 mg/mL to about 1 mg/mL, about 0.1 mg/mL to about 1.25 mg/mL, about 0.1 mg/mL to about 1.5 mg/mL, about 0.1 mg/mL to about 1.75 mg/mL, about 0.1 mg/mL to about 2 mg/mL, about 0.1 mg/mL to about 5 mg/mL, about 0.1 mg/mL to about 10 mg/mL, about 0.5 mg/mL to about 1 mg/mL, about 1 mg/mL to about 1.5 mg/mL, about 1 mg/mL to about 1.75 mg/mL, about 1 mg/mL to about 2 mg/mL, about 1 mg/mL to about 5 mg/mL, about 1 mg/mL to about 10 mg/mL. In some embodiments, the lipid vesicle composition comprises the anionic polymer material in an amount of about 0.01 mg/mL, about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, about 5 mg/mL, or about 10 mg/mL.

Peptide Composition 3: In one aspect, provided herein, is a lipid vesicle composition comprising:
  (a) lipid vesicles each comprising a lipid bilayer comprising vesicle forming lipids, wherein the vesicle forming lipids are present in an amount of from about 5% to about 20%;
  (b) an oil-in-water emulsion entrapped in the lipid vesicles, and stabilized by one or more surfactants;
  (c) a peptide antagonist of a melanocortin 1 receptor in an amount of from about 0.1 mg/mL to about 50 mg/mL entrapped in the lipid bilayer and/or the oil-in-water emulsion,
  wherein the composition further comprises; and
  a fatty amide derived propylene glycol-diammonium phosphate ester in an amount of from about 1% to about 10%;
  a PEG ether of a fatty alcohol in an amount of from about 0.1% to about 3%;

a polysorbate in an amount of from about 0.5% to about 3%; and a sorbate ester in an amount of from about 0.1% to about 2%.

In some embodiments, the oil component is present in an amount of from about 2.5% to about 20%.

In some embodiments, the lipid vesicle composition comprises the peptide antagonist in an amount of about 0.1 mg/mL to about 0.5 mg/mL, about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 10 mg/mL, about 0.1 mg/mL to about 20 mg/mL, about 0.1 mg/mL to about 50 mg/mL. In some embodiments the lipid vesicle composition comprises the peptides antagonist in an amount of about 0.1 mg/mL, about 0.5 mg/mL, about 1 mg/mL, about 2 mg/mL, about 3 mg/mL, about 4 mg/mL, about 5 mg/mL, about 10 mg/mL, about 20 mg/mL, or about 50 mg/mL. In some embodiments, the lipid vesicle composition comprises the peptides antagonist in an amount of about 1 mg/mL, about 2 mg/mL, about 3 mg/mL, about 4 mg/mL, or about 5 mg/mL.

In some embodiments, the lipid vesicle composition further comprises viscosity enhancing agents in an amount of from about 0.5% to about 5%. In some embodiments, the viscosity enhancing agents comprise one or more of a fatty alcohol, a wax, a fatty ester of glycerol, or any combination thereof.

In some embodiments, the polysorbate is polysorbate 80. In some embodiments, the sorbate ester is sorbitan palmitate. In some embodiments, the PEG ether of the fatty alcohol is diethylene glycol monooleyl ether.

In some embodiments, the lipid vesicle composition further comprises an anionic polymer material in an amount of from about 0.01 mg/mL to about 10 mg/mL entrapped in the lipid bilayer, the oil-in-water emulsion, or a combination thereof. In some embodiments, the lipid vesicle composition comprises the anionic polymer material in an amount of about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 1.25 mg/mL, about 0.01 mg/mL to about 1.5 mg/mL, about 0.01 mg/mL to about 1.75 mg/mL, about 0.01 mg/mL to about 2 mg/mL, about 0.01 mg/mL to about 5 mg/mL, about 0.01 mg/mL to about 10 mg/mL, about 0.1 mg/mL to about 0.5 mg/mL, about 0.1 mg/mL to about 1 mg/mL, about 0.1 mg/mL to about 1.25 mg/mL, about 0.1 mg/mL to about 1.5 mg/mL, about 0.1 mg/mL to about 1.75 mg/mL, about 0.1 mg/mL to about 2 mg/mL, about 0.1 mg/mL to about 5 mg/mL, about 0.1 mg/mL to about 10 mg/mL, about 0.5 mg/mL to about 1 mg/mL, about 1 mg/mL to about 1.5 mg/mL, about 1 mg/mL to about 1.75 mg/mL, about 1 mg/mL to about 2 mg/mL, about 1 mg/mL to about 5 mg/mL, about 1 mg/mL to about 10 mg/mL. In some embodiments, the lipid vesicle composition comprises the anionic polymer material in an amount of about 0.01 mg/mL, about 0.05 mg/mL, about 0.1 mg/mL, about 0.5 mg/mL, about 1 mg/mL, about 1.25 mg/mL, about 1.5 mg/mL, about 1.75 mg/mL, about 2 mg/mL, about 5 mg/mL, or about 10 mg/mL.

Methods of Use of Lipid Vesicle Compositions Provided Herein

The lipid vesicle compositions provided herein are contemplated for cosmetic uses in a subject, for indications including but not limited to for preventing, reducing, or both, the appearance of skin discoloration due to pigmentation.

In certain embodiments, including pharmaceutical embodiments, the lipid vesicle compositions provided herein are contemplated for pharmaceutical use in a subject, for indications including but not limited to: the skin discoloration, e.g., pigmentation or hyperpigmentation, comprises melanin hyperpigmentation, chloasma, melasma, age spots, freckles, or a combination thereof. In some embodiments, the skin discoloration results from a disorder, e.g., an adrenal disorder. In some embodiments, the MC1R peptide antagonists of the disclosure are used to treat skin discoloration caused by Addison's disease.

In some embodiments, the subject is a mammal. In specific embodiments, the mammal is a human. In some embodiments, the human subject is a pediatric or adult subject, of any age.

Methods for Using Cosmetic or Pharmaceutical Compositions

In certain embodiments, including pharmaceutical embodiments, the present disclosure also relates to methods for using cosmetic or pharmaceutical compositions comprising a peptide antagonist. In some embodiments, the disclosure comprises a method of preventing or reducing skin discoloration in a subject, the method comprising administering a lipid vesicle composition to said subject, wherein the lipid vesicle composition comprises: (a) lipid vesicles each comprising a lipid bilayer comprising vesicle forming lipids, (b) an oil-in-water emulsion entrapped in the lipid vesicles, and stabilized by one or more surfactants; (c) a peptide antagonist of a melanocortin 1 receptor entrapped in the lipid bilayer and/or the oil-in-water emulsion. In some embodiments, the skin discoloration is melanin hyperpigmentation, chloasma, melasma, age spots, freckles, or a combination thereof. In some embodiments, the disclosure relates to methods for using the cosmetic or pharmaceutical composition to prevent or reduce skin discoloration, comprising applying an effective amount of the cosmetic or pharmaceutical composition to the skin of the subject. In some embodiments, the skin discoloration comprises melanin hyperpigmentation, post-inflammatory hyperpigmentation, chloasma, melasma, age spots (e.g., liver spots, senile lentigines, solar lentigines, sunspots), freckles, or a combination thereof. In some embodiments, the skin discoloration results from a disorder, e.g., an adrenal disorder. In some embodiments, the MC1R peptide antagonists of the disclosure are used to treat skin discoloration caused by Addison's disease. In some embodiments, the cosmetic or pharmaceutical composition is used to diminish or visible remove the appearance of dark spots on the face or body of the subject. In some embodiments, the cosmetic or pharmaceutical composition diminish color in dark spots. In some embodiments, the cosmetic or pharmaceutical composition provides a more even tone across the face of the subject.

In some embodiments, the lipid vesicle composition is topically applied to a subject. Topical application as referred to herein can refer to application onto one or more surface, e.g., keratinous tissue. In some embodiments, the topical composition is administered to the skin of a subject. In some embodiments, the skin is the facial skin of the subject. Topical application may relate to direct application to the desired area. A topical cosmetic or pharmaceutical composition or preparation can be applied by, e.g., pouring, dropping, or spraying, when present as a liquid or aerosol composition; smoothing, rubbing, spreading, and the like, when in ointment, lotion, cream, gel, or a like composition; dusting, when a powder; or by any other appropriate means.

In some embodiments, the lipid vesicle composition is formulated in a form suitable for topical application. In some embodiments, the lipid vesicle composition is formulated as a cream, a lotion, a suspension, or an emulsion. In some embodiments, the lipid vesicle composition is formulated as a cream. In some embodiments, the lipid vesicle composition is formulated as a lotion. In some embodiments, the lipid vesicle composition is formulated as a suspension.

In certain embodiments, including pharmaceutical embodiments, the subject uses or is treated with a topical application comprising an effective amount of the lipid vesicle composition one time or more during a course of usage or treatment, e.g., 1-3 times per day, 1-21 times per week, 1 time per day, 2 times per day, or 3 times per day. In some embodiments, a subject uses or is treated with an effective amount of the lipid vesicle composition about 1 time per week to about 12 times per week. In some embodiments, a subject uses or is treated with an effective amount of the lipid vesicle composition at least about 1 time per week. In some embodiments, a subject uses or is treated with an effective amount of the lipid vesicle composition at most about 12 times per week. In some embodiments, a subject uses or is treated with an effective amount of the lipid vesicle composition about 1 time per week to about 2 times per week, about 1 time per week to about 3 times per week, about 1 time per week to about 4 times per week, about 1 time per week to about 5 times per week, about 1 time per week to about 6 times per week, about 1 time per week to about 7 times per week, about 1 time per week to about 8 times per week, about 1 time per week to about 9 times per week, about 1 time per week to about 10 times per week, about 1 time per week to about 11 times per week, about 1 time per week to about 12 times per week, about 2 times per week to about 3 times per week, about 2 times per week to about 4 times per week, about 2 times per week to about 5 times per week, about 2 times per week to about 6 times per week, about 2 times per week to about 7 times per week, about 2 times per week to about 8 times per week, about 2 times per week to about 9 times per week, about 2 times per week to about 10 times per week, about 2 times per week to about 11 times per week, about 2 times per week to about 12 times per week, about 3 times per week to about 4 times per week, about 3 times per week to about 5 times per week, about 3 times per week to about 6 times per week, about 3 times per week to about 7 times per week, about 3 times per week to about 8 times per week, about 3 times per week to about 9 times per week, about 3 times per week to about 10 times per week, about 3 times per week to about 11 times per week, about 3 times per week to about 12 times per week, about 4 times per week to about 5 times per week, about 4 times per week to about 6 times per week, about 4 times per week to about 7 times per week, about 4 times per week to about 8 times per week, about 4 times per week to about 9 times per week, about 4 times per week to about 10 times per week, about 4 times per week to about 11 times per week, about 4 times per week to about 12 times per week, about 5 times per week to about 6 times per week, about 5 times per week to about 7 times per week, about 5 times per week to about 8 times per week, about 5 times per week to about 9 times per week, about 5 times per week to about 10 times per week, about 5 times per week to about 11 times per week, about 5 times per week to about 12 times per week, about 6 times per week to about 7 times per week, about 6 times per week to about 8 times per week, about 6 times per week to about 9 times per week, about 6 times per week to about 10 times per week, about 6 times per week to about 11 times per week, about 6 times per week to about 12 times per week, about 7 times per week to about 8 times per week, about 7 times per week to about 9 times per week, about 7 times per week to about 10 times per week, about 7 times per week to about 11 times per week, about 7 times per week to about 12 times per week, about 8 times per week to about 9 times per week, about 8 times per week to about 10 times per week, about 8 times per week to about 11 times per week, about 8 times per week to about 12 times per week, about 9 times per week to about 10 times per week, about 9 times per week to about 11 times per week, about 9 times per week to about 12 times per week, about 10 times per week to about 11 times per week, about 10 times per week to about 12 times per week, or about 11 times per week to about 12 times per week. In some embodiments, a subject uses or is treated with an effective amount of the lipid vesicle composition about 1 time per week, about 2 times per week, about 3 times per week, about 4 times per week, about 5 times per week, about 6 times per week, about 7 times per week, about 8 times per week, about 9 times per week, about 10 times per week, about 11 times per week, about 12 times per week, about 13 times per week, or about 14 times per week.

In some embodiments, one or more layers of a lipid vesicle composition of the disclosure is applied to the skin of the subject at a given time. In some embodiments, a subsequent layer may be applied after a previous layer of the lipid vesicle composition is fully absorbed into the skin of the subject. In some embodiments, the lipid vesicle composition may take a couple of seconds (e.g., one second, two seconds, three second, five seconds, ten seconds, fifteen seconds, thirty seconds, etc.) to fully absorb into the skin of the subject. In some embodiments, one, two, three, four, five, six, or seven layers of the lipid vesicle composition is applied to the skin of the subject at a given time. In some embodiments, the lipid vesicle composition is applied to the skin of the subject one or more times a day (e.g., 1-3 times per day, 1 time per day, 2 times per day, 3 times per day, etc.). In some embodiments, the lipid vesicle composition is applied to the skin of the subject one or more times a week (e.g., 1-21 times per week, 1-14 times per week, 1-7 times per week, etc.). In some embodiments, the lipid vesicle composition is applied to the skin of the subject daily. In some embodiments, one or more layers of the lipid vesicle composition is applied to the skin of the subject once a day for one or more days. In some embodiments, two or more layers of the lipid vesicle composition is applied to the skin of the subject once a day for one or more days. In some embodiments, three or more layers of the lipid vesicle composition is applied to the skin of the subject once a day for one or more days. In some embodiments, one or more layers of the lipid vesicle composition is applied to the skin of the subject twice a day for one or more days. In some embodiments, two or more layers of the lipid vesicle composition is applied to the skin of the subject twice a day for one or more days. In some embodiments, three or more layers of the lipid vesicle composition is applied to the skin of the subject twice a day for one or more days. In some embodiments, the lipid vesicle composition is applied to the skin of the subject for at least one day, two days, three days, four days, five days, six days, one week, two weeks, three weeks, one month, two months, three months, six months, one year. In some embodiments, the lipid vesicle composition is applied to the skin of the subject for more than one day, two days, three days, four days, five days, six days, one week, two weeks, three weeks, one month, two months, three months, six months, nine months, or one year. In some embodiments, one or more layers of the lipid vesicle composition is applied to the skin of the subject twice a day for several days, and thereafter is applied three times a day. In some embodiments, five layers of the lipid vesicle composition is applied to the skin of the subject twice a day for five days (e.g., morning and night), and thereafter one to three layers of the lipid vesicle composition is applied to the skin of the subject three times a day (e.g., morning, noon and night).

In certain embodiments, including pharmaceutical embodiments, a lipid vesicle composition of the disclosure is administered to a subject, for indications including but not limited to: prevention or temporary improvement of the appearance of skin discoloration e.g., dark spots, melanin hyperpigmentation, post-inflammatory hyperpigmentation, chloasma, melasma, age spots (e.g., liver spots, senile lentigines, solar lentigines, sunspots), freckles, or a combination thereof.

In certain embodiments, including pharmaceutical embodiments, a lipid vesicle composition of the disclosure is administered to a subject, for indications including but not limited to: improvement of the appearance of skin discoloration. In some embodiments, a lipid vesicle composition of the disclosure is used with other products, including, but not limited to sunscreen, moisturizers, face creams (e.g., BB cream, CC cream, night cream, etc.), mists, foundations, concealers, highlighters, primers, etc.

In some embodiments, a topical cosmetic composition of the disclosure is self-applied by a subject. In some embodiments, a topical cosmetic composition of the disclosure is not self-applied by a subject. In some embodiments, a topical cosmetic composition of the disclosure is administered by a subject. In certain embodiments, including pharmaceutical embodiments, a cosmetic or pharmaceutical composition of the disclosure is applied or administered by a medical professional, e.g., in a medical office setting.

Methods of Making Lipid Vesicle Compositions Provided Herein

Also provided herein are method of making lipid vesicle compositions. In some embodiments, compositions of the disclosure as described above are prepared by mixing oil components of the oil-in-water emulsion with aqueous components of the oil-in-water emulsion wherein either the oil components or aqueous components of the oil-in-water emulsion comprises one or more surfactants for emulsification of the oil component with the aqueous component of the oil-in-water emulsion. In an embodiment, the surfactant is mixed with the aqueous component and added to the oil for formation of an emulsion. The oil-in-water emulsion is then mixed with the solubilized vesicle-forming lipid and, if added, other lipid components under mixing conditions effective to form the lipid vesicles (e.g., multisomes).

In some embodiments, one or more penetration enhancing agents and the one or more compounds are added to oil component of the oil-in-water emulsion, to the aqueous component of the oil-in-water emulsion or both. Alternatively, or in addition to, the one or more penetration enhancing agents and/or the one or more compounds can be added to the lipid component.

In one aspect, provided herein, is a method of preparing a lipid vesicle composition provided herein, comprising a) preparing an oil-in-water emulsion comprising an active ingredient, by mixing oil components of the oil-in-water emulsion with aqueous components of the oil-in-water emulsion; b) solubilizing vesicle forming lipids in an acceptable solvent other than water; c) adding the oil-in-water emulsion to the solubilized vesicle forming lipids; and d) mixing the oil-in-water emulsion and the solubilized vesicle forming lipids under mixing conditions effective to form the lipid vesicles comprising a lipid bilayer comprising vesicle forming lipids, and an oil-in-water emulsion entrapped in the lipid vesicles.

In one aspect, provided herein, is a method of preparing a lipid vesicle composition provided herein, comprising: a) preparing an oil-in-water emulsion comprising the peptide antagonist of a melanocortin 1 receptor, by mixing oil components of the oil-in-water emulsion with aqueous components of the oil-in-water emulsion, wherein the oil components and/or the aqueous components of the oil-in-water emulsion comprises the one or more surfactants; b) solubilizing vesicle forming lipids in an acceptable solvent other than water; c) adding the oil-in-water emulsion to the solubilized vesicle forming lipids; and d) mixing the oil-in-water emulsion and the solubilized vesicle forming lipids under mixing conditions effective to form the lipid vesicles comprising a lipid bilayer comprising vesicle forming lipids, and an oil-in-water emulsion entrapped in the lipid vesicles.

In some embodiments, the active ingredient is one or more peptides provided herein. In some embodiments, the one or more peptides comprises an amino acid sequence at least about 50%, at least about 60%, at least about 70%, at least about 80%, or at least about 90% sequence homology to the amino acid sequence of any one of SEQ ID NO: 1-90. In some embodiments, the one or more peptides comprises an amino acid sequence identical to the amino acids of any one of SEQ ID NO: 1-90. In some embodiments, the one or more peptides comprises an amino acid sequence at least about 50%, at least about 60%, at least about 70%, at least about 80%, or at least about 90% sequence homology to the amino acid sequence of any one of SEQ ID NO: 4-19 or 44-65. In some embodiments, the one or more peptides comprises an amino acid sequence identical to the amino acids of any one of SEQ ID NO: 4-19 or 44-65. In some embodiments, the active ingredient is an anionic polymer material provided herein. In some embodiments, the lipid vesicle may comprise of one or more active ingredients. In some embodiments, the one or more active ingredients comprise one or more peptides. In some embodiments, the one or more active ingredients comprise an anionic polymer material. In some embodiments, the one or more active ingredients comprise one or more peptides and an anionic polymer material. In some embodiments, the anionic polymer material is hyaluronic acid.

In some embodiments, the method further comprises adding one or more of the additional components provided herein (e.g., penetration enhancing agents, viscosity enhancing agents, etc.).

In some embodiments, mixing oil components of the oil-in-water emulsion with aqueous components of the oil-in-water emulsion vesicles of step a) and/or the mixing conditions of step e) comprises using agitation such as homogenization or emulsification, or micro-emulsion techniques which do not involve agitation. In an embodiment, the mixing comprises high pressure homogenizing. The high pressure homogenizing provides relatively precise control over the composition of the lipid vesicles. High pressure homogenizing is suitable for small molecules and peptides or proteins that are resistant to shearing. In an embodiment, the composition that is formed is any one of the lipid vesicle compositions described herein.

In some embodiments, other lipid components are added at any one of the steps.

EXAMPLES

Example 1. Binding of Melanocortin 1 Receptor Group A Peptide Antagonists to MC1R Using Radioligand Competition Assay The binding of Group A MC1R peptide antagonists of the disclosure was evaluated in a competition assay (MC1 Human Melanocortin GPCR Binding (Agonist Radioligand) Assay, Item 251100, Eurofins Discovery). Peptides were synthesized by AnaSpec (Fremont, CA). Human recombinant melanocortin MCI receptors were expressed in CHO-K1 cells in modified HEPES-KOH buffer pH 7.0. A 3 µgs aliquot was incubated with 0.04 nM [$^{125}$I]NDP-α-MSH for 120 minutes at 37° C. Non-specific binding was estimated in the presence of 1 µM NDP-α-MSH. Receptors were filtered and washed, and the filters counted to determine [$^{125}$I]NDP-α-MSH specifically bound. Peptide antagonists of the disclosure having amino acid sequences as set forth in SEQ ID NOS: 11, 16, 25, 27, 32, 35, and 40 (each having a C-terminal —NH2) were screened at five concentrations, as well as a positive control, SEQ ID NO: 1 (Melanostatine-5). Inhibition curves were obtained by determining the reduction of bound α-MSH in the presence of an amount of, and/or by increasing amounts of, each peptide antagonist. Non-specific binding of peptide was estimated separately in the presence of a vast excess (1 mM) of unlabeled α-MSH, which occupies all the available receptor binding sites.

Based on the competitive binding curve, the IC$_{50}$ values were determined (Eurofins or AAT Bioquest IC$_{50}$ calculator). As shown in Table 4, the IC$_{50}$ value for the Melanostatine-5 control (SEQ ID NO: 1) was 120 nM. The test peptides had IC$_{50}$ values ranging from below 74 nm (markedly below Melanostatine-5), to greater than 1 uM.

TABLE 4

Binding of Peptide Antagonists to MC1R

| Test Peptide IC$_{50}$ values (nm) | Control IC$_{50}$ value (nm) |
|---|---|
| <75 | 120 |
| 75-150 | |
| 150-500 | |
| 500-1000 | |
| >1000 | |

Example 2. Binding of Melanocortin 1 Receptor Group B Peptide Antagonists to MC1R Using Radioligand Competition Assay The binding of Group B peptide antagonists of the disclosure to MC1R is evaluated in a competition assay (MC1 Human Melanocortin GPCR Binding (Agonist Radioligand) Assay, Item 251100, Eurofins Discovery). Peptides are synthesized by AnaSpec (Fremont, CA). Human recombinant melanocortin MCI receptors are expressed in CHO-K1 cells in modified HEPES-KOH buffer pH 7.0. A 3 µg aliquot is incubated with 0.04 nM [$^{125}$I]NDP-α-MSH for 120 minutes at 37° C. Non-specific binding is estimated in the presence of 1 µM NDP-α-MSH. Receptors are filtered and washed, and the filters counted to determine [$^{125}$I]NDP-α-MSH specifically bound. Group B peptide antagonists of the disclosure having amino acid sequences as set forth in Table 2 are screened at 10 µM, as well as one or more positive control selected from SEQ ID NO: 1 (Melanostatine-5), the 132-amino acid natural MC1R antagonist Agouti Signaling Protein (ASIP) (SEQ ID NO: 91), mature ASIP (SEQ ID NO: 92), a fragment of ASIP, e.g., ASIP 107-132 (SEQ ID NO: 2), or a variant of ASIP or fragment thereof, e.g., ASIP-YY (SEQ ID NO: 93), ASIP-YY 107-132 subdomain (SEQ ID NO: 3), or ASIP-YY 93-132 subdomain (SEQ ID NO: 94). Inhibition curves are obtained by determining the reduction of bound α-MSH in the presence of an amount of, and/or by increasing amounts of, each peptide antagonist. Non-specific binding of peptide is stimulated separately in the presence of a vast excess (1 mM) of unlabeled α-MSH, which occupies all the available receptor binding sites.

Based on the percent maximum inhibition relative to the agonist, the IC$_{50}$ values are determined (Eurofins or AAT Bioquest IC$_{50}$ calculator). The Group B peptide antagonist IC$_{50}$ values are compared with the control values.

Example 3. Evaluation of Skin Lightening by MC1R Peptide Antagonists In Vitro Formulations comprising MC1R peptide antagonists of the disclosure are tested in vitro for skin lightening effects using the MelanoDerm tissue model (MatTek, Inc.). Using this model, formulations comprising MC1R peptide antagonists of the disclosure, e.g., any peptide having an amino as set forth in Table 1 and Table 2, are evaluated in comparison to controls (e.g., no treatment or treatment with agonist α-MSH) and positive controls for lightening (e.g., formulations comprising a peptide having a sequence set forth in any of SEQ ID NOS: 1-3, 91, 92, 93 and 94, or a small molecule tyrosinase inhibitor such as Kojic Acid). Pigmentation is evaluated over the course of 2-3 weeks using a tristimulus chromometer to measure brightness (L*) in MelanoDerm tissue produced with normal human melanocytes from Black, Asian, or Caucasian donors. In parallel to measurements taken with the chromameter, total melanin content of tissues is also quantified.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

TABLE 5

Table of Sequences Listed

| Protein | Sequence | SEQ ID NO: |
|---|---|---|
| Melanostatine-5/ Nonapeptide-1 | Met-Pro-D-Phe-Arg-D-Trp-Phe-Lys-Pro-Val | 1 |

TABLE 5-continued

Table of Sequences Listed

| Protein | Sequence | SEQ ID NO: |
|---|---|---|
| ASIP 177-132 subdomain (Agouti Signaling Protein, residues 107-132) | Cys-Cys-Asp-Pro-Cys-Ala-Ser-Cys-Gln-Cys-Arg-Phe-Phe-Arg-Ser-Ala-Cys-Ser-Cys-Arg-Val-Leu-Ser Leu Asn Cys | 2 |
| ASIP-YY 107-132 sub domain (ASIP-YY residues 28-53; ASIP 107-132, Q115Y, S124Y) | Cys-Cys-Asp-Pro-Cys-Ala-Ser-Cys-Tyr-Cys-Arg-Phe-Phe-Arg-Ser-Ala-Cys-Tyr-Cys-Arg-Val-Leu-Ser Leu Asn Cys | 3 |
| Group A Peptide Antagonist | See Table 1 | 4-43 |
| Group B Peptide Antagonist | See Table 2 | 44-90 |
| Agouti Signaling Protein (ASIP) UniProtKB - P42127 Italics: 22 amino acid signal sequence Underline: mature 110 amino acid ASIP sequence | Met-Asp-Val-Thr-Arg-Leu-Leu-Leu-Ala-Thr-Leu-Leu-Val-Phe-Leu-Cys-Phe-Phe-Thr-Ala-Asn-Ser-His-Leu-Pro-Pro-Glu-Glu-Lys-Leu-Arg-Asp-Asp-Arg-Ser-Leu-Arg-Ser-Asn-Ser-Ser-Val-Asn-Leu-Leu-Asp-Val-Pro-Ser-Val-Ser-Ile-Val-Ala-Leu-Asn-Lys-Lys-Ser-Lys-Gln-Ile-Gly-Arg-Lys-Ala-Ala-Glu-Lys-Lys-Arg-Ser-Ser-Lys-Lys-Glu-Ala-Ser-Met-Lys-Lys-Val-Val-Arg-Pro-Arg-Thr-Pro-Leu-Ser-Ala-Pro-Cys-Val-Ala-Thr-Arg-Asn-Ser-Cys-Lys-Pro-Pro-Ala-Pro-Ala-Cys-Cys-Asp-Pro-Cys-Ala-Ser-Cys-Gln-Cys-Arg-Phe-Phe-Arg-Ser-Ala-Cys-Ser-Cys-Arg-Val-Leu-Ser-Leu-Asn-Cys | 91 |
| Mature Agouti Signaling Protein (ASIP 23-132) | His-Leu-Pro-Pro-Glu-Glu-Lys-Leu-Arg-Asp-Asp-Arg-Ser-Leu-Arg-Ser-Asn-Ser-Ser-Val-Asn-Leu-Leu-Asp-Val-Pro-Ser-Val-Ser-Ile-Val-Ala-Leu-Asn-Lys-Lys-Ser-Lys-Gln-Ile-Gly-Arg-Lys-Ala-Ala-Glu-Lys-Lys-Arg-Ser-Ser-Lys-Lys-Glu-Ala-Ser-Met-Lys-Lys-Val-Val-Arg-Pro-Arg-Thr-Pro-Leu-Ser-Ala-Pro-Cys-Val-Ala-Thr-Arg-Asn-Ser-Cys-Lys-Pro-Pro-Ala-Pro-Ala-Cys-Cys-Asp-Pro-Cys-Ala-Ser-Cys-Gln-Cys-Arg-Phe-Phe-Arg-Ser-Ala-Cys-Ser-Cys-Arg-Val-Leu-Ser-Leu-Asn-Cys | 92 |
| ASIP-YY (ASIP 80-132, Q115Y, S124Y) | Lys-Lys-Val-Val-Arg-Pro-Arg-Thr-Pro-Leu-Ser-Ala-Pro-Cys-Val-Ala-Thr-Arg-Asn-Ser-Cys-Lys-Pro-Pro-Ala-Pro-Ala-Cys-Cys-Asp-Pro-Cys-Ala-Ser-Cys-Tyr-Cys-Arg-Phe-Phe-Arg-Ser-Ala-Cys-Tyr-Cys-Arg-Val-Lys-Ser-Leu-Asn-Cys | 93 |
| ASIP-YY 93-132 subdomain (ASIP 93-132, Q1157, S124Y) | Cys-Val-Ala-Thr-Arg-Asn-Ser-Cys-Lys-Pro-Pro-Ala-Pro-Ala-Cys-Cys-Asp-Pro-Cys-Ala-Ser-Cys-Tyr-Cys-Arg-Phe-Phe-Arg-Ser-Ala-Cys-Tyr-Cys-Arg-Val-Lys-Ser-Leu-Asn-Cys | 94 |

Example 4: Preparation of Multisome Lipid Vesicle Composition

Biphasic vesicles with multiple/synergistic penetration enhancers (Multisomes) were formulated using the procedure described herein. In some embodiments, the multisomes may comprise a peptide antagonist of a melanocortin 1 receptor, such as those described herein.

The general procedure for multisome preparation was as follows:

1) The oil phase and aqueous phase ingredients were weighed out in separate beakers.
2) Both beakers were heated to ~70° C. to completely melt and incorporate all components.
3) The water phase was added to the oil phase, while stirring vigorously to form an o/w crude emulsion, effectively yielding a homogenous solution (~2 to 6 min) in the 70° C. water bath. The temperature of the solution was reduced to ~55 to 65° C.
4) The formulation was batch processed using the LV1 Microfluidizer or Nano DeBee homogenizer with Z5 module three times at ~20,000 psi.

Some of the multisome formulations that were prepared comprised a peptide. The peptide was a melanocortin receptor 1 antagonist. The melanocortin receptor 1 antagonist was mixed into the water phase in the procedure described herein.

Procedure for Vesicle Formation:
1) The lipid phase components were weighed into a 20 mL glass vial.
2) The vial was heated to ~70° C. in a water bath to completely melt and incorporate all components.
3) The water phase was added to the liquid phase while stirring vigorously for ~10 to 20 min until the temperature of the solution was ~ 60° C.

In some cases, the mixture was intermittently vortexed and heated for 5 sec/5 sec for 8-10 cycles until a uniform creamy lotion formed.

Figure 2:
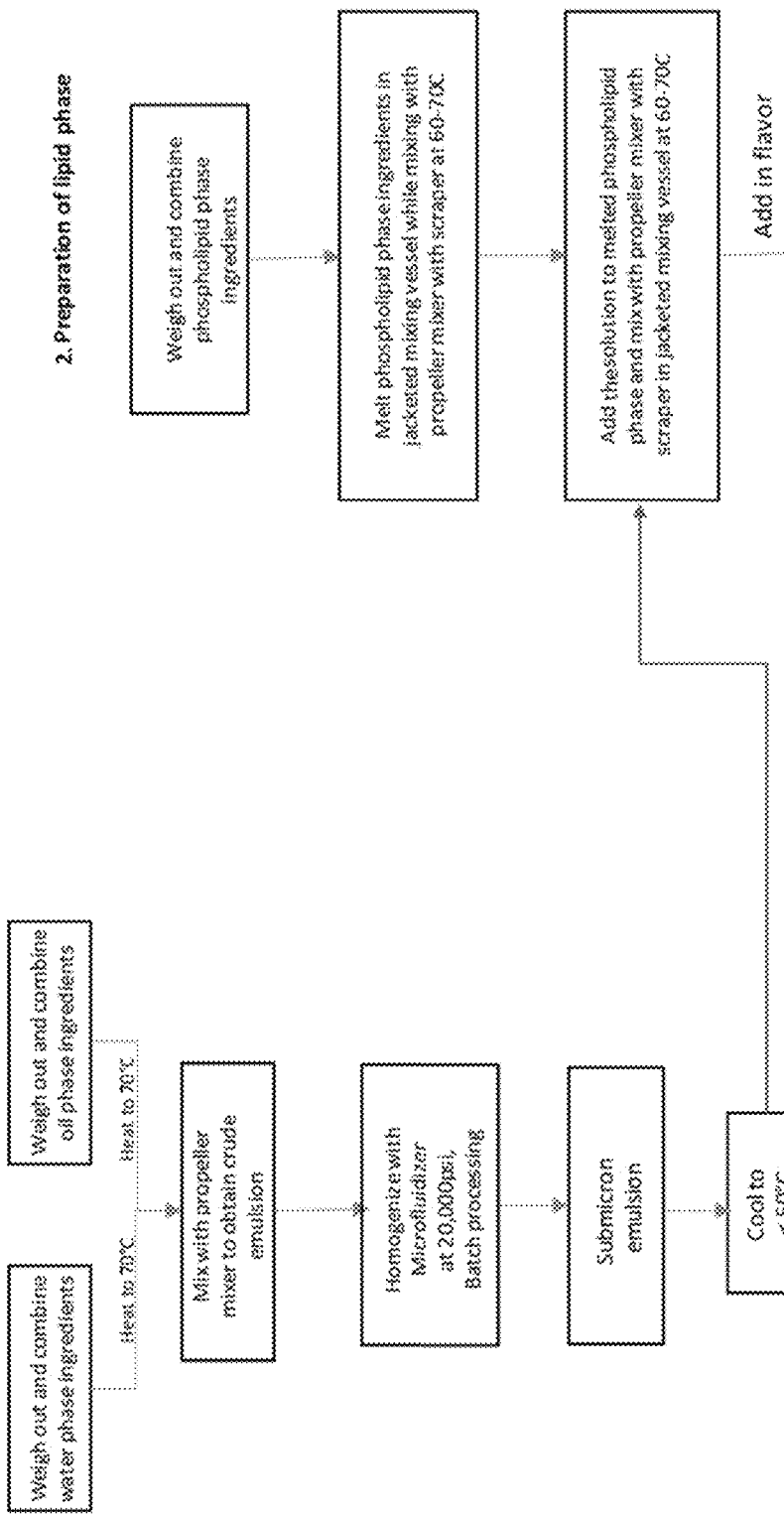
FIG. 2 shows an exemplary workflow for the preparation of lipid vesicles comprising a peptide as provided herein.
Figure 2:
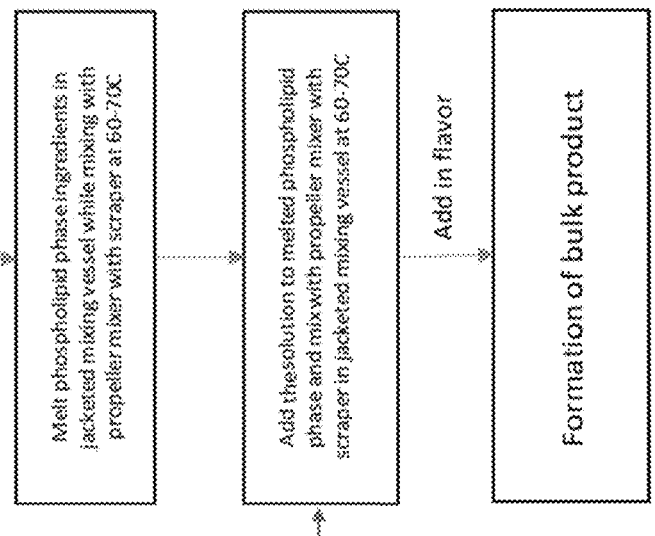

A pictorial representation of this process is shown in FIG. 1. A flow chart of this exemplary process is shown in FIG. 2.

Example 5: Methods of Analysis and Characterization

The following methods are used to characterize the formulations prepared using the method of Example 4 well as the performance of the formulation. The formulations prepared using Example 4 contain peptide antagonist of melanocortin 1 receptors, such as any one of SEQ ID NOs: 4-90.

Physicochemical characterization—Organoleptic observations, light microscopy and confocal microscopy are carried out to characterize the formulations.

Size (hydrodynamic diameter), polydispersity index and zeta (g) potential measurements are carried out on formulations prepared with non-labelled peptides using a dynamic light scattering (DLS) instrument, for example, the Zetasizer NanoZS (Malvern Instruments, Worcestershire, UK). Aliquots of formulations are assessed for particle size distribution and subsequently diluted with water for zeta potential measurements. Measurements are carried out in triplicates.

In vitro diffusion cell study—Full thickness human skin samples are obtained from an approved vendor. The obtained skin samples are stored at about −20° C. until use.

Absorption of the one or more peptides from formulations into excised human skin in vitro is evaluated using diffusion cells, for example, 9 mm diameter Bronaugh-type teflon flow-through diffusion cells with an exposed surface area of about 0.6 cm$^2$. The cell holder is maintained at about 32° C. by a circulating water bath heater. A perfusion fluid is used in the diffusion cell, for example, degassed phosphate-buffered saline (PBS) buffer with 0.05% sodium-azide pH 7.2, maintained at 37° C., with a flow rate of 1 mL/h. Skin samples are removed from the freezer and cut into about 1 cm×1 cm square pieces and mounted into the diffusion cells epidermis facing up. The multisome formulations with one or more peptides or control blank formulations are applied to the skin at t=0 and the cells are covered with a teflon cap to provide occlusion. Application is performed for periodically and transdermal fractions are collected into tissue culture tubes using a programmed fraction collector.

Transdermal fraction analysis—The transdermal fractions are collected periodically for analysis, for example hourly for 24 h. The samples are sent for analysis to a laboratory.

The skin samples from the diffusion cell study are cleansed by the usual protocol to remove residual bound cream, i.e. after the skin samples are removed from the diffusion cells and washed with water, and patted dry with a kimwipe. The cleansed skin discs are stored at about −20° C.

Results and Discussion

Multisome Formulation Optimization and Characterization

All formulations are lotion or cream consistency suitable for topical application. The formulations are physically stable showing no separation, sedimentation or other signs of stability issues for >1 mo of storage at about 4° C.

These formulations are shown to be polydisperse with ranging vesicle sizes as shown in light microscopic images. The microscopic observations confirm the formation of multisomes with the typical biphasic vesicle morphology and the uniform distribution of vesicles throughout the formulation for one or more peptide-containing and blank (no peptide) formulations.

Each of the one or more peptide-containing formulations are similar with respect to size distribution compared to their respective blank formulations, but overall, the blank formulations have narrower size distribution compared to the peptide formulations. Zetasizer data show consistent results with the microscopic observations, typical of multisomes.

Lipid vesicle formulations are prepared with one or more peptide and applied to skin samples. Blank versions of each formulation are prepared as controls, and a solution of the one or more peptides in water is prepared as an additional control. Each formulation is tested in triplicates and blank formulations, skin without any formulations applied, and the one or more peptide solution as free, non-encapsulated peptides are used for background fractions for the analysis.

Diffusion Cell Study—Transdermal Delivery of Peptides

In this study the transdermal fractions are collected for further analysis by mass spectrometry by a laboratory. The total amount (Qt (24 h)) of the peptides delivered through the diameter skin disk applied in the diffusion cells and the delivery rates for each formulation are measured.

These studies show that all multisome formulations delivered peptides (SEQ ID NOs: 1-90) deeply into and through the human skin in vitro.

These studies further show that the peptides in the multisome formulation are delivered deeper into and through the human skin in vitro compared to those that are not in the multisome formulation or are terminally modified, for example to include palmitoyl.

Example 6. Evaluation of the Safety and Efficacy of Peptides Compared to Placebo for Facial Application A lipid vesicle formulation of one or more peptides of the disclosure is tested for safety and efficacy for facial application of dark spots in a randomized, double-blind human clinical trial. An amount of the lipid vesicle formulation, or placebo (blank lipid vesicle) is applied to dark spots on the faces of individuals on Day 1.

Primary outcome: Percentage of Participants Achieving a Score of None or Mild by Investigator-Assessment of Dark Spot Scale With Photonumeric Guide in dark spots.

On Day 30, the severity of the subject's dark spots with Photonumeric Guide: 0=none, 1=mild, 2=moderate or 3=severe is assessed. The percentage of participants with a score of none or mild is determined.

Primary outcome: Percentage of Participants Achieving a Score of None or Mild by Subject-Assessment of Dark Spot Scale With Photonumeric Guide.

Also on Day 30, the subjects assess the severity of their dark posts using the 4-point dark Spot Scale with Photonumeric Guide: 0=none, 1=mild, 2=moderate or 3=severe and the percentage of participants with a score of none or mild is determined.

Secondary outcome: Percentage of Participants Achieving Satisfied or Very Satisfied by Subject Assessment of Satisfaction of Appearance of Dark Spots (participant assessment).

On Day 30, participants rate their overall satisfaction with the appearance of the dark spot area using a 5-point scale: 1=very unsatisfied, 2=unsatisfied, 3=neutral, 4=satisfied or 5=very satisfied. The percentage of participants with a rating of satisfied or very satisfied is determined.

Secondary outcome: Percentage of Participants With a=1 Grade Improvement from Baseline by Investigator-Assessed dark spot scale.

At baseline and on Day 30, the Investigator assesses the severity of the subject's dark spots using the dark spot scale: 0=none, 1=mild, 2=moderate or 3=severe. The percentage of participants with a=1 grade improvement from baseline is determined.

Secondary outcome: Percentage of Participants With a=1 Grade Improvement from Baseline by Subject-Assessed dark spot scale in dark spots.

At baseline and on Day 30, the participant assesses the severity of their dark spots using the dark spot scale: 0=none, 1=mild, 2=moderate or 3=severe. The percentage of participants with a=1 grade improvement from baseline is determined.

Example 7. Evaluation of Peptide Antagonists to MC1R Binding Using Competition Assay The binding of Group A MC1R peptide antagonists of the disclosure was evaluated in a competition assay (MC1 Human Melanocortin GPCR Binding (Agonist Radioligand) Assay, Item 251100, Eurofins Discovery). Peptides were synthesized by AnaSpec (Fremont, CA). Human recombinant melanocortin MC1 receptors were expressed in CHO-K1 cells in modified HEPES-KOH buffer pH 7.0. A 3 μgs aliquot was incubated with 0.04 nM [$^{125}$I]NDP-α-MSH for 120 minutes at 37° C. Non-specific binding was estimated in the presence of 1 μM NDP-α-MSH. Receptors were filtered and washed, and the filters counted to determine [$^{125}$I]NDP-α-MSH specifically bound. Peptide antagonists of the disclosure having amino acid sequences as set forth in SEQ ID NOS: 11, 16, 25, 27, 32, 35, and 40 were screened at five concentrations. Inhibition curves were obtained by determining the reduction of bound α-MSH in the presence of an amount of, and/or by increasing amounts of, each peptide antagonist.

Using this assay, the effect of representative peptide antagonists were compared to that of a positive control peptide having the amino acid sequence set forth as SEQ ID NO: 1 (Melanostatine-5). Based on the percent inhibition relative to the agonist the $IC_{50}$ values were determined (Eurofins or AAT Bioquest $IC_{50}$ calculator). The $IC_{50}$ values for the control and test peptides are shown in Table 7.

TABLE 7

$IC_{50}$ of Peptide Antagonists

| $IC_{50}$ less than 200 nM | $IC_{50}$ between 200 nM to 500 nM | $IC_{50}$ greater than 500 nM |
|---|---|---|
| SEQ ID NO: 1<br>SEQ ID NO: 16<br>SEQ ID NO: 32 | SEQ ID NO: 11 | SEQ ID NO: 27<br>SEQ ID NO: 25<br>SEQ ID NO: 35<br>SEQ ID NO: 40 |

Example 8. Evaluation of the Efficacy of Peptides for Facial Application

A lipid vesicle formulation comprising a peptide of Example 7 was tested for efficacy for facial application of dark spots in a human clinical trial of 15 subjects. The subjects, both male and female, ranged between 35 to 65 years of age. All subjects had Fitzpatrick skin types II-IV and had at least one moderate to severe solar lentigo that was approximately the size of a pencil eraser. 50% of the subjects were Caucasian and 50% were non-Caucasian, including Hispanic, Asian, African American, East Indian, native America, and Middle Easter ethnicities.

The skincare regiment for the subjects included the use of a cleaner on the face, followed by application of the lipid vesicle formulation, and further followed by the application of a moisturizer to the skin of the face. The skincare regiment was followed twice a day, in the morning and at night. The morning skincare regiment further included the application of a sunscreen with SPF50+ to the skin of the face.

Figure 3:
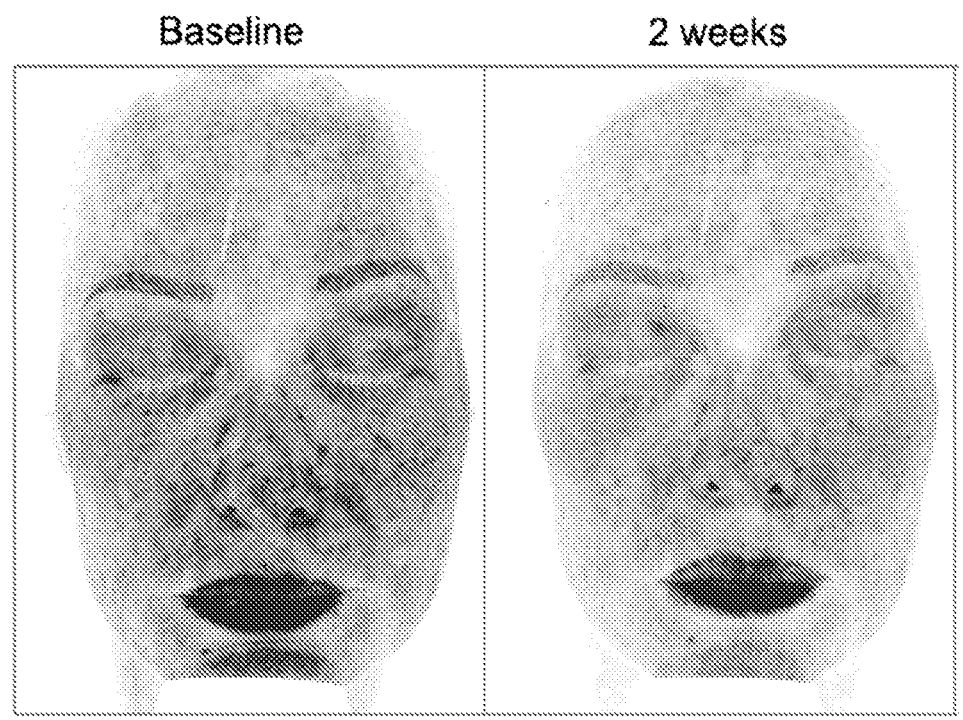
FIG. 3 shows an exemplary result of a subject from a clinical study.

The skincare routine was followed for two weeks. The skin of the faces of the subjects were analyzed after two weeks using the Visia® CR skin analysis imaging system. An exemplary result from a subject is shown in FIG. 3. As shown, the dark spots on the face of the subject was visibly reduced after two weeks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A melanocortin 1 receptor (MC1R) peptide antagonist comprising an amino acid sequence:

Xaa1-Xaa2-Xaa3-Xaa4-Xaa5-Xaa6-Xaa7-Xaa8-Xaa9 wherein:
   Xaa1 is absent or selected from the group consisting of: Cys, Met, Sec, Ser, Thr, D-Cys, D-Met, D-Sec, D-Ser, D-Thr, Ala, Gly, Val, Leu, Ile, D-Ala, D-Val, D-Leu, D-Ile, Phe, Trp, Tyr, D-Phe, D-Trp, D-Tyr, Asn, Asp, Gln, Glu, D-Asn, D-Asp, D-Gln, and D-Glu,;
   Xaa2 is selected from the group consisting of: Val, Ile, D-Val, and D-Ile;
   Xaa3 is selected from the group consisting of: Phe and D-Phe;
   Xaa4 is selected from the group consisting of: Arg and D-Arg;
   Xaa5 is selected from the group consisting of: Trp and D-Trp;
   Xaa6 is selected from the group consisting of: Phe and D-Phe;
   Xaa7 is selected from the group consisting of: Lys and D-Lys;
   Xaa8 is selected from the group consisting of: Pro and D-Pro;
   Xaa9 is selected from the group consisting of: Val and D-Val;
   and
   wherein Xaa1 or Xaa2, and Xaa9 are terminal amino acids.

2. The melanocortin 1 receptor peptide antagonist of claim 1, wherein:
   Xaa2 is selected from the group consisting of: Val and D-Val.

3. The melanocortin 1 receptor peptide antagonist of claim 1, wherein:
   Xaa2 is selected from the group consisting of: Ile and D-Ile.

4. The melanocortin 1 receptor peptide antagonist of claim 1, wherein:
   Xaa1 is absent or selected from the group consisting of: Cys, Sec, Ser, Thr, D-Cys, D-Met, D-Sec, D-Ser, D-Thr, Ala, Gly, Val, Leu, D-Ala, D-Val, D-Leu, D-Ile, Phe, Trp, Tyr, D-Phe, D-Trp, D-Tyr, Asn, Asp, Gln, Glu, D-Asn, D-Asp, D-Gln, and D-Glu.

5. The melanocortin 1 receptor peptide antagonist of claim 1, wherein:
   Xaa1 is absent or selected from the group consisting of: D-Cys, D-Met, D-Sec, D-Ser, D-Thr, Ala, Gly, Val, Leu, Ile, D-Ala, D-Gly-D-Val, D-Leu, D-Ile, Phe, Trp, Tyr, D-Phe, D-Trp, D-Tyr, Asn, Asp, Gln, Glu, D-Asn, D-Asp, D-Gln, and D-Glu.

6. The melanocortin 1 receptor peptide antagonist of claim 1, wherein:

Xaa1 is absent or selected from the group consisting of: Cys, Sec, D-Cys, D-Met, D-Sec, D-Ser, D-Thr, Gly, Val, Ile, D-Ala, D-Val, D-Leu, D-Ile, D-Phe, D-Trp, D-Tyr, Asn, Asp, D-Asn, D-Asp, D-Gln, and D-Glu.

7. The melanocortin 1 receptor peptide antagonist of claim 1, wherein:

Xaa2 is selected from the group consisting of: Val and Ile.

8. The melanocortin 1 receptor peptide antagonist of claim 1, wherein:

Xaa1 is absent or selected from the group consisting of: Phe, Trp, Tyr, D-Phe, D-Trp, and D-Tyr;

Xaa2 is selected from the group consisting of: Val, Ile, D-Val, and D-Ile;

Xaa3 is selected from the group consisting of: Phe and D-Phe;

Xaa4 is selected from the group consisting of: Arg and D-Arg;

Xaa5 is selected from the group consisting of: Trp and D-Trp;

Xaa6 is selected from the group consisting of: Phe and D-Phe;

Xaa7 is selected from the group consisting of: Lys and D-Lys;

Xaa8 is selected from the group consisting of: Pro and D-Pro; and

Xaa9 is selected from the group consisting of: Val and D-Val.

9. The melanocortin 1 receptor peptide antagonist of claim 1, wherein the N-terminus is modified to comprise $C_1$-$C_6$ acyl, $C_1$-$C_8$ alkyl, $C_6$-$C_{12}$ aralkyl, $C_5$-$C_{10}$ aryl, $C_4$-$C_8$ heteroaryl, formyl, or a lipid.

10. The melanocortin 1 receptor peptide antagonist of claim 1, wherein the C-terminus is modified to comprise $NH_2$, amino-acyl, amino-$C_1$-$C_8$ alkyl, amino-$C_6$-$C_{12}$-aralkyl, amino-$C_5$-$C_{10}$ aryl, amino-$C_4$-$C_8$ heteroaryl, or O—($C_1$-$C_8$ alkyl).

11. The melanocortin 1 receptor peptide antagonist of claim 1, wherein a lipid is covalently attached to a cysteine, serine, lysine, threonine or tyrosine.

12. A melanocortin 1 receptor antagonist comprising the amino acid sequence of any one of SEQ ID NOs: 4-90.

* * * * *